United States Patent [19]
Steele et al.

[11] Patent Number: 4,803,639
[45] Date of Patent: Feb. 7, 1989

[54] X-RAY INSPECTION SYSTEM

[75] Inventors: Douglas S. Steele; Larry C. Howington, both of West Chester; James W. Schuler, Oxford; Joseph J. Sostarich, Fairfield; Charles R. Wojciechowski, West Chester; Theodore W. Sippel, Cincinnati; Joseph M. Portaz, Hamilton; Ralph G. Isaacs, Cincinnati, all of Ohio; Henry J. Scudder, III, Medford; Thomas G. Kincaid, Lexington, both of Mass.; Kristina H. V. Hedengren, Schenectady, N.Y.; Rudolph A. A. Koegl, Niskayuna, N.Y.; John P. Keaveney, Schenectady, N.Y.; Joseph Czechowski, III, Clifton Park, N.Y.; John R. Brehm, Cincinnati, Ohio; James M. Brown, Jr., Albany, N.Y.; David W. Oliver, Schenectady, N.Y.; George E. Williams, Schenectady, N.Y.; Richard D. Miller, Schenectady, N.Y.

[73] Assignee: General Electric Company, Cincinnati, Ohio

[21] Appl. No.: 832,511

[22] Filed: Feb. 25, 1986

[51] Int. Cl.$^4$ .................. G06F 15/20; G01N 23/02
[52] U.S. Cl. ........................... 364/507; 378/4; 378/58; 73/600; 73/618
[58] Field of Search ................ 364/505-508, 364/550, 559, 560, 564, 414; 378/4, 8, 11, 20, 58, 62, 195-198; 73/599, 600, 602, 605, 606, 618, 619, 620, 622, 627, 633, 645, 646

[56] References Cited

U.S. PATENT DOCUMENTS

| | | | |
|---|---|---|---|
| 4,117,539 | 9/1978 | Bell et al. | 364/507 |
| 4,591,996 | 5/1986 | Vachon | 364/508 |
| 4,600,998 | 7/1986 | Huet | 364/507 |
| 4,615,093 | 10/1986 | Tews et al. | 364/550 |

Primary Examiner—Parshotam S. Lall
Assistant Examiner—Brian M. Mattson
Attorney, Agent, or Firm—Derek P. Lawrence; Nathan D. Herkamp

[57] ABSTRACT

An X-ray inspection system for manually or automatically performing digital fluoroscopy inspections and/or computed tomography inspections by X-ray examination of manufactured parts incorporates a computer system which automatically analyzes the inspected parts for flaws. The system includes apparatus for automatically positioning the parts in an X-ray machine for obtaining fluoroscopy and tomography views of the part and for acquiring data from the inspections at production rates. The system automatically identifies the location of rejectable flaws in the parts during the fluoroscopy scanning and subsequently identifies those locations for obtaining tomography scans, if the identified flaw location is questionable. The system can automatically reject parts containing flaws identified during the fluoroscopy inspections. This system operates in a real-time environment by providing analysis of one part while a subsequent part is being subjected to X-ray examination. The data obtained during each examination is archived and stored for tracking the part in further manufacturing processes.

18 Claims, 23 Drawing Sheets

Microfiche Appendix Included
(81 Microfiche, 4703 Pages)

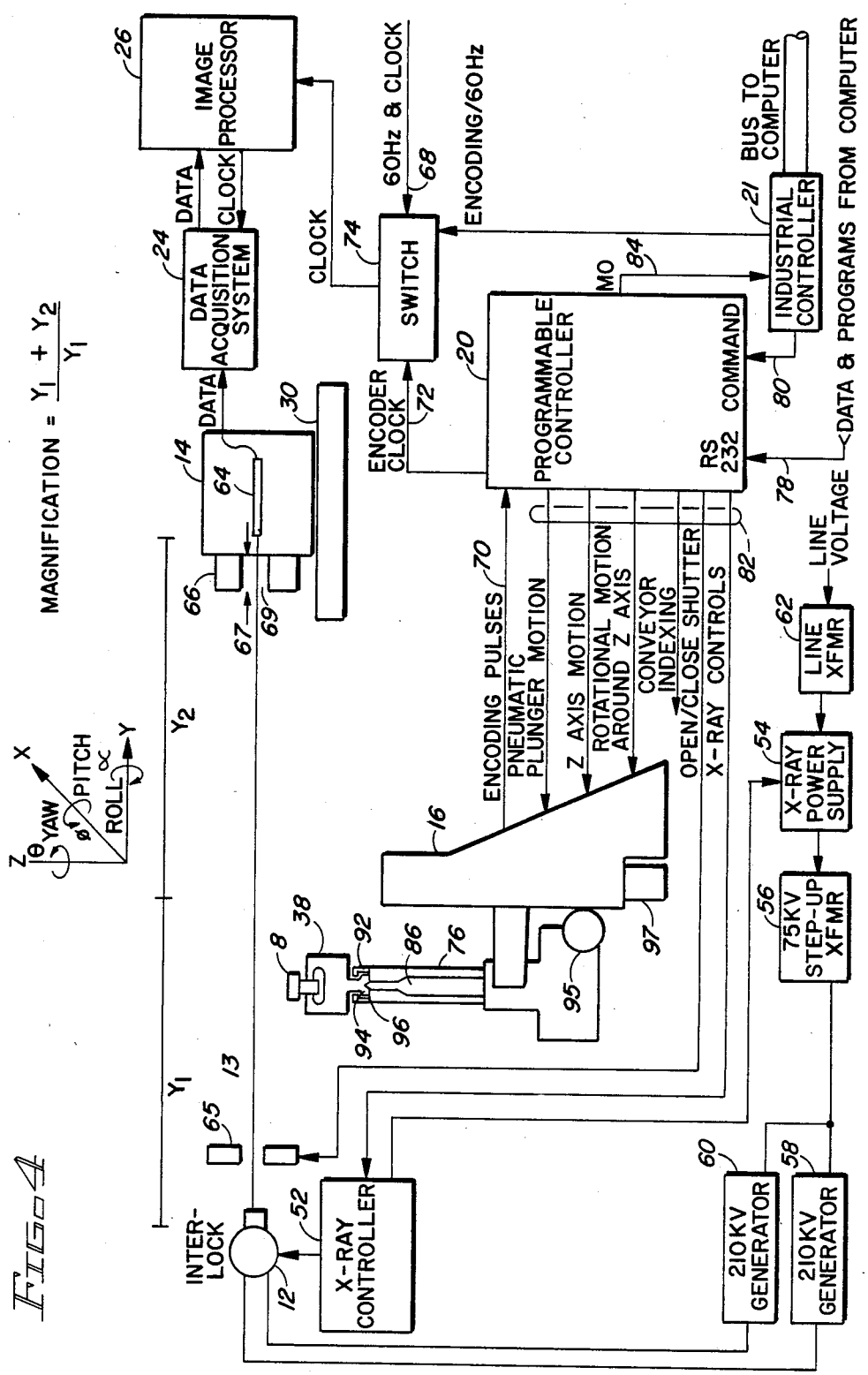

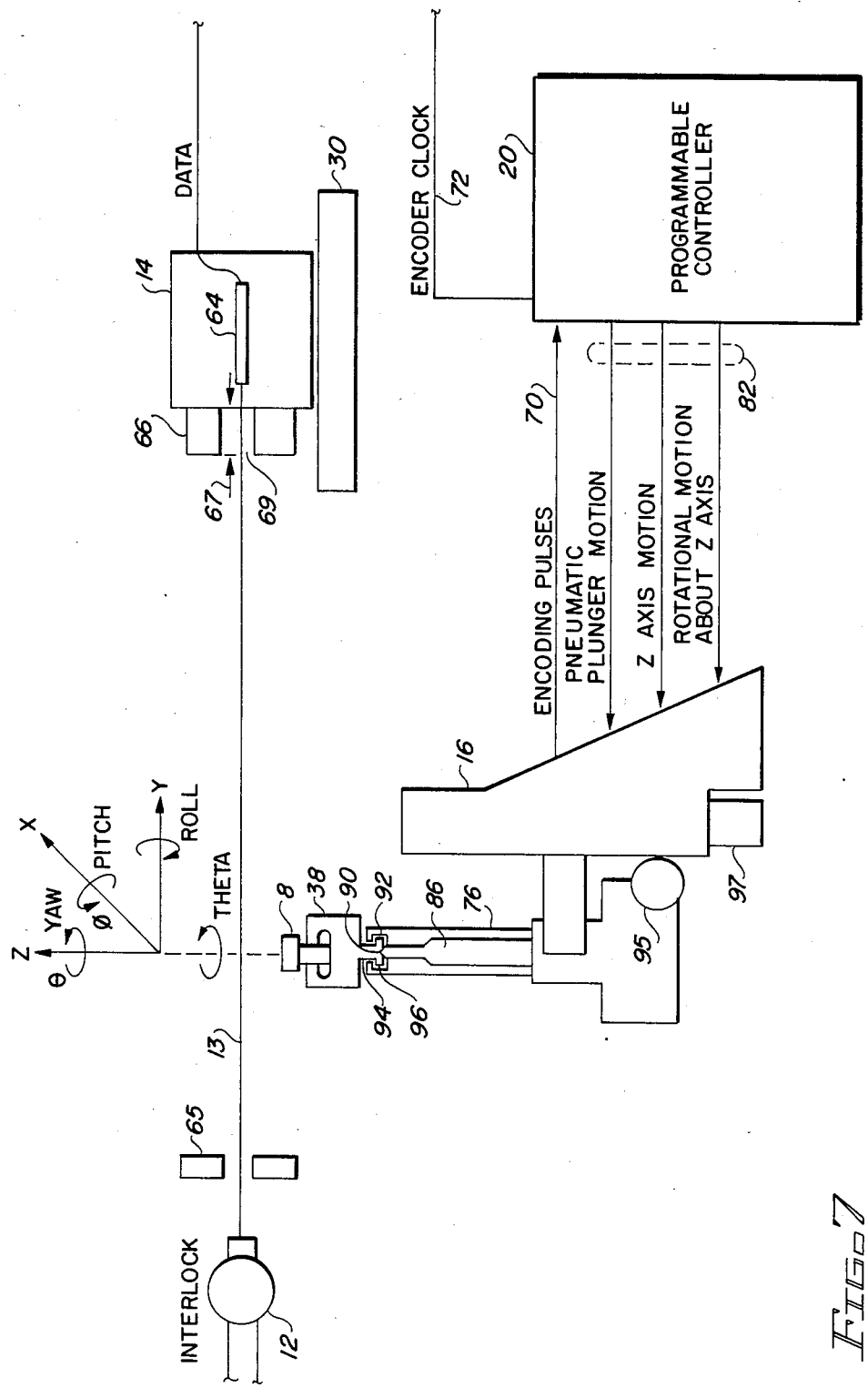

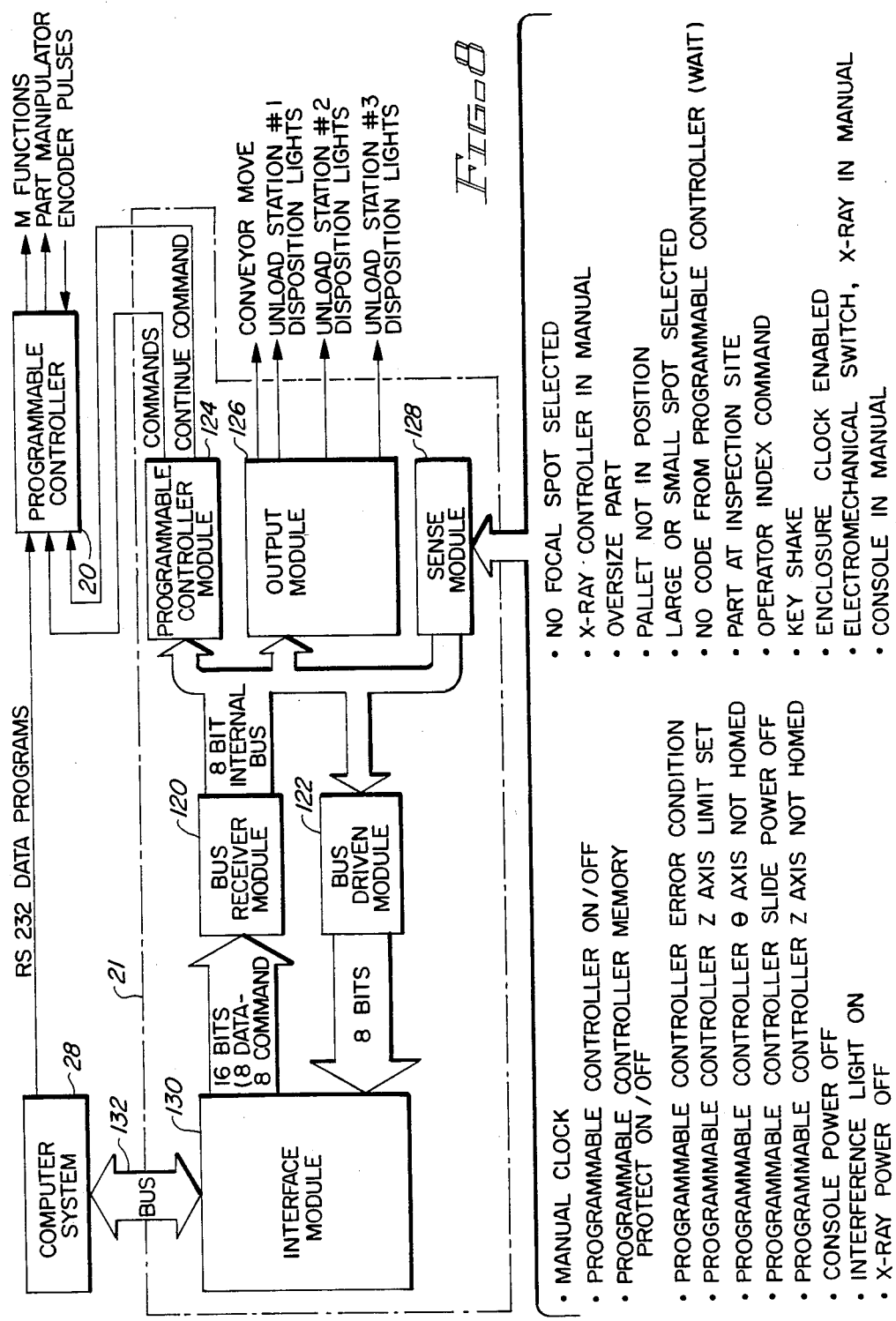

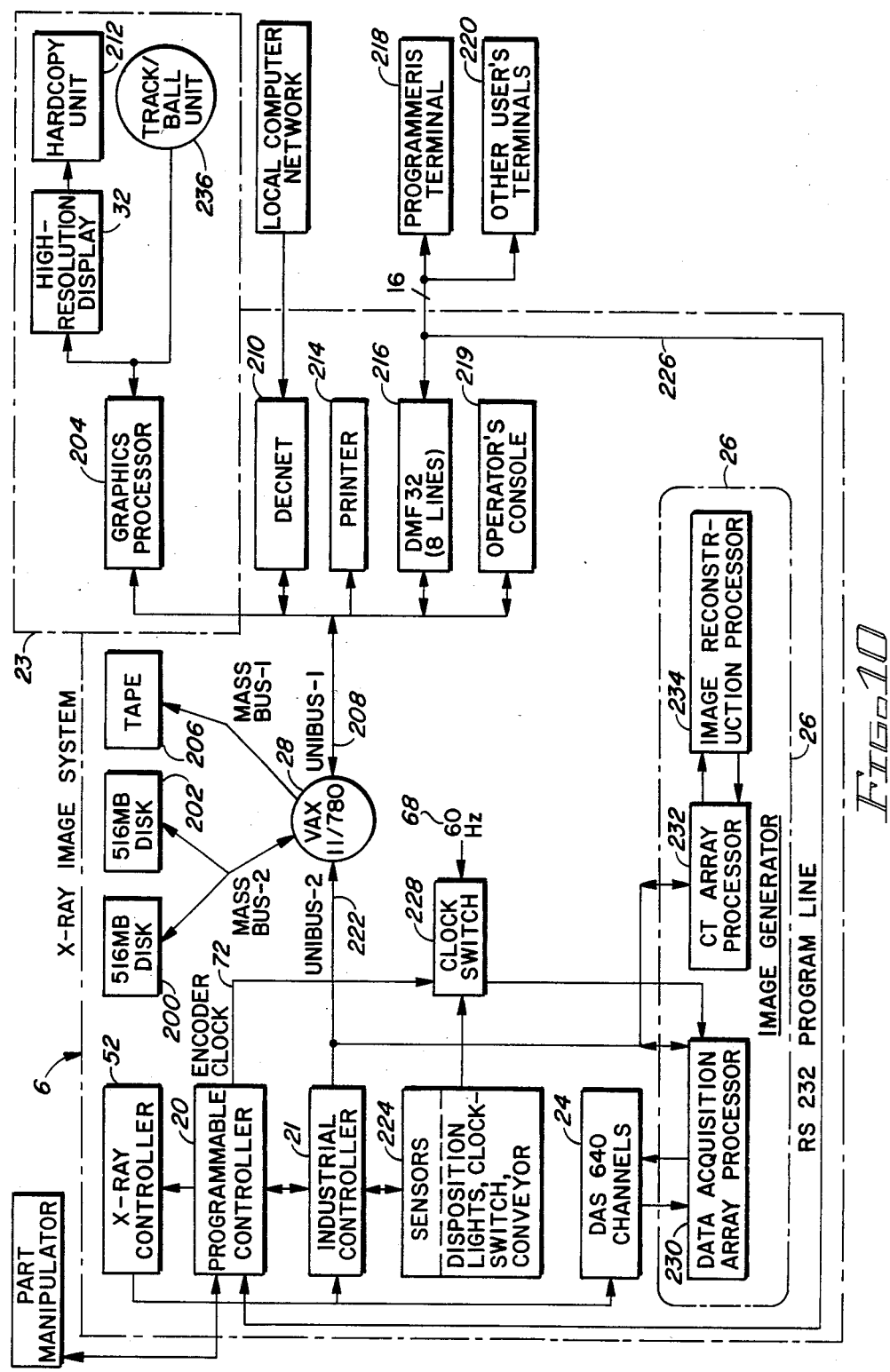

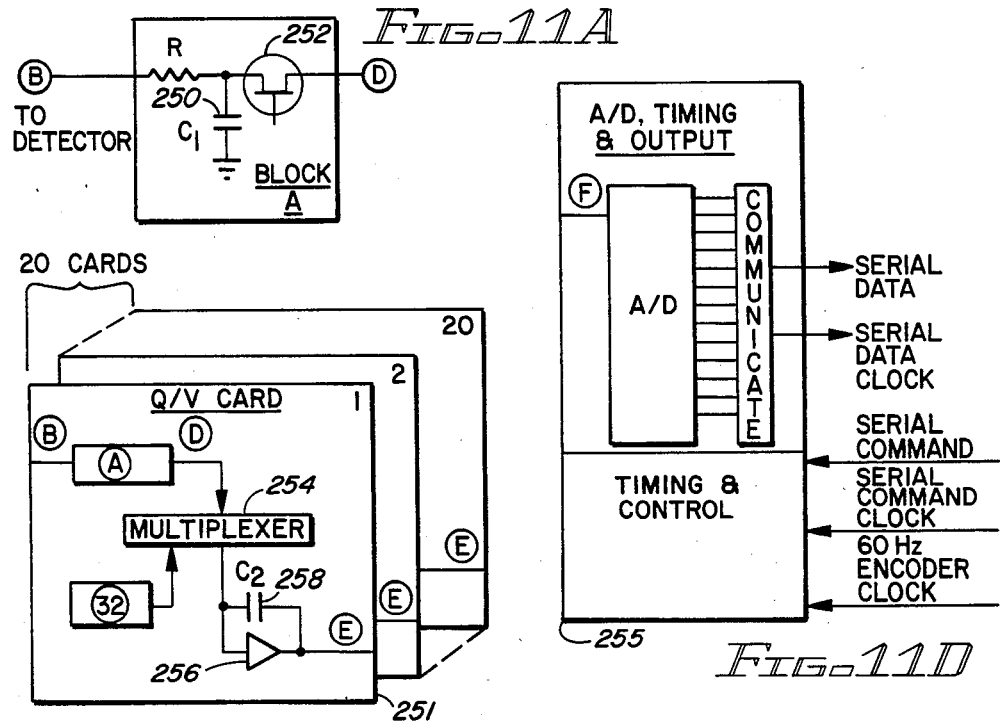
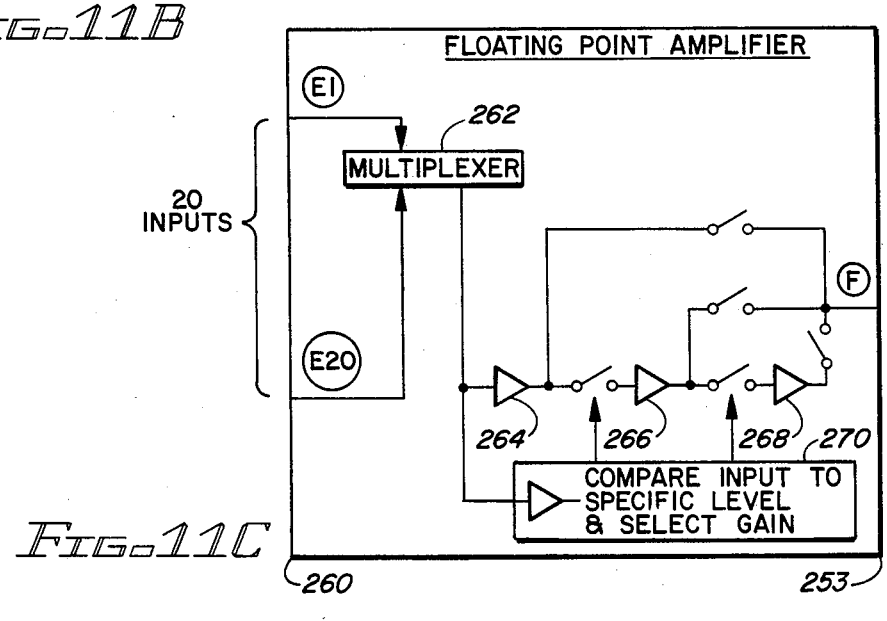

DF IMAGE

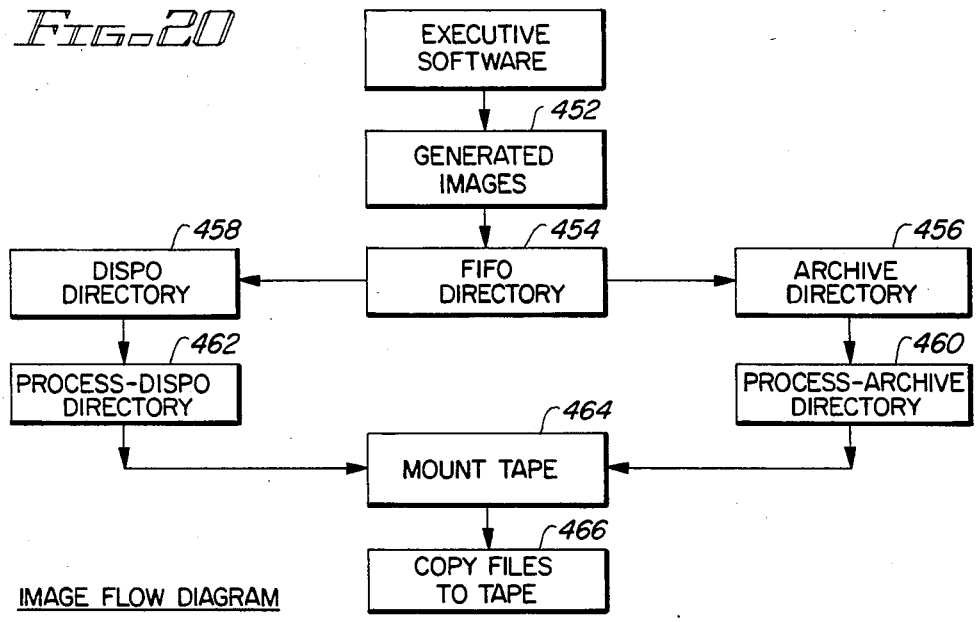
IMAGE FLOW DIAGRAM
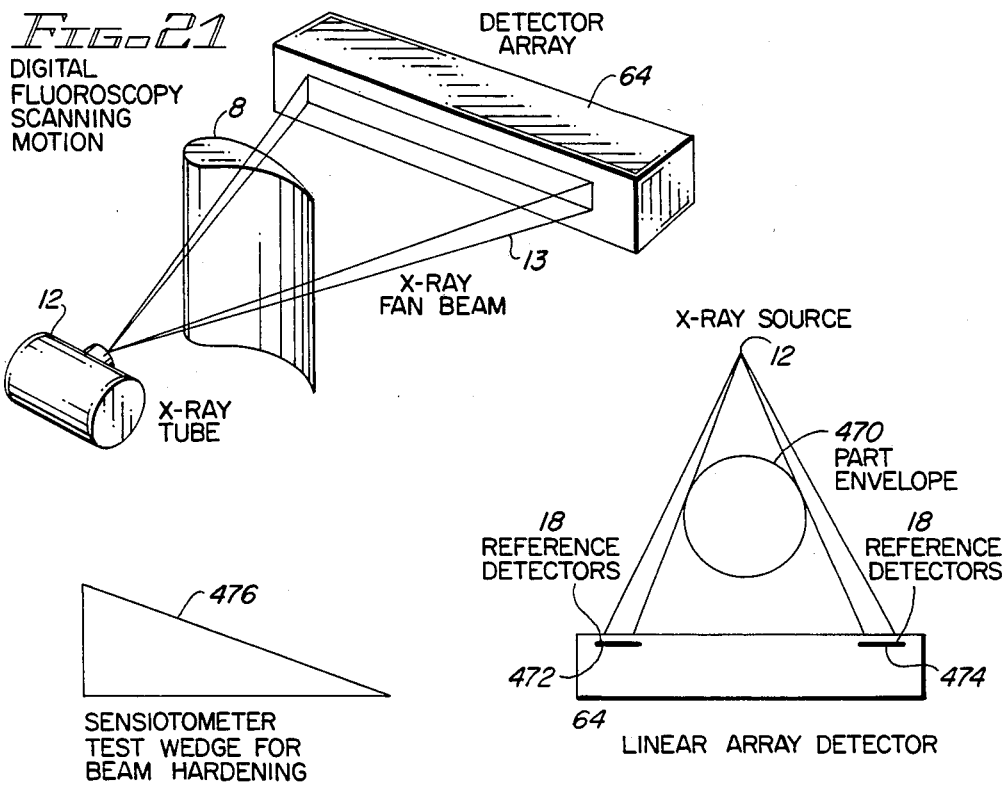

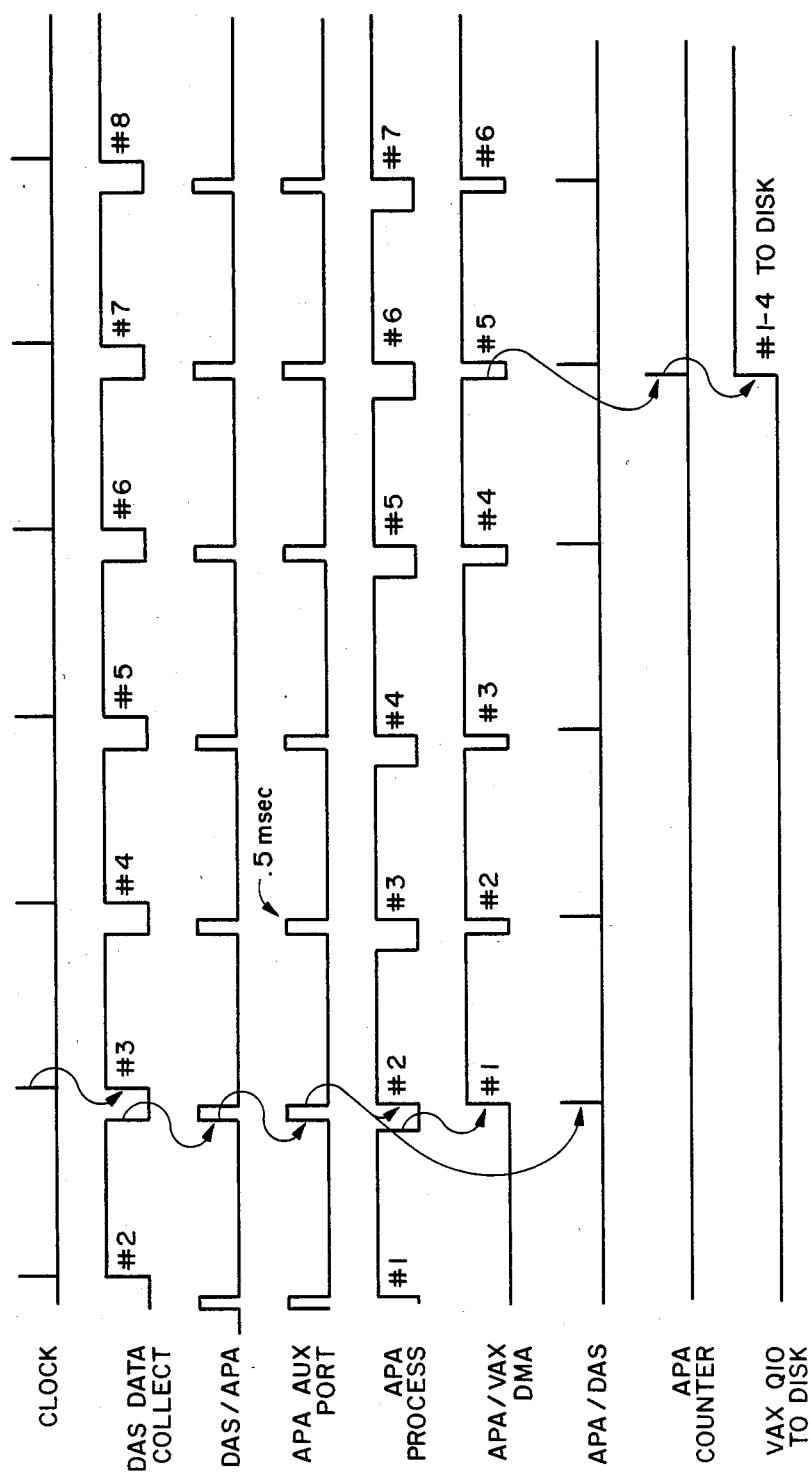

PART LOADING

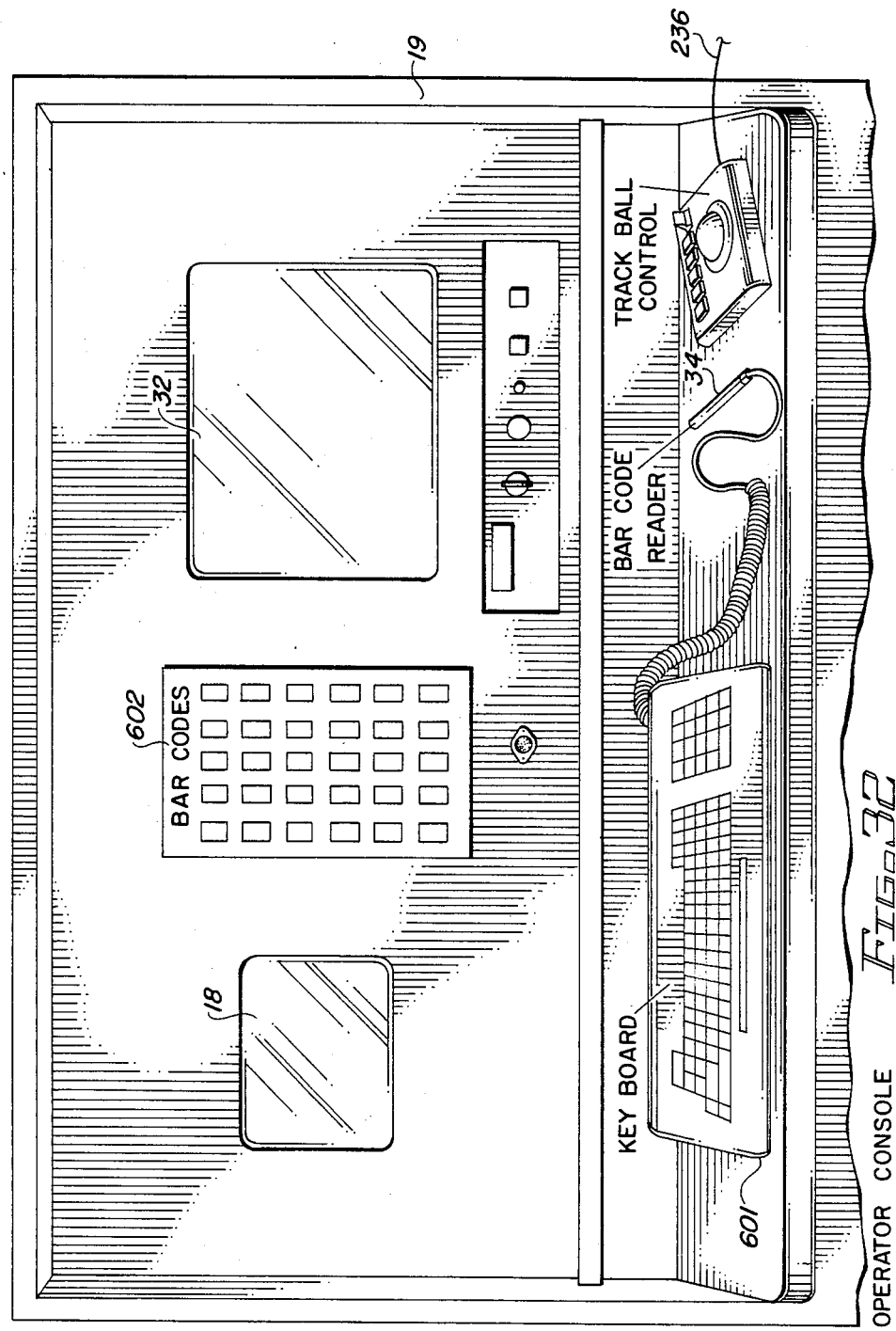

BARCODES
NON-CONF DESCRIPTION

| | | | |
|---|---|---|---|
| | FALSE START | OVERDRILL | U/MIN WALL |
| | DWELL MULTIPLE | MERGES | O/MAX DEPTH |
| | DWELL, ADJACENT HOLES | EXTRA HOLES | O/MAX GAP |
| O/MAX DWELL LENGTH | MISSIN HOLE | BRAZE GAP | |
| O/MAX DWELL DIAMETER | NOT THRU HOLE | BRAZE VOIDS | |

FIG. 33

X-RAY INSPECTION SYSTEM

1. BACKGROUND

This application contains a microfiche appendix having 81 sheets of microfiche

A. Field of the Invention

This invention generally relates to X-ray inspection of manufactured parts, and more particularly, to an automated digital X-ray inspection system for evaluating aircraft engine gas turbine blades.

B. Discussion turbine engines has led to the development of turbine blades containing complex interior passages and openings to the blade surface for blade cooling. The performance and life of the blades is dependent upon the manufacture of these interior structures within specifications. A high penalty exists for blade failure because of machinery damage, incompletion of mission, and hazard to personnel. For these reasons 100 percent inspection of turbine blades is important to the public and a highly automated digital X-ray inspection station system has long been desired.

The problem of turbine blade inspection by X-ray has both special requirements and general requirements shared by many other applications, including nondestructive evaluation methods not using X-rays. The ability to handle many small parts rapidly in a factory production environment is a necessity. The ability to rapidly acquire and normalize X-ray images, to resolve small structures, to automatically interpret X-ray images and make decisions and to provide a convenient factory interface are very desirabl.e. A problem with production type nondestructive evaluation systems is in situations where a set of fixed criteria are applied to the nondestructive evaluation decisions by human observers. Where observations are to be made on many parts, nondestructive evaluation systems using human observers have a problem with observers who may tire or miss something. Another problem with nondestructive evaluation of turbine blades is the numerous recognitions of flaws that may occur in particular blades. Some of the representative flaws found in turbine blades are inclusions, gas porosity where fine holes or- pores within the metal are formed due to trapped gas, cold joint where an area of cold and hot metals flow together, but incomplete fusion takes place and hot tear where a fracture formed in the metal during solidification hinders contraction. A flaw may have microscopic voids left in the cast metals as a result of solidification shrinkage. Some other typical flaws are discontinuity in walls, skid marks, scarfing, undercoating, overdrills, dwell, form material, drilling restarts, laser spatter, incorrect spacing between holes, bad fusion welds, brazed gap and voids, brazed flow, brazed fill, improper or lack of penetration of holes into -the blade cavity, redrilling of original holes with air in true position, merged holes, quantity of holes, holes out of position, bad hole diameters and enlarged hole entrances due to washout from electrolyte flow. As is readily apparent, a need for automatically inspecting turbine blades is paramount.

Therefore, it is the object of the present invention to manually or automatically detect flaws in a single turbine blade and make a disposition as to the acceptability based on a quality inspection plan.

It is yet another object of this invention to identify the location of flaws in a single turbine blade.

It is another object of this invention to automatically position the turbine blade at an inspection site for performing digital fluoroscopy and computed tomography inspection.

It is another object of this invention to automatically make accept and reject decisions on turbine blades.

It is another object of this invention to acquire data for computed tomography inspections at least a maximum rate of 60 views per second.

It is yet a further object of this invention to acquire data for digital fluoroscopy inspections at a maximum rate of 60 views per second.

It is another object of this invention to display computerized tomography and digital fluoroscopy images for an operator in real time.

It is still another object of this invention to initiate analysis of a turbine blade X-ray data during the data acquisition time of the next blade to be inspected.

It is another object of this invention to provide the capability to convey inspection information that may be used for subsequent statistical analysis and feedback for quality control and repair.

It is another object of this invention to archive digital fluoroscopy or computed tomography images for future reference.

2. SUMMARY

An X-ray inspection system is comprised of an X-ray machine and an X-ray image system. The X-ray machine includes devices for manipulating parts, generating X-rays, detecting X-rays, and controlling the flow of parts through the X-ray machine. The X-ray image system includes computer hardware and software for acquiring X-ray data, image generation, archiving, displaying, performing computations, and controlling the X-ray machine. The system is a production type automatic inspection module capable of detecting internal flaws in jet engine turbine blades.

The X-ray inspection system manually or automatically performs X-ray computed tomography (CT) and digital fluoroscopy (DF) inspections on gas turbine engine blades. The system automatically positions single turbine blades to perform required CT and DF inspections, acquiring data for these inspections at a rate of at least 60 views per second, and identifying the location of rejectable flaws in the blades. It initiates the analysis of blade X-ray data for making accept/reject decisions during the data acquisition time of the next blade to be inspected. Thus, the system is capable of automatically detecting flaws in a real time environment. The system provides a reservoir of inspection information of the blades for subsequent statistical analyses and feedback for quality control and repair.

The X-ray inspection system operates in either a manual or automatic mode. The manual mode allows the operator to make a blade image, display the image, and repeat if necessary. The automatic mode performs automatic flaw detection, flaw analysis and blade disposition.

The blade inspection method proceeds as follows: for a group of similar blades, the operator enters in the computer console information required to select an inspection plan from the computer system. The first blade is then removed from an input box and a blade serial number entered in the computer console. The operator then manually inserts the blade into a conveyor gripper positioned at a load station. After the blade is positioned, the operator depresses the start buttons on the conveyor when ready. This operation is repeated for all the blades in the input box until it is empty. The conveyor advances the blades between load, inspection, and unload stations.

The blade and gripper are then automatically advanced to a part inspection station. Blade grippers have variable holding configurations for accommodating a variety of blades to be inspected, and are made of material of lower X-ray absorptivity compared to the blade material. A part manipulator controls the blade and gripper when positioned at a part inspection station. The part manipulator has two axes of movement: at least a vertical translation along the blade's dovetail axis and a rotation about the blade's dovetail axis. These motions orient the blade dovetail axis perpendicular to the axis of the X-ray beam and have sufficient range to inspect the whole blade. When a blade reaches the inspection station of the conveyor it is automatically removed from the conveyor by the manipulator and scanned in either the DF or CT mode or both, according to a predefined inspection plan. In manual operation the operator evaluates the DF image for determining whether a CT image is necessary.

The manipulation of the blades is specified by a scan plan which is part of the inspection plan for each representative part. Scan plans consist of vertical translations along the blade dovetail axis and rotations about the blade dovetail axis, for performing DF and CT inspections (respectively). The computer system decodes this information and provides the manipulator with appropriate control and synchronization signals.

After the scan is complete, the blade is returned to the conveyor. As the blades are advanced by the conveyor they are moved to an unload station. The operator removes each part from the unload station before loading the next part and dispositions the unloaded parts as indicated by the disposition lights. The disposition of the blade is either accept, provisional accept, or dispo. When all the parts in the box are inspected it may be necessary to reinspect a blade. The operator then cycles the reinspect blades through the inspection process. A dispo classification requires the blade to be further evaluated.

Blades dispositioned accept, provisional accept, dispo, or reinspect are manually removed at the unload station. A record of flaw analysis is provided for all inspected blades. The record contains a part identification number and flaw analysis which identifies each rejectable flaw and its location.

The software for the system consists of programs which direct the X-ray inspection system in near real time and those which provide an environment for image processing and inspection plan generation. The near real time system consists of an executive software which starts tasks, monitors tasks, checks error conditions, initializes the system and interfaces to the operator. There are four major subprocesses which are spun off as independent processes under supervision of the executive system. These are data acquisition, image display on the high resolution monitor, automatic image processing and automatic archiving processing. In manual operation while data is being acquired for one blade, data acquired previously for another blade is displayed to an operator for decision. In automatic operation, automatic flaw analysis is performed, while data is being acquired for the next blade. Thus, good use is made of overhead time such as loading indexing, mechanical positioning, and inspecting via parallel processes running in the X-ray image system.

3. BRIEF DESCRIPTION OF THE DRAWINGS

Figure 3A:
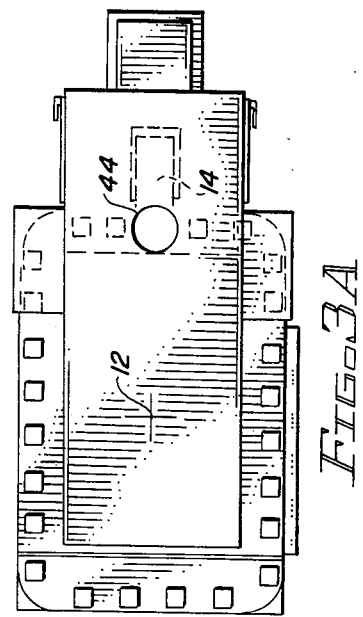
Figure 3B:
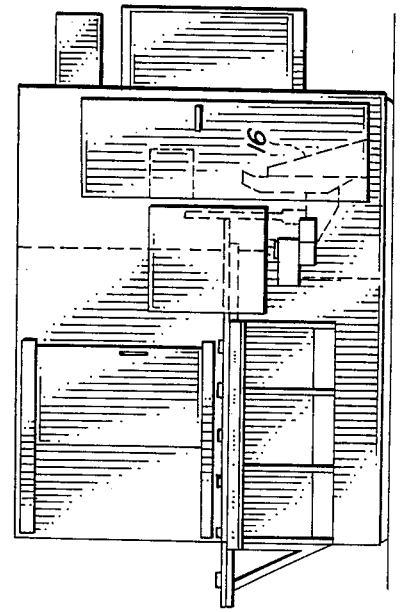

FIG. 3A-B shows a schematic diagram of the conveyor system and lead shielded chamber.

FIG. 4 illustrates the electromechanical apparatus of the X-ray machine.

Figure 5:
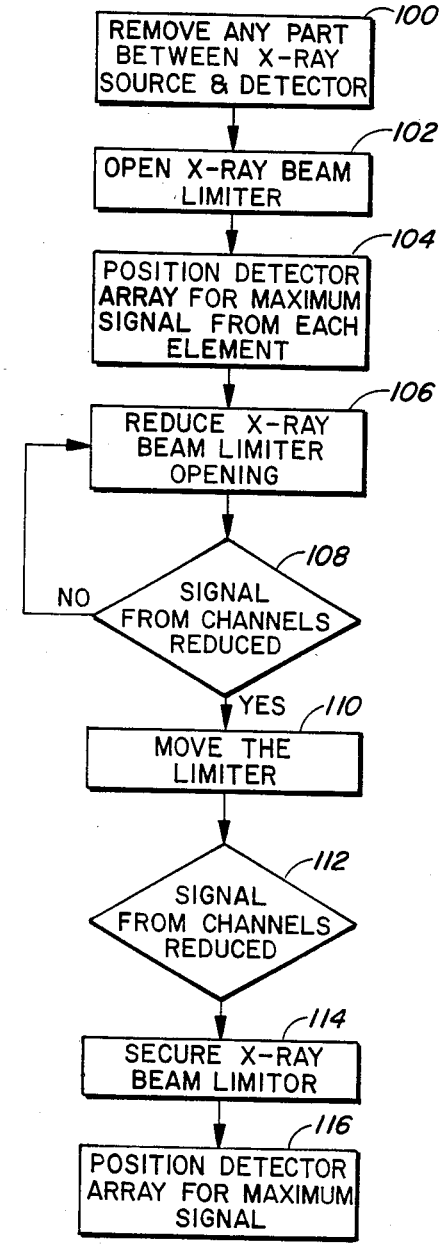

FIG. 5 is a method for aligning the detector to the X-ray source.

Figure 6:
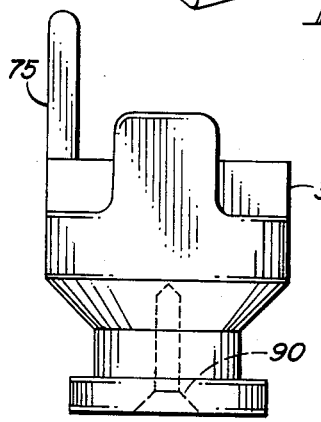

FIG. 6 is a gripper with an extension flange used for determining the center detector of the linear array detector.

FIG. 7 is a diagram of the part manipulator.

FIG. 8 illustrates a detailed flow diagram of data transfer between the computer system, industrial controller and the programmable controller.

Figure 9C:
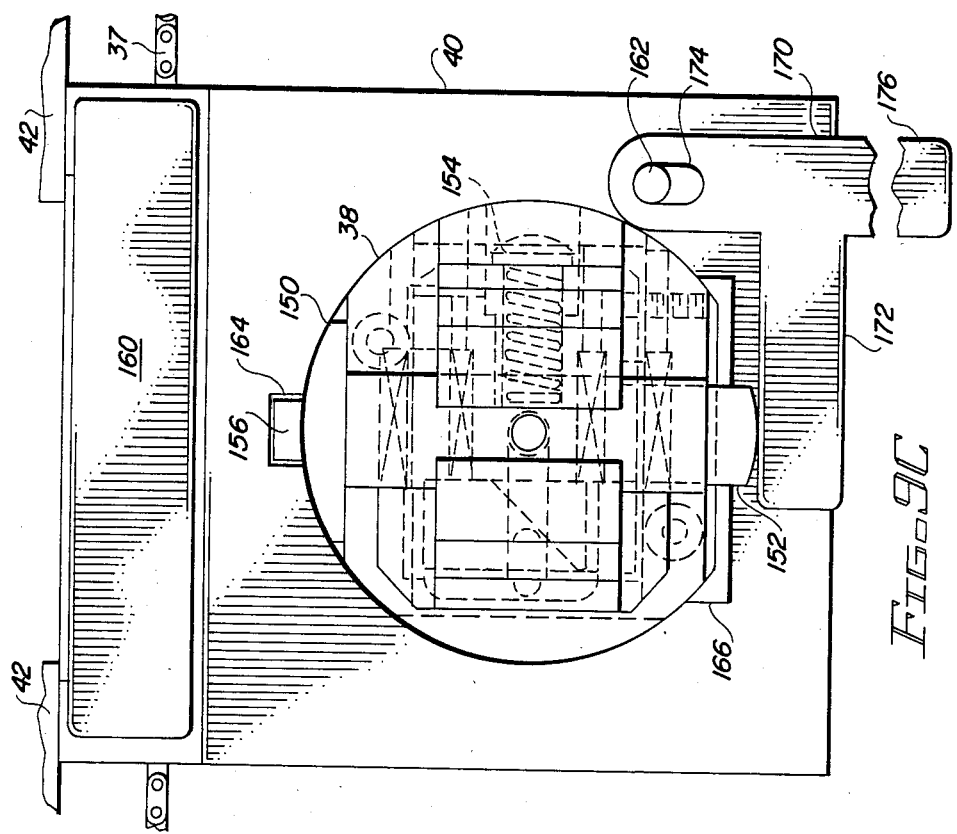
Figure 9A:
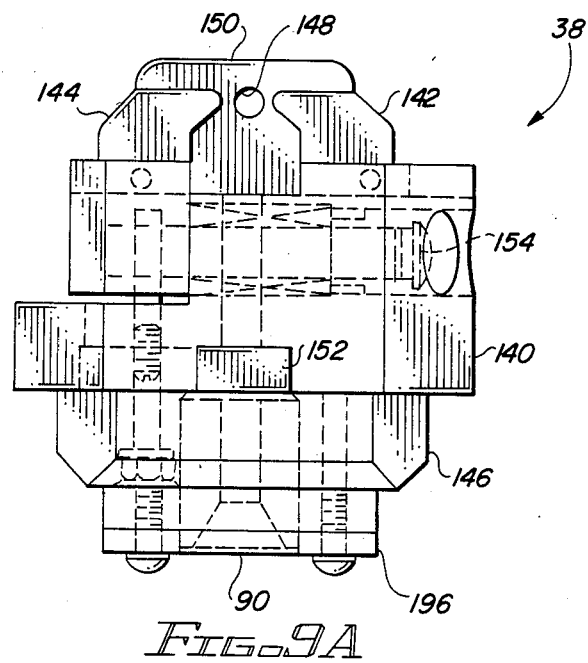
Figure 9B:
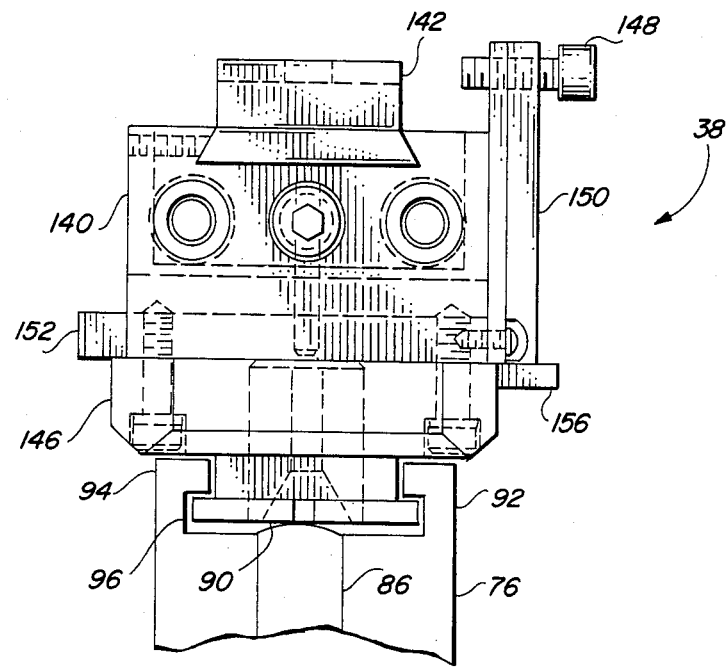

FIG. 9A-C show the gripper assembly of the present invention.

FIG. 10 shows a block diagram of the X-ray image system configuration.

FIG. 11A-D shows a detailed schematic of the digital acquisition system conversion.

Figure 12:
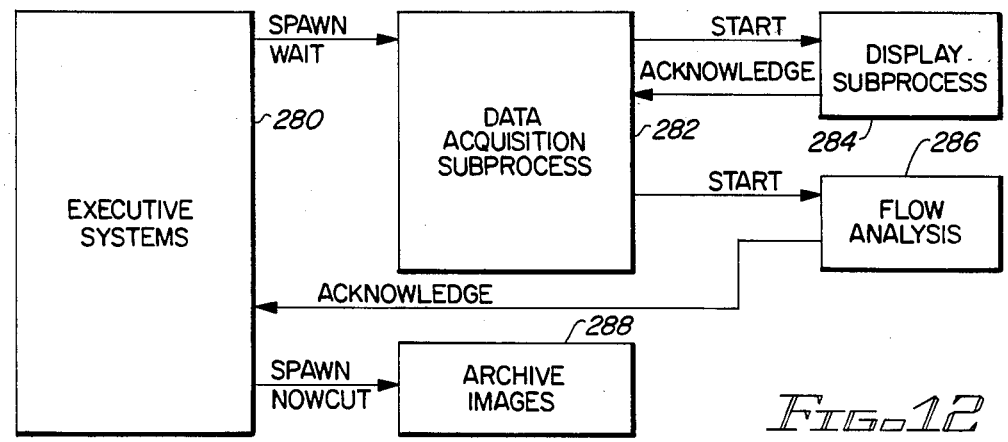

FIG. 12 illustrate the four major subprocesses of the software.

Figure 13:
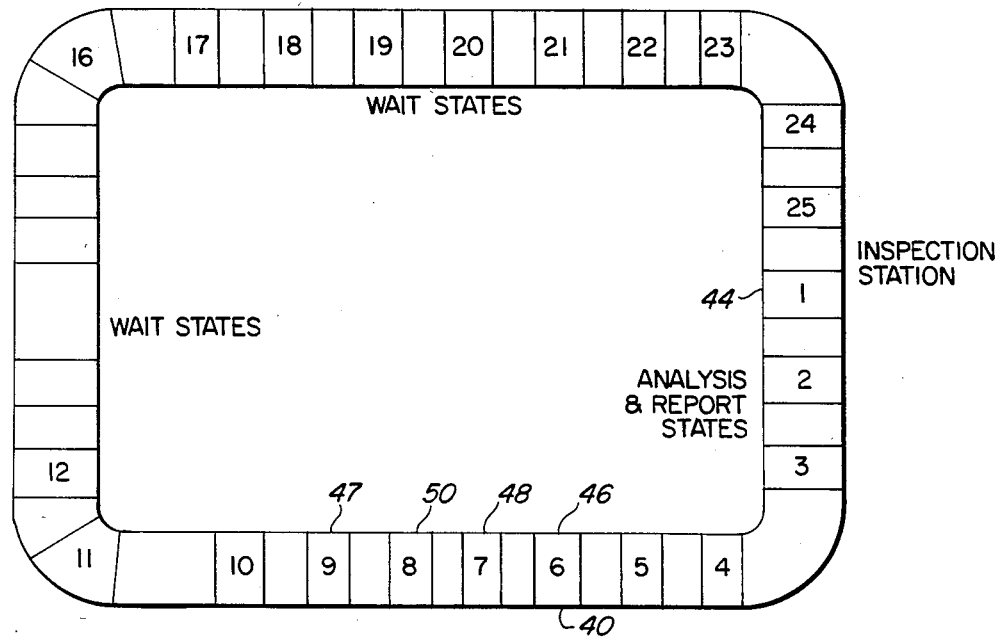

FIG. 13 is a physical diagram of the conveyor system.

Figure 14:
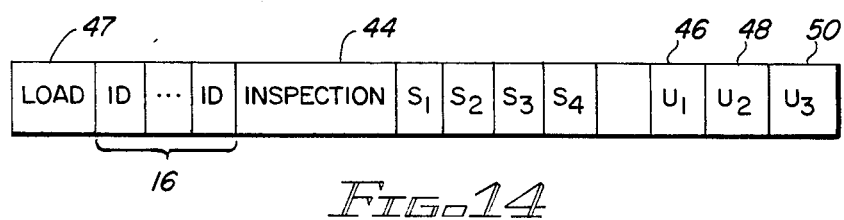

FIG. 14 is a computer model of the conveyor.

Figure 15:
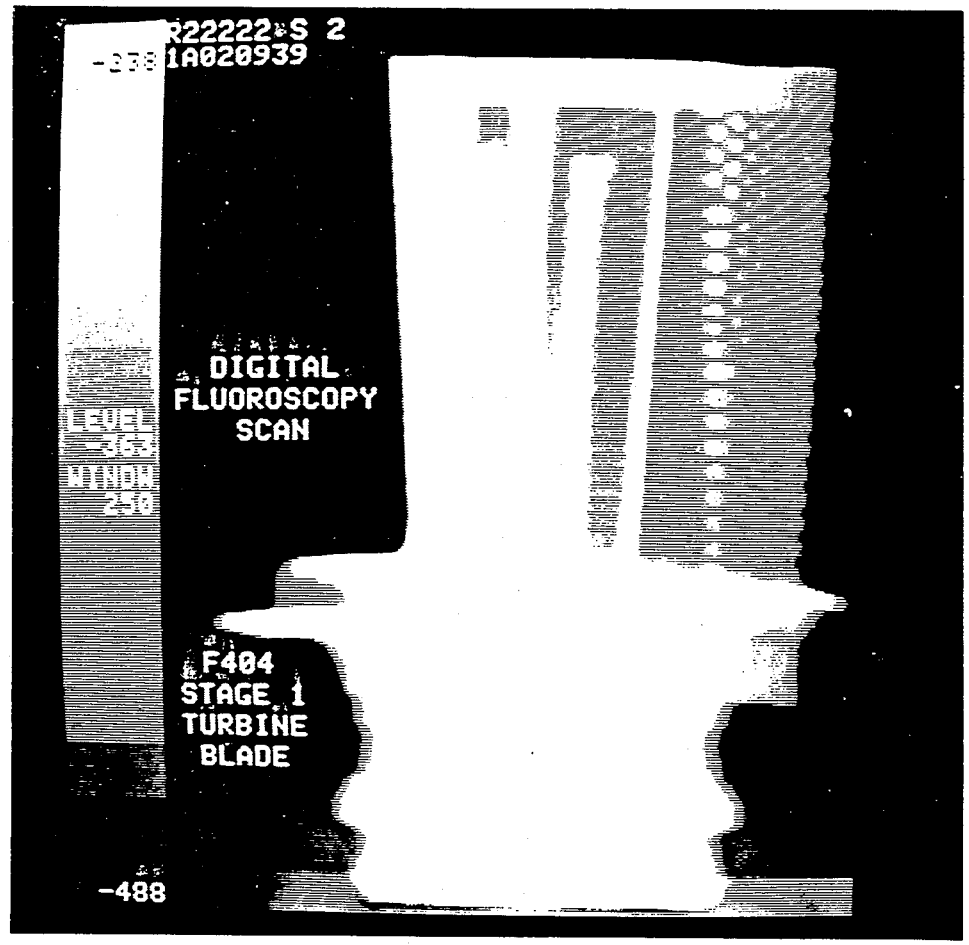

FIG. 15 is a digital fluoroscopy image.

Figure 16:
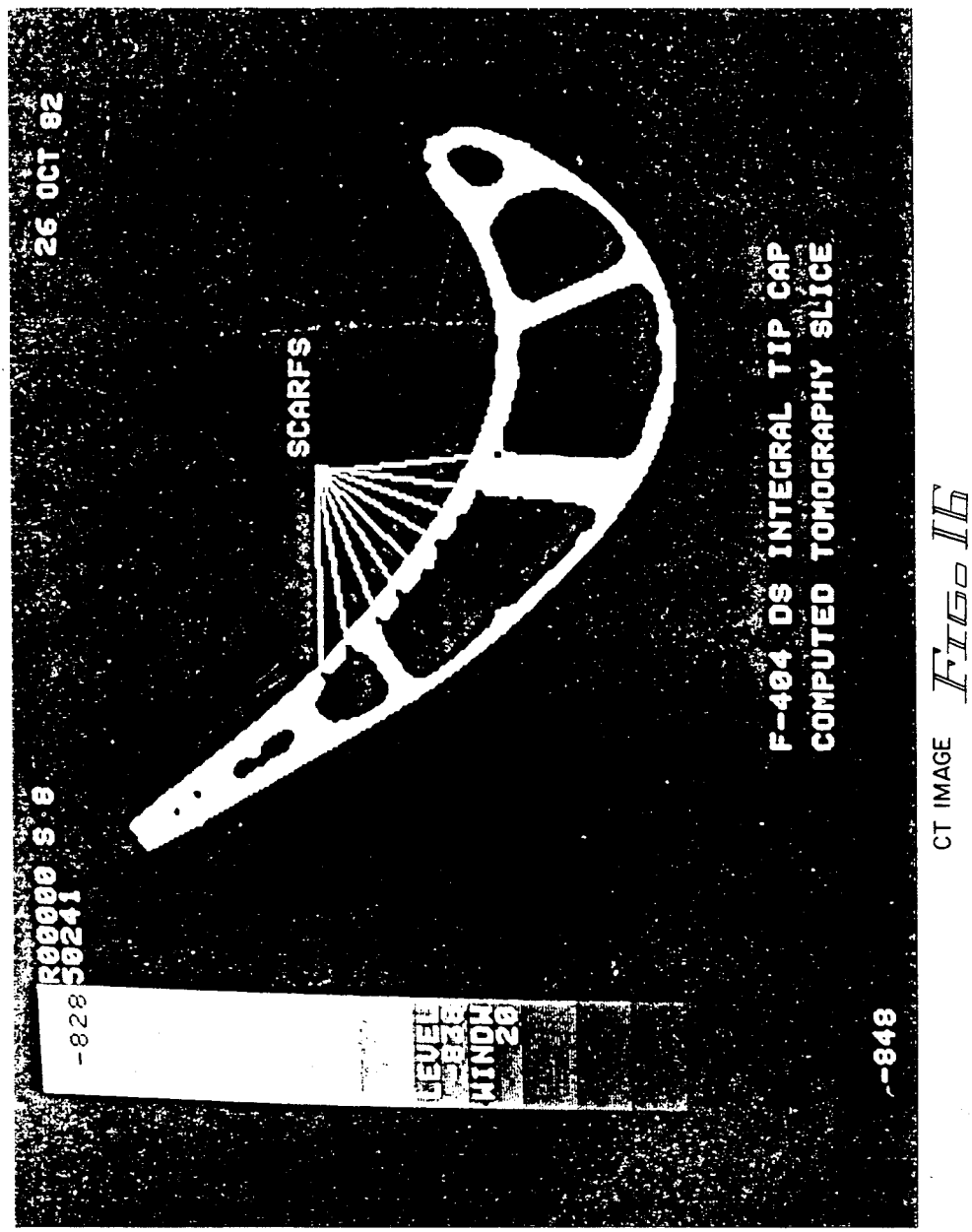

FIG. 16 is a computed tomography image.

Figures 17, 19:
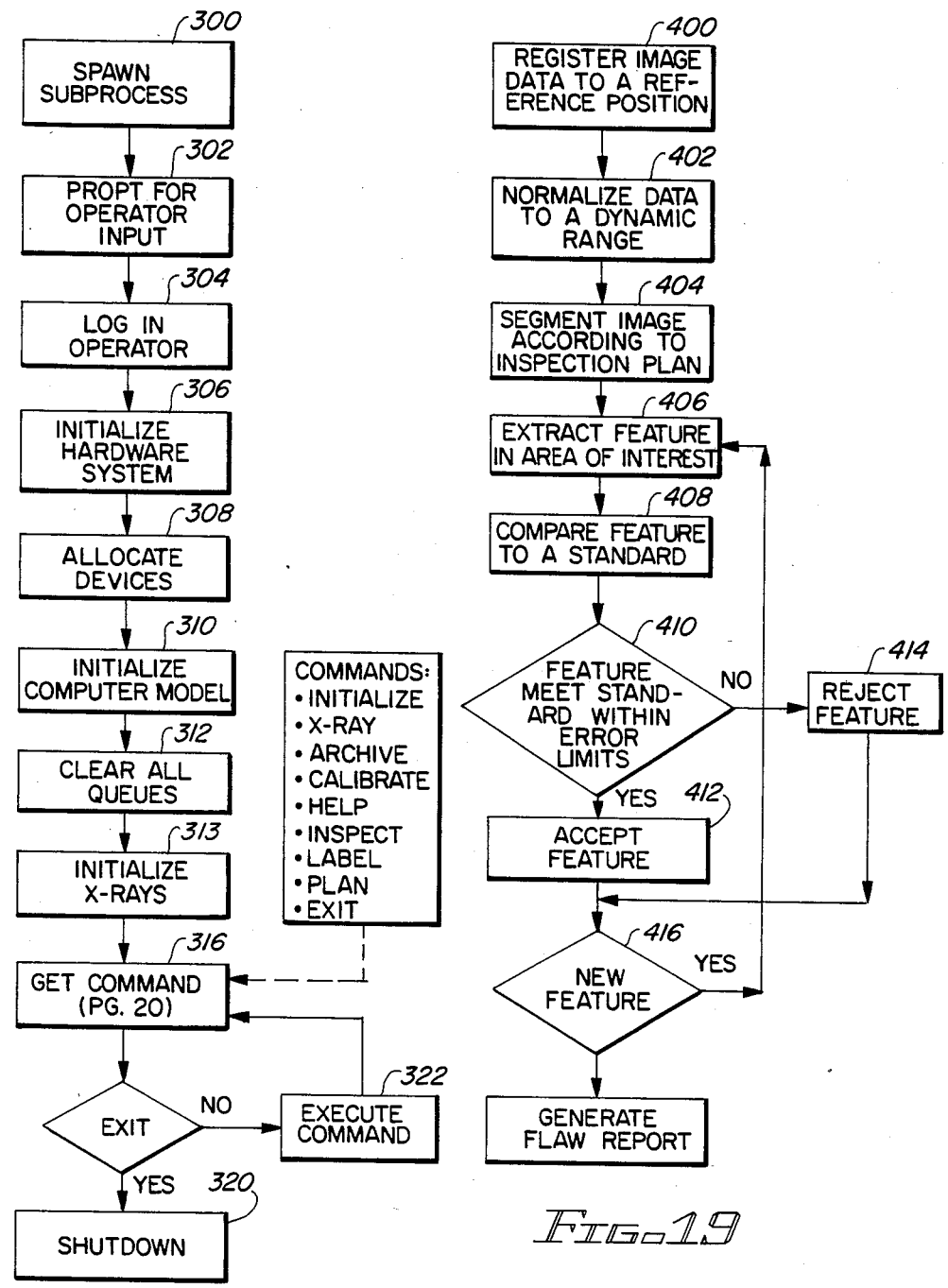

FIG. 17 illustrates a basic flow diagram of the executive software of the present invention.

Figure 18:
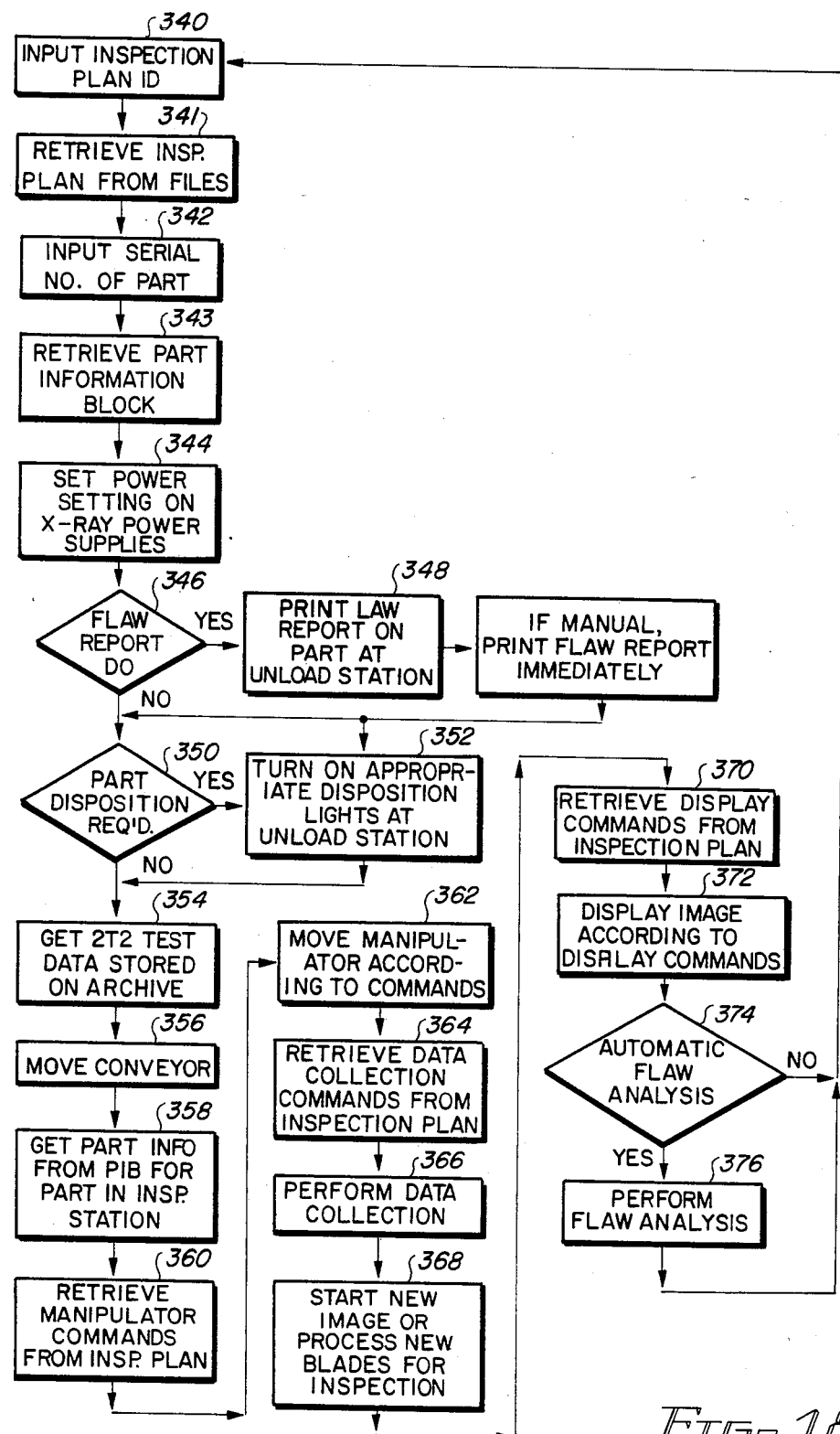

FIG. 18 shows a detailed flow diagram of the inspect command.

FIG. 19 is a block diagram of the automatic flaw analysis.

FIG. 20 is a flow diagram of the archive subprocess.

FIG. 21 shows a diagram of digital fluoroscopy scanning motion.

FIG. 22 is a timing diagram for a digital fluoroscopy scan.

FIG. 23 shows the part envelope and the position of the reference detectors of the linear array detector.

FIG. 24 is the wedge shaped test piece for generating beam hardening data.

Figure 25:
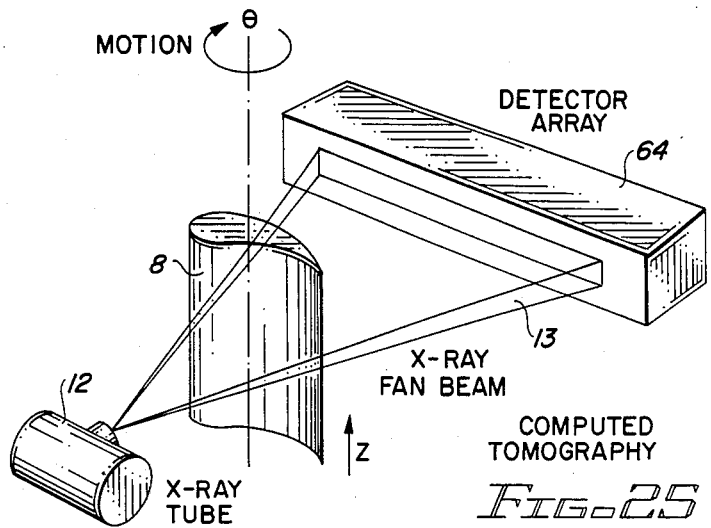

FIG. 25 shows the scanning motion for computed tomography.

Figure 26:
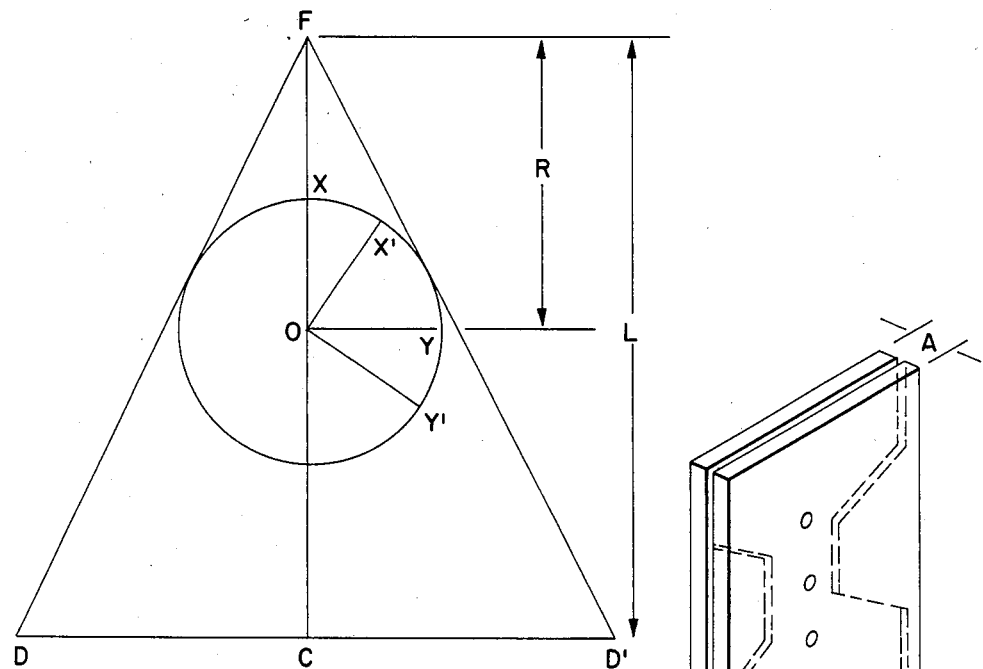

FIG. 26 shows the geometry for a computed tomography scan.

FIG. 27A-D shows a method for computing the center detector position of the linear array detector.

Figure 28:
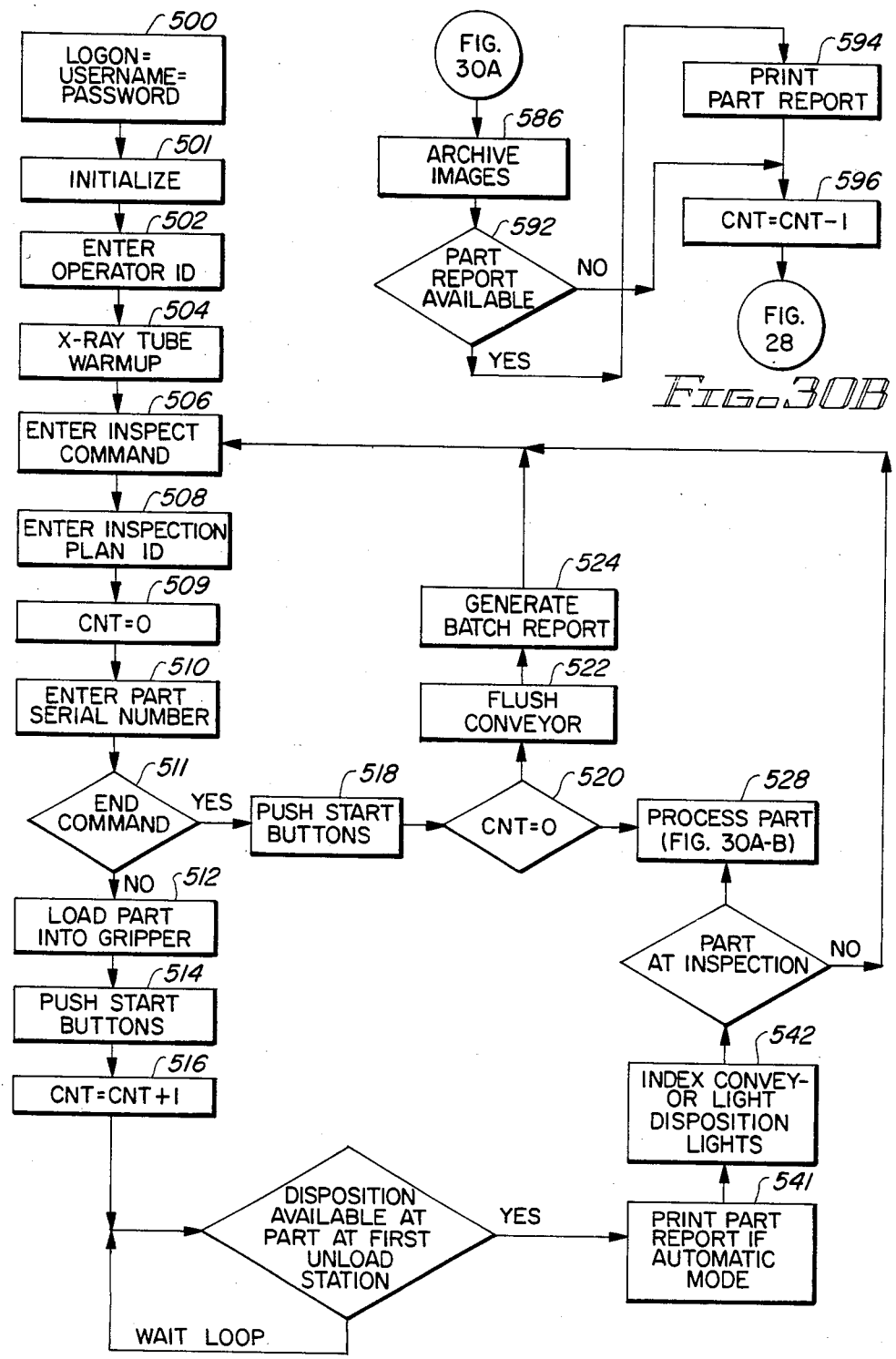

FIG. 28 illustrate a flow diagram for operating the X-ray inspection system.

Figure 29:

FIG. 29 shows loading a part into a gripper on the conveyor.

Figure 30A:
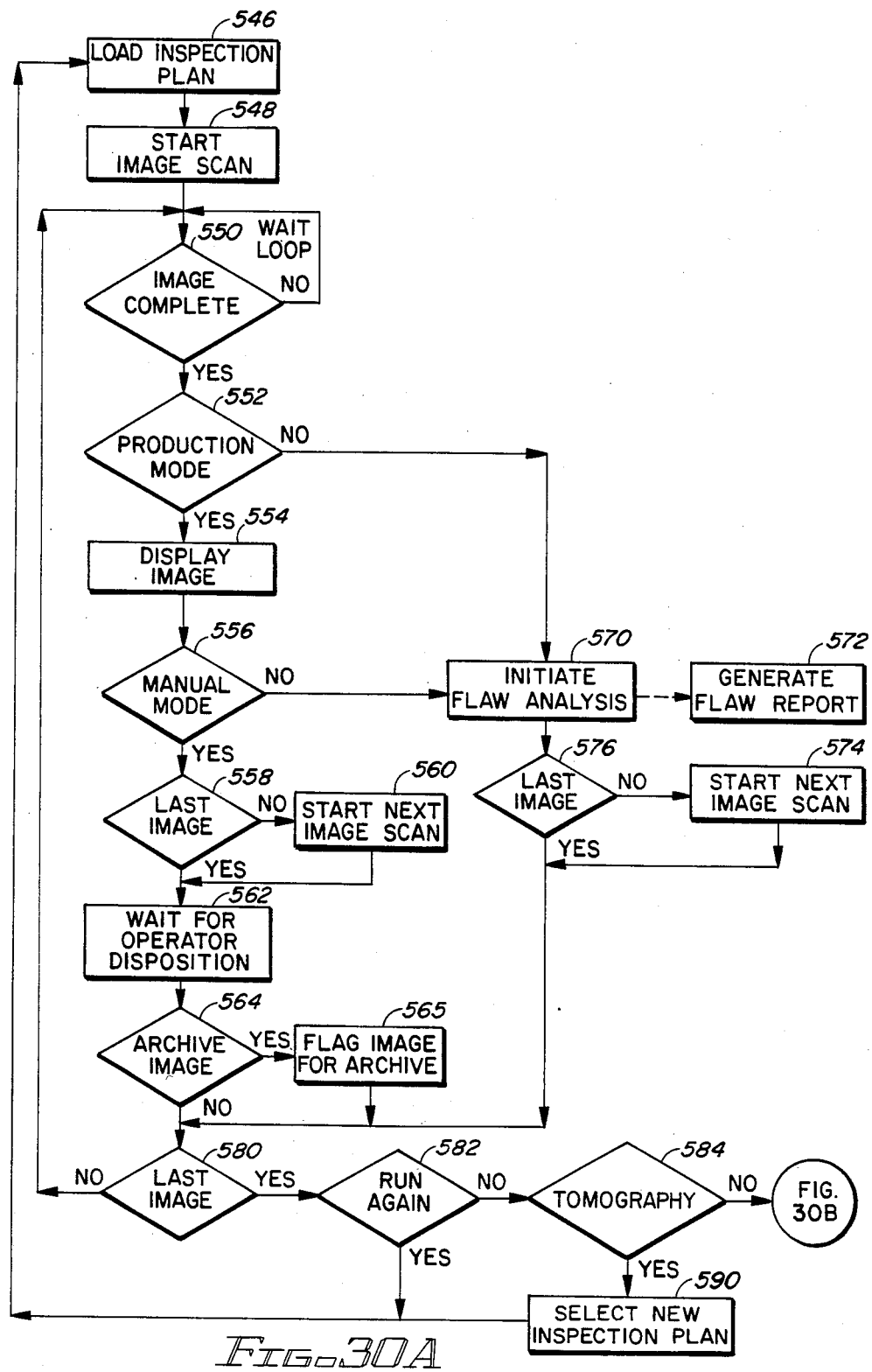

FIG. 30A-B illustrate a flow diagram for processing a part through the X-ray inspection system.

Figure 31:
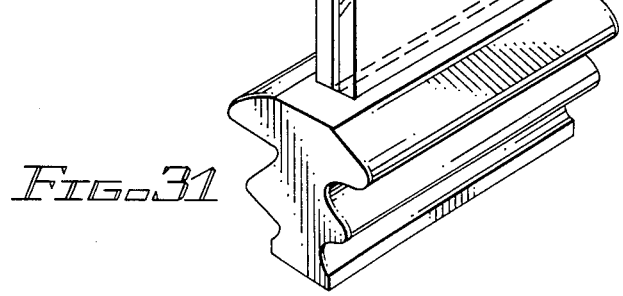
Figure 27A:
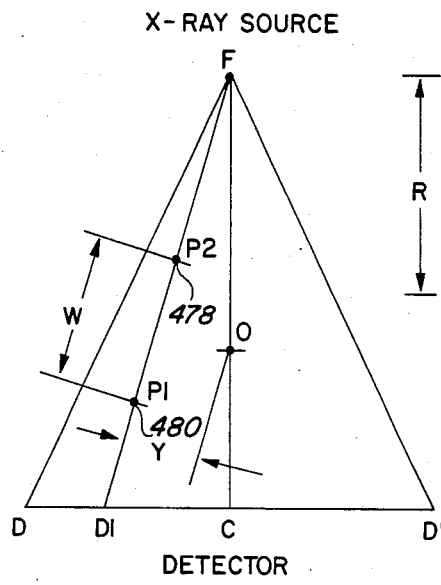
Figure 27B:
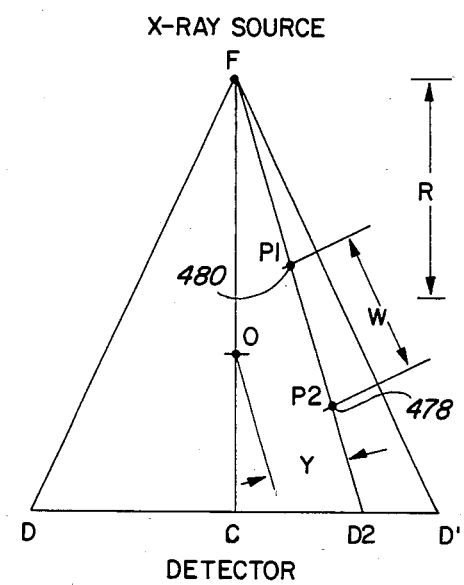
Figure 27C:
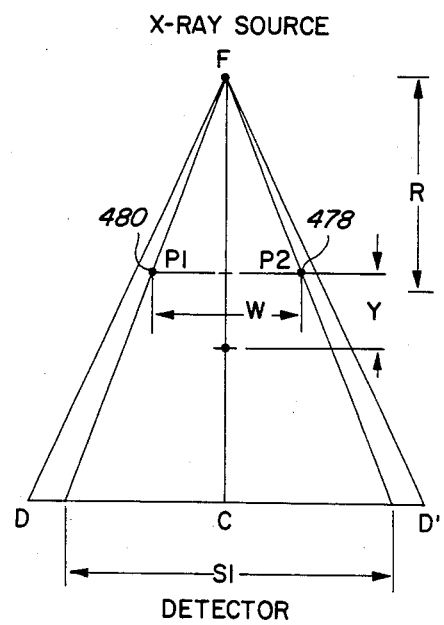
Figure 27D:
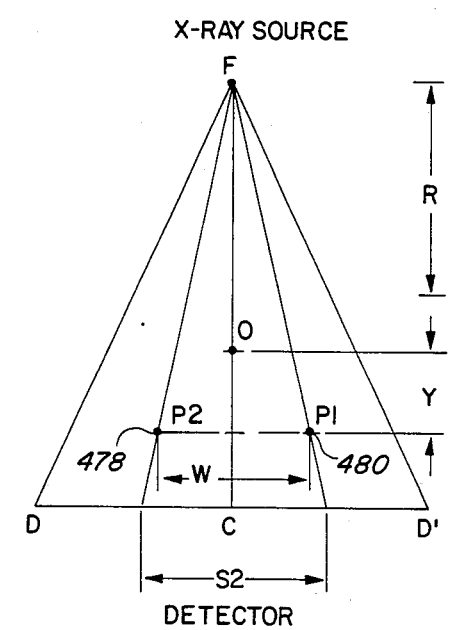

FIG. 31 is a 2-2T test object for calibrating the part images.

FIG. 32 shows the operator console.

FIG. 33 shows a bar coded operation sheet for a TF34 blade.

OUTLINE

1. BACKGROUND

A. Field of the Invention
B. Discussion
2. SUMMARY
3. BRIEF DESCRIPTION OF THE DRAWINGS
4. GENERAL DESCRIPTION
5. X-RAY SOURCE
6. X-RAY DETECTOR
   A. Linear Array Detector
   B. Method of Aligning the Detector
7. PROGRAMMABLE CONTROLLER
8. PART MANIPULATOR
9. INDUSTRIAL CONTROLLER
10. CONVEYOR
11. GRIPPER
12. COMPUTER SYSTEM HARDWARE
13. DATA ACQUISITION SYSTEM
14. COMPUTER SYSTEM SOFTWARE
   A. General Description
   B. Part Information Block
   C. Inspection Plan
   D. Executive Software
   E. Flaw Analysis Subprocess
   F. Image Archive Subprocess
15. OPERATION AND METHOD OF DF SCANNING
16. OPERATION AND METHOD OF CT SCANNING
17. OPERATION
   A. Contrast
   B. Text
   C. Line
   D. Circle
   E. Erase Text
   F. Erase Graph
   G. Manual Measure
   H. Auto Measure
   I. Zoom
   J. Locate
   K. Scroll Up and Scroll Down
18. 2-2T IMAGE QUALITY CHECK
19. BAR CODE READER
20. CONCLUSION

4. GENERAL DESCRIPTION

Figure 1:
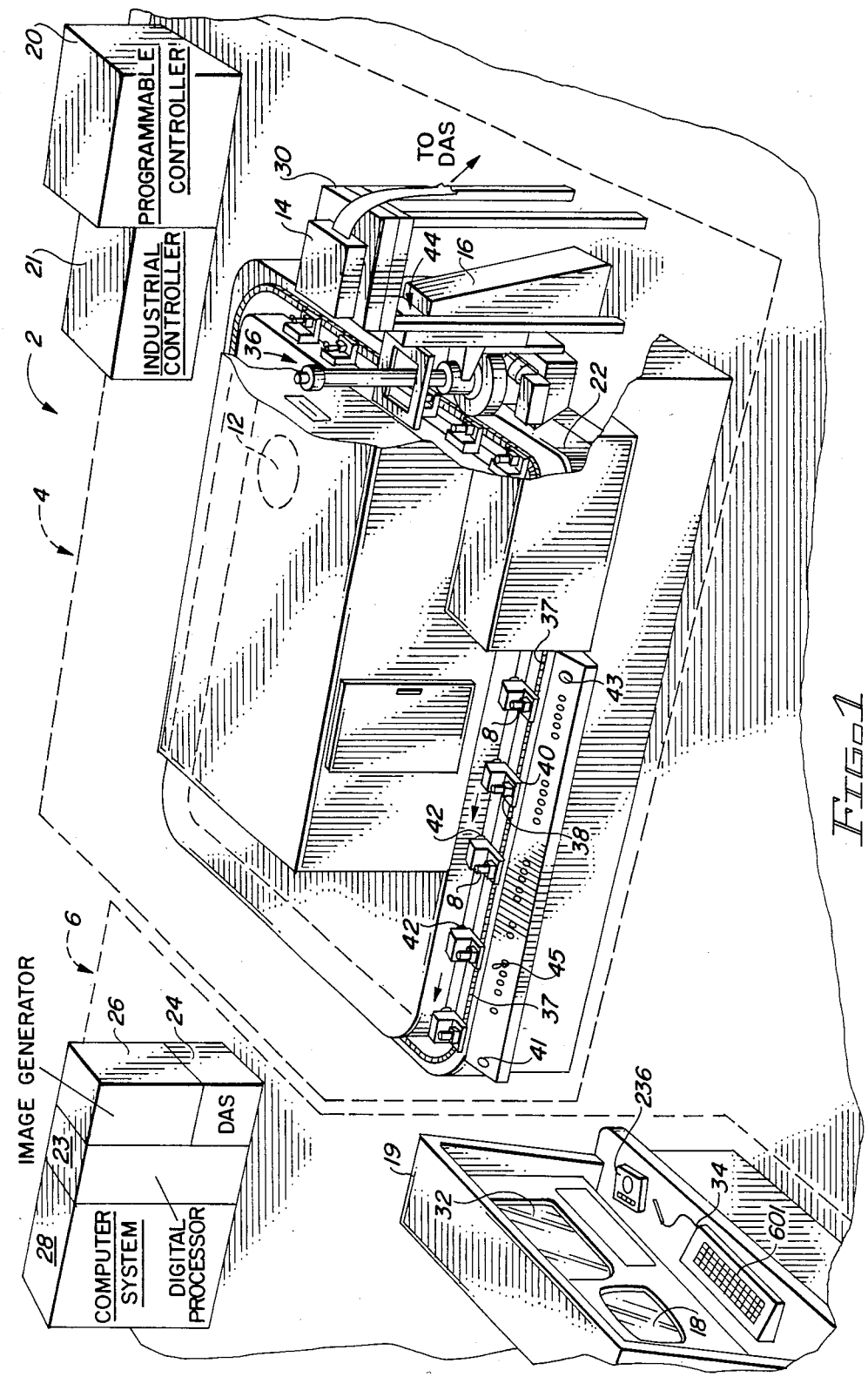
FIG. 1 illustrates the basic components of the X-ray inspection system.

FIG. 1 illustrates the basic components of the X-ray inspection system 2. The X-ray inspection system 2 includes an X-ray machine 4 and an X-ray image system 6. The X-ray machine 4 comprises an X-ray source 12, an X-ray detector 14, a part manipulator 16, programmable controller 20, an industrial controller 21, a six-axis movable platform 30 and a conveyor belt system 22. The X-ray image system 6 includes a data acquisition system 24, an image generation system 26, a computer system 28, an operator console 19, an operator display 18, a keyboard 601, a display procesor 23 a high resolution display 32, and a bar code reader 34.

Figure 2:
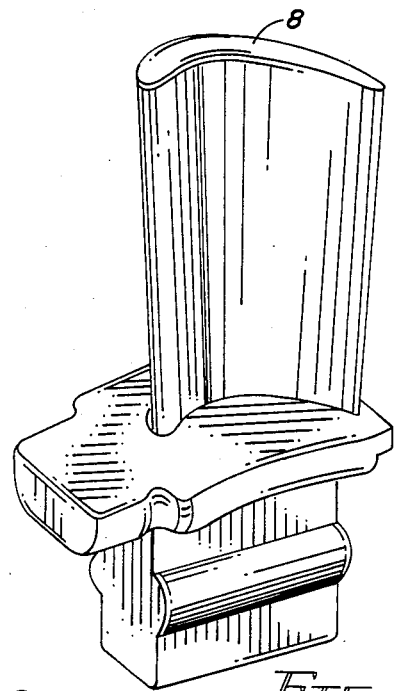
FIG. 2 is an engine turbine blade.

Parts 8, such as aircraft engine blades, are carried into the X-ray machine 4 by conveyor belt system 22. While the present invention is described hereinafter with particular reference to blades, it is to be understood at the outset of the description which follows that it is contemplated that the apparatus and methods in accordance with the present invention may be used to inspect numerous other manufactured parts. These include but are not limited to various parts of turbine engines, such as compressor or turbine blades, vanes, nozzles, thermocouples, etc. FIG. 2 illustrates a typical engine blade. Referring back to FIG. 1, an operator loads a blade 8 into a gripper 38 which is held to the conveyor 22 by a pallet 40 supported on the conveyor 22 system by rollers 42.

The operator informs the X-ray inspection system 2 of the part number of the blade and the type of inspection required. The operator simultaneously presses the start buttons 41 and 43. The conveyor 22 advances the blade 8 as shown in the direction of the arrow through 18 stations or positions to an inspection station 44. The inspection station 44 is inside a lead shielded chamber (shown cut away in FIG. 2). The numerically controlled part manipulator 16 removes the gripper 38 with the blade 8 from the conveyor 22 and positions it in an appropriate path of a directed X-ray beam 36 between the X-ray source 12 and X-ray detector 14.

The X-ray image system 6, following an inspection blade plan, produces a digital fluoroscopy image or a computed tomography image. For digital fluoroscopy images, hereinafter referred to as DF images, the blade 8 is held at a constant angular position and moved by the part manipulator 16 vertically through the X-ray beam. For computed tomography images, hereinafter referred to as CT images, the blade 8 is held at a constant vertical position and rotated by the part manipulator 16 up to 360 degrees. Every 60th of a second the intensity of the transmitted X-rays is collected from 636 horizontal detector elements of the X-ray detector 14 by the data acquisition system 24. The collected data are fed from the data acquisition system 24 to the image generating system 26, where it is normalized for changes in X-ray tube output, channel gain, and sensitivity variations. The data is then corrected for beam hardening. In the case of a DF image in which the blade 8 is scanned vertically, the data is stored on the computer system 28. In the case of CT images, in which the part is rotated, further processing by convolution and back projection for obtaining the CT image is done in the image generator 26. The CT image is then transferred to the computer system 28 for display and storage. After all DF images and CT images are collected by the computer system 28 the part manipulator 16 returns the blade 8 part to the conveyor 36. The conveyor 22 advances, and a blade 8 eventually emerges from the X-ray chamber to the first of three unload stations 46, 48 and 50. The computer system 28 analyzes the DF or CT image for identifying the location of rejectable flaws in the blade. In manual mode, the operator determines the flaw location and measures the flaws. The operator then determines the disposition of the part or if further analysis, such as a CT image is required, an automatic flaw analysis process determines whether the blade is acceptable, rejectable, or requires further inspection. A flaw report is generated and lights on the unload station are activated for notifying the operator of the blade disposition.

The X-ray image system 6 controls part flow, computer task coordination, operator validation and logging, X-ray warmup and logging, blade imaging, data acquisition, flaw detection, quality control plan execution, part image archiving, part flow analysis, and part report generation. In automatic mode, the X-ray image system 6 performs automatic image analysis in real time. The image data for a blade is obtained in real time while the blade is being manipulated.

FIG. 3A-B show a schematic diagram of the conveyor 22 and the lead shielded chamber. The X-ray inspection system processes blades in a sequential fashion, dictated by their physical position on part conveyor 22. The throughput of the X-ray image system is limited by the scan time of the blade and the processing time of the blade. The blade scan time is a function of the physics of x-raying the blade, the data acquisition system 24, the size of the blade, and the type of scan (DF or CT). Blade processing time is a function of the size of the blade image, the processing to be applied to the image, and the number of images for the blade. The X-ray image system processes a blade during the scan time of the blade or the next blade for achieving real time operation.

The X-ray inspection system, operates in either manual or automatic mode. In manual mode, the system allows the operator to make a blade image, display the image, blade disposition, and repeat if necessary. The automatic mode performs automatic flaw detection flaw analysis, and blade disposition.

5. X-RAY SOURCE

FIG. 4 illustrates the electromechanical apparatus of the X-ray machine 4. The X-ray source includes an X-ray control unit 52, an X-ray power supply 54, a 75 KV step up transformer 56, two 210 KV high tension generators 58 and 60, the X-ray tube 12 and an oil cooler (not shown). The line power is fed through the X-ray power supply 54 to the 75 KV step up transformer. Each high tension generator (58 and 60) is fed from the 75 KV step up transformer 56. Each high tension generator applies its potential across the tube to generate a 420 KV potential. 210 KV from generator 58 to the tube and 210 KV from generator 60 to the tube for generating 420 KV accelerating potential in a manner well known in the art.

The X-ray controller 52 regulates beam current, filament current and filament voltage. The X-ray controller 52 has safety interlocking circuitry for shutting the X-ray source 12 off if over temperature, over wattage, or X-ray machine door openings are sensed. Basically, the X-ray controller 52 controls the filament voltage and current, monitors the temperature and flow of cooling oil, shuts the system down if temperature or current exceed predetermined values, and monitors X-ray machine access door openings. The oil cooler draws the heat away from the tungsten target in the X-ray tube. The oil cooler is an oil to air heat exchanger.

A kilovoltage level for the X-ray tube is set manually or is set by the X-ray controller 52 in the X-ray power supply 54 by a D/A convertor circuit in response to commands from the programmable controller 20. For a detailed description of the function of the programmable controller, attention is directed to section 7 of the disclosure. The voltage from the X-ray controller, proportional to the X-ray tube kilovoltage needed by the X-ray tube, drives a servo system in the X-ray power supply 54. The servo system drives a roller in the power supply 54 to an appropriate tap point. To achieve a constant voltage on the X-ray tube, the motor drive which moves the roller in the power supply 54 is disabled. The motor drive servo system is disabled while data are being taken. The servo system has a very long time constant and is underdamped. In response to changing input line voltage conditions, large overcorrection and undercorrection voltage swings occur on the input to the X-ray tube. To minimize the input line variation, a line stabilizing transformer 62 with a harmonic filter on the output is used. The line stabilizing transformer 62 minimizes voltage changes in the input to the X-ray tube. The above steps archive a constant voltage on the X-ray tubes.

Since the X-ray inspection system is developed for a factory environment, throughput is a crucial concern. In order to keep up with production rates, one DF image every 30 seconds is obtained. For an 1800 line image, this requires each line of the image to be acquired in 1/60 second. If desired, the system allows synchronization of data acquisition through the power line frequency and to minimize the effects of noise in the system. For the 420 KVP X-ray tube used in this system, a reasonable signal to noise signal is achieved in 1/60 second. For better results the data from more than one data acquisition can be averaged.

6. X-RAY DETECTOR

A. Linear Array Detector

Referring to FIG. 4, tnere is also shown the scanning apparatus of the X-ray machine 4. The X-ray source 12 generates a directed X-ray beam along the Y-axis through an X-ray source limiter 65 to an X-ray detector 14. The X-ray detector 14 includes a beam collimator 66 which prevents scattered radiation from impinging upon a linear array detector 64. The detector collimator 66 extends in front of the detector to eliminate as much background radiation from the X-ray source as possible. The linear array detector 64 consists of 636 individual detector elements aligned along the horizontal axis X. The detector 14 consists of an ionized chamber X-ray detector including a parallel plate capacitor with gas dielectric along with a high voltage power supply and a charge measuring device. Incident X-rays ionize the dielectric material and the ions which are formed and are swept to the collector plates under the influence of an applied electric field. The measured current is proportional to the incident X-ray flux and is relatively independent of the applied voltage over a wide range of voltages. For a more detailed description of the ionization chamber and X-ray detector array reference is made to U.S. Pat. No. 4,682,964 titled Ionization Detector, issued July 28, 1987, assigned to General Electric Company, the disclosure of which is hereby incorporated by reference.

The detector 14 is assembled in a very precise manner to align the detector collimator and the detector elements exactly with the X-ray beam axis. The method of assembling the detector and collimator is described in U.S. Pat. No. 4,734,988 issued Apr. 5, 1988 titled Method of Aligning a Collimator to a Linear Array X-ray Detector, and assigned to General Electric Company, the disclosure of which is hereby incorporated by reference.

The X-ray detector consists of 600 data channels. In addition to the 600 data channels in the X-ray detector 64, 36 reference channels are provided. There are 18 reference channels on each side of the primary array and separated from it by 220 mils. The reference detectors have two major functions. The first is to take account of fluctuations in the X-ray source in intensity. The reference channels are outside the part envelope and hence have a direct air path to the source. That is, the X-ray source radiation impinges on the reference channels without passing through the blade. Any change in signal level in these channels is related to changes in source intensity. The data channels are normalized to the average value in the reference channel during each data acquisition interval. For a better understanding of the reference detectors, attention is directed to FIG. 23 and its accompanying description which discusses the reference detectors in detail.

The second function of the reference detectors is to account for small differences in the data acquisition interval from cycle to cycle. With the 60 HZ power line as a reference clock 68, this effect is rather small for the most part, though in a factory environment, the power line period can vary by tens of micro seconds from its nominal rate. Variations in the vertical step size for DF data acquisition occur if the 60 HZ clock 68 is used. This causes variable pixel sizes in the image which can cause difficulty in interpretation. Though the effect is rather small, it is sometimes preferable to assure the step size is the same for all steps (e.g. in vertical resolution measurements). The exact size of the increment is not important. It is the fact that the increment is always the same which is important. Therefore, it is useful to use a frequency reference other than the power line frequency 68. In particular, the programmable controller 20 which controls the part manipulator for positioning the part moves with nearly constant velocity. An encoder pulse 70 is generated by the part manipulator every time the blade is moved approximately 5 mils. The encoder pulse 70 is fed to the programmable controller 20 which generates an encoder clock signal 72 which is fed to switch 74. Switch 74 is controlled by the industrial controller 21. The switch 74 allows either the encoder clock 72 or the 60 HZ clock 68 to be applied to the image generator 26 which provides the clock signal to the data acquisition system. In the case where the clock to the data acquisition system is from the encoder clock 72, slight variations in the data acquisition time can also occur. This, of course, causes changes in the amplitude of the reference signal. These changes are accounted for by normalization of the data channels in the X-ray detector with the reference detectors. Thus the reference detectors compensate for any change in signal level from the X-ray source and any changes caused by variations in either the 60 HZ clock 68 or the encoder clock 72.

In order to achieve a spatial resolution on the order of 10 mils the sampling theorem requires measurements based on 5 mil centers. Since all the data across the width of the blade are taken simultaneously by the linear array detector, this requires that the individual detector elements be spaced by 5 mils centers. In order to achieve comparable resolution of the vertical resolution of DF imaging, a resolution of 10 mils with data taken in 5 mils steps is again required. Spatial resolution is achieved by beam collimator 66 which includes two tungsten blocks thick enough to attenuate the incident beam by a factor of 1000 and are spaced 11.5 mils apart in front of the ionization chamber (vertical spacing due to the geometry of the imaging system). The plates of the capacitor which form the detector are spaced apart in order to avoid X-rays directly incident on the collector plates. This spacing determines the detector voltage required to achieve the desired detector response time. Spatial resolution requirements set the spacing of the individual detector elements and the size of vertical movement increment.

The maximum blade size sets the overall dimensions of detector 14, the required number of individual elements, and the number of steps in the vertical scan to complete a full DF image. A typical turbine blade fits in an envelope three inches wide by nine inches high. In a three inch wide detector with elements spaced every 5 mils, 600 detector elements are required. For a better understanding of the configuration of the detector array and the geometry of the X-ray source and X-ray detector described briefly above, attention is directed to FIGS. 21 to 27 of the drawings wherein the geometry for the DF image and CT image are illustrated in detail.

The detector 14 can be moved in any one direction of six axes by platform 30. The platform 30 moves in the X,Y,Z direction or rotates about any one of the axes in a manner well known in the art.

B. Method of Aligning the Detector

Before using the X-ray machine, the linear array detector 64 is aligned with the X-ray source 12. The linear array detector 64 includes 640 individual detector elements aligned along the horizontal axis X. In actual use 600 detector elements are data channels, 36 detector elements are reference channels and 4 channels are reserved. The signal from each channel is fed to the horizontal axis of an oscilloscope for displaying the intensity received by each channel from the X-ray source. The vertical axis on the oscilloscope represents the intensity. If each detector element measures the same intensity from the X-ray source, a constant level appears across the oscilloscope. The beam limiter 65 comprises two tungsten blocks separated from each other by approximately from 50 to 60 mils. A six axis platform 30 moves in the Z, X and Y direction and rotates about each axis for positioning the linear array detector 64. FIG. 5 is a flow diagram illustrating the process for aligning the X-ray detector 14.

First, an unobstructed path between the source and the detector is obtained, block 100. To begin the alignment procedure, the X-ray source beam limiter 65 is open to prevent attenuation on the detector array 64, block 102. The six-axis platform 30 then positions the linear array detector 64 for the maximum signal possible from each detector channel, attempting to have the detector array as horizontal as is possible, block 104. When the maximum signal from each detector channel is achieved, the opening on the X-ray beam limiter is reduced by half, block 106. If the intensity of the X-ray source does not drop, the width of the X-ray source beam limiter 65 is reduced until interference with the signal by limiter 65 is detected by the detector elements, block 108. The limiter 65 is then moved vertically and shifted about the X axis for achieving non-interference from the limiter 65, blocks 110 and 112. Moving the limiter 65 differentially up and down for maximum signal results in the limiter 65 centered symmetrically about the X-ray source beam. The purpose of the beam limiter 65 is to reduce the amount of extraneous radiation that strikes a blade. Reducing the amount of extraneous radiation that strikes the blade reduces the amount of scattered radiation from the blade which enters X-ray dectector 14. The X-ray beam limiter 65 is then fixed in this position, block 114. Since the detector collimator 66 is securely fastened to the X-ray detector 14, the collimator 66 and detector 14 move as one unit. The depth 67 of the collimator 66 in the Y direction is approximately 750 mils. The opening 69 is approximately 12 mils. These dimensions reduce the amount of scattered radiation entering the detector 14. The depth 67 and height 69 of the collimator reduces the angle through which scattered radiation may enter the detector unattenuated. Reducing the amount of scattered radiation entering the detector 14 by increasing the height of the collimator 66 and decreasing the opening 69 produces a higher quality image than previously possible. Increasing the depth 67 and decreasing the opening 69 allows only radiation parallel to the Y axis to enter the detector. The detector 14 and collimator 66 are moved by the six axis platform 30 for producing a maximum signal, block 116. The detector array 64 and X-ray source 12 are now aligned for maximum signal.

One of the most crucial parts of aligning the detector is to make the center of the detector array co-linear with the straight line drawn between the X-ray focal spot through the axis of rotation about the Z axis of the part manipulator stalk. This function is accomplished by rotating a gripper with an extension flange in the X-ray beam. FIG. 6 shows a gripper 39 with an extension flange 75. Referring back to FIG. 4, the center axis of rotation of the gripper 39 is the same as the center axis of rotation of the part manipulator stalk 76. The gripper 39 is securely fastened and centered on the part manipulator stalk 76 by the plunger 86 being forced into a self-centering cavity 90. For a better understanding of the functional cooperation and components of the gripper 39 and part manipulator stalk 76, attention is directed to FIGS. 9A-C.

The oscilloscope trace is adjusted such that the data detectors span the entire oscilloscope face. The gripper 39 is held on the part manipulator stalk 76, and rotated to place the extension flange on one edge of the detector array, and moved up into the X-ray beam 13 so only the extension flange 75 intersects the beam 13 between the X-ray source 12 and the detector 14. The detector channels affected by the intersection of the flange 75 appear on the oscilloscope with a reduction in signal value compared to the majority of the other elements. From the edge of the flange 75 a first edge detector element is accurately determined from the oscilloscope. The gripper 39 is then rotated 180 degrees. A determination of a second measurement edge detector element is made. The linear array detector 64 is moved either right or left to make the first and second edge detector elements have the same relative position from each edge of the oscilloscope screen. This is checked by rotating the gripper 180 degrees, noting the position of the first edge detector, rotating the gripper 180 degrees and noting the second edge detectors position. In this iterative manner, the linear array detector 64 is adjusted so the center of the detector array is nearly coincident with the axis of rotation about the Z axis of the part manipulator.

A precision brass cylinder is then placed in the gripper. The brass cylinder provides a surface to measure the distance from the X-ray source focal point to the center of rotational axis of the part manipulator (Y1) and the distance between the linear array detector 64 and the center of rotational axis of the part manipulator (Y2). With parameters Y1 and Y2 the magnification of the X-ray system is determined. The magnification is equal to (Y1+Y2)/Y1. Aligning the detector prevents scattered radiation from degrading the X-ray images, provides a higher resolution image, and improves signal to noise performance.

7. PROGRAMMABLE CONTROLLER

FIG. 4 illustrates a basic block diagram of the operation of the programmable controller 20 in the present invention. The programmable controller 20 is a computerized numerical controller containing a microcomputer which executes standard numerical control codes in a manner well known to those of ordinary skill in the art. The programmable controller 20 comprises a microcomputer (not shown), a control panel (not shown), an RS232 input port 78, a control input port 80, an encoder pulse output port 72, and M function output ports 82. The programmable controller 20 controls the position and motor drives of the part manipulator 16 through a servo control system including motor drives and shaft encoders 95 and 97. Positioning is both linear and rotary in nature. The programmable controller 20 accepts external inputs (78 and 80) and provides outputs for controlling functions on the X-ray machine. Since the programmable controller 20 is an independent processor, it is capable of being programmed to accomplish tasks. The RS232 input port 78 receives programmable controller 20 programs (or numerical code) from the computer system 28. These programs are written in programmable controller 20 code, and control, for example, the part manipulator 16 or the X-ray controller 52. The control input port 80 receives programmable controller commands from the industrial controller 24 generated by the computer system 28. The programmable controller commands emulate the front panel controls of programmable computer 20, such as enabling the programmable controller to read programs on the RS232 input port, perform a program in memory, and various other commands well known in the art. The programmable computer used by applicants in this invention is a Model SMART ICNC, manufactured by Aerotec, Inc. Accordingly, the programs written for the practice of this invention are in a language suitable for that processor. Briefly the programmable controller 20 commands are:

F Command—speed rate of the part manipulator. This controls the speed of the Z axis and theta axis.

G Command—All axes home. For example, G 62 and G 63 send the Z axis and theta home separately. G 7 sends all axes home.

N Command—Loops in the programmable computer 20 code. N codes are used as sequential references for block or subroutine numbers. Certain N codes allow you to jump, repeat and access special data storage areas.

Z Command—Sends Z axis to a certain position.

D Command—Sends theta to a certain position.

M Command—Provides inputs for controlling functions.

C Command—Continues execution of the programmable computer code.

MO Command—Programmed wait for the Programmable computer 20.

The MO command is used as a handshake between the programmable controller 20 and the computer 28. For example, the computer tells the programmable controller 20 to move the part manipulator stalk 76 to a position and wait. When the programmable controller 20 executes the MO command it waits and raises a line 84 that is sensed by the industrial controller 21. The sensed condition of line 84 is sent to the computer system 28. For a better understanding of the industrial controller 21 and computer system 28, reference is made to FIG. 8 for a detailed description. When the computer system senses the wait condition of programmable controller 20 on line 84, the computer 28 issues a continue command for the programmable controller to continue. This handshaking is used when a blade is inspected. Before a blade is inspected, air reference data is collected by the X-ray image system. The computer must know that the blade has been picked up by the part manipulator 16 and moved into position just below the X-ray beam 13. The computer senses this through the MO line 84. The computer takes the air reference while the part is moving up to this position, and in sensing the MO line, the computer knows where the blade is and then instructs the programmable computer 20 to continue.

The control of the part manipulator 20 and the X-ray source 12 are accomplished by using M commands. The M commands control relays via these output lines. The relays energize various motor drives and solenoids. There are 12 output lines 82 in the programmable controller 20 controlled by M functions. Four output lines control the X-ray source kilovoltage setting. The four lines provide 16 levels of X-ray voltage from 220 KV to 420 KV. One output line turns the X-ray source on or off. One output line disables the motor drive on the variable X-ray power supply 54.

The servo drive motor for the variable X-ray power source is disabled to minimize any X-ray source flux variation caused by the servo system. One output line shorts a current potentiometer to provide maximum current to the X-ray source. During normal operations the X-ray source is run at maximum voltage and current. One output line enables the X-ray safety interlock circuit. One output line opens and closes the X-ray beam limiter 65. One output line activates the gripper plunger 86. One output line enables conveyor indexing.

The programmable controller 20 also generates the encoder clock pulses 72 for activating data collection from the X-ray linear array detector 64. The programmable controller 20 receives encoder pulses 70 from the part manipulator 16. An encoder pulse is generated each time the Z axis moves 0.0394 mils. In a CT scan, the theta axis moves 0.00000463 degrees for every encoder pulse. The programmable computer 20 contains the necessary hardware and logic to count these encoder pulses for producing an encoder clock signal. In the illustrated embodiment, the encoder clock frequency is one timing pulse for approximately 5 mils of movement in the Z axis or 0.24 degrees in the theta direction.

Briefly, a scan subprocess in the X-ray computer system software supervises the programmable controller 20 which generates scan motion and timing pulses to the data acquisition system and image generation subsystem. Thus the programmable controller 20 and the data acquisition system are synchronized. The programmable controller 20 is commanded to home the Z axis and the rotation axis and wait. The scan subprocess senses for the completion of the homing. When the programmable controller 20 responds that the homing is complete the scan subsystem knows that the programmable controller 20 is in position to begin the scan. At this point the scan subprocess tells the programmable controller 20 to continue executing its program. At the same time the scan process changes the clock mode from the 60 HZ line reference to the encoder timing clock generated by the programmable controller 20. The scan subprocess commands the data acquisition system to begin collecting data as soon as a clock pulse is received. The number of clock pulses agrees with the number of views that the data acquisition system expects to collect. If fewer clock pulses are generated than the digital acquisition system expects, then the digital acquisition system times out and the scan stops. In this instance the X-ray computer system resets all the hardware and terminates any action on this blade. On completion of a scan, the digital acquisition system returns control to the scan subprocess as soon as the data acquisition is complete. The scan subprocess polls the programmable controller 20 to determine whether a scan is completed. Upon completion of the scan, the programmable controller responds with an appropriate command which notifies the scan subprocess that the scan is completed. The scan subprocess then issues a homing signal to the programmable controller 20. The programmable controller 20 commands the part manipulator 16 to return to a home position and release the blade and enable the conveyor. Finally, the programmable controller 20 signals the scan subsystem that the process is complete.

8. PART MANIPULATOR

FIG. 7 shows a diagram of the part manipulator 16 used in producing DF and CT images. The part manipulator includes a part manipulator stalk 76, part manipulator arms 94 and 92, a ball plunger 86, drive motors and shaft encoders 95 and 97. The part manipulator 16 contains the necessary hardware and logic for moving and controlling the above in accordance with the present invention in a manner well known in the art. The motors 95 and 97 drive two servo controlled axes; one mounted vertically whose direction is perpendicular to the plane of the X-rays and one whose rotation axis is vertical and perpendicular to the plane of the X rays. The motors each have positioning encoders attached to the axis drive shaft which generate encoding pulses on line 70 when an axis is moved. The plunger 86 mounted on the rotary axis provides for the marriage of the gripper 38 to the combination of the rotary and linear axis assembly. The stalk 76 is an aluminum assembly that includes the plunger 86. The pneumatically driven plunger moves up and down. The stalk 76 is slotted at the top such that gripper 38 slides into the correct position above the stalk. The top of the stalk has two flat ground plate arms 94 and 92 into which the gripper slides. Two shoulders on the arms recessed inward engage a gripper wearplate with outward flanges. The pneumatically driven plunger with a tooling ball at the top, engages the gripper 38 to the stalk 76 by pressing the gripper ground plate 96 against the ground plate arms 94 and 92. The ball plunger is forced into a cone shaped opening which centers the gripper 38 on the stalk 76. The part manipulator 16 moves the gripper 38 with blade 8 up and down in the Z axis for a DF scan or rotates the blade 8 about the Z axis for a CT scan. The motion in the Z axis or theta direction is controlled by the programmable controller 20 through command motion lines 88 to the part manipulator 16.

The part manipulator 16 controls three important movements. The first movement is the movement in the Z axis. The second movement corresponds to a rotation about the Z axis. And, the third movement is the forcing of the pneumatic ball plunger 86 into a centering cone 90 in the bottom of the gripper 38. The gripper 38 on the conveyer belt is held loosely in place by a pallet 40. When the gripper 38 and pallet 40 reach the inspection station 44, the gripper 38 slides underneath and between the arms 92 and 94 of the part manipulator 16. The part manipulator 16, under command from the programmable controller 20 forces the pneumatic ball plunger 86 into the centering cone 90 of the gripper 38. This action causes the gripper 38 to align directly on the Z axis with its center of rotation about the Z axis. A gripper base plate 96 is forced against the part manipulator arms 94 and 92 by the plunger 86. The force between the base-plate 96 and arms 94 and 92 firmly hold the gripper in place while the blade 8 is moved in either the Z axis or rotated about the Z axis. The blades do not have to be centered, only the gripper is centered. For CT images, as long as the blade is within approximately a 2½ inch diameter circle with the center being the center of rotation of the Z axis, an accurate CT image will be reconstructed.

Encoders in the part manipulator 16 generate timing pulses 70 which are fed to the programmable controller 20. The timing pulses 70 correspond to a movement in the Z axis or rotation about the Z axis. The programmable controller 20 converts the encoder pulses to an encoder clock signal to drive the data acquisition system. The data acquisition system contains an A/D convertor which converts the data from the detector array at a rate in response to the movement of the part manipulator motors and passes this data to the image generator. In this manner, data is taken at exact increments in the Z direction, or rotation about the Z axis, and eliminates any synchronization problems caused by an external clock. In essence, timing signals are generated by the motion of the manipulator stalk 76 in the Z axis or rotation about the Z axis.

9. INDUSTRIAL CONTROLLER

FIG. 8 illustrates a detailed flow diagram of data transfer between the computer system 28, industrial controller 21 and the programmable controller 20. System 28 communicates to the industrial controller 21 through a bus 132. The industrial controller 21 includes an interface unit 130, bus receiver module 120, bus driver module 122, programmable contrlller module 124, output module 126, and sense module 128. The interface unit 130 includes bus receivers and bus drivers, device address selection, decoder logic, and interrupt vector logic for transferring information between the computer system 28 and the industrial controller modules, in a manner well known in the art. The interface module may take the form of a model MDB-1710 general purpose interface unit as manufactured by MDB Systems. The interface unit 130 converts commands and data from the computer 28 to an internal bus structure 121 for bus receiver module 120. The interface unit 130 also receives data from bus 121 via bus driver module 122. The bus receiver module 120 converts 16 bit data (8 data/8 command) to an internal bus protocol for programmable controller module 124, output module 126 and sense module 128.

The programmable controller module 124 sends commands to the programmable controller 20. The commands include N commands, G commands, Z and D commands, F commands and M commands. These commands control various functions on the programmable controller. A separate line is used to send the continue command. Since the programmable controller 20 is a separate independent microcomputer, the programs for the programmable controller 20 are sent from the computer 28 via an RS232 line connected as a terminal through a terminal output board of the computer 28. For a better understanding of interface between the programmable controller and the computer system attention is directed to FIG. 10 of the drawings.

Output module 126 controls the disposition light display on each of the unload stations. The lights correspond to dispositions of the blade when the blade reaches the unload station. The output module also controls the selection of the 60 HZ or encoder clock for generating timing pulses to the data acquisition system. In addition, the output module 126 controls conveyor movement.

The sense module 128 receives information from various sensors on the X-ray machine. These sensors allow the computer 28 to detect the condition of the X-ray machine.

The following conditions are sensed by the sense module:

Programmable Controller On/Off—Checks whether the line power is switched on in the programmable controller.

Programmable Controller Memory Protect—Switch on the programmable controller which enables writing into the programmable controller memory. If it is in the protect mode, the computer 28 cannot download RS232 data into the programmable controller. The switch is located on the front panel.

Programmable Controller Error Condition—Programmable controller sends a condition as to whether it has received a successful RS232 transmission from the computer 28.

Programmable Controller Z Axis Limit Set—This is an indication of extreme Z axis travel. There is a vertical upper and lower limit of travel on the Z axis. If the Z axis moved any farther, a hard crash into the end of the stationary part of the Z axis stage occurs. Optical sensors in the part manipulator are detected by the programmable controller and the information is put out as a single programmable controller Z axis limit. There is no discrimination by the programmable controller between the top or bottom limit. The Z axis is homed if this error is detected.

Programmable Controller Theta Axis Not Home—This monitors whether the theta axis is homed or not. The theta axis is homed before loading for scanning a blade. At the end of a scan, the part manipulator stalk is above the pallet of the conveyor belt. Z and theta are driven home before bringing the blade down and putting it on the pallet. Theta is homed first because the gripper fits correctly into the pallet only one way. An alignment pin on the gripper fits into a notch in the pallet. The Z axis home is below the surface of the pallet. Therefore, the gripper fits in the pallet correctly only when theta is homed first. If theta is not homed before moving the conveyor the next blade and gripper will not slide into the part manipulator arm and will either ruin the gripper or ruin the part manipulator stalk. Thus, before scanning is indicatd, or indexing can start, theta is homed to allow the gripper to slide into the top of the part manipulator stalk. Therefore, at the end of the scan, theta is homed before the Z axis or the gripper will not fit in the pallet.

Programmable Controller Slide Power Off—Switch on programmable controller which allows the slide power to be off, but all of the electronics remain on. The slide is the Z and theta axes. The switch turns the power amplifiers off that generate the motor drie current for the axes.

Programmable Controller Z Axis Not Home—Monitors whether the Z axis is home. This ensures that the Z axis is in the proper position to allow the conveyor to index, and the next gripper and pallet to slide in without hitting (if theta is properly homed). If the part manipulator stalk is above the conveyor when indexing is initiated, damage to the stalk or conveyor occurs.

Console Power Off—Main power switch for all the relays, relay drivers, and other circuits. It indicates whether power is applied to the electromechanical system.

Interference Light On—Conductive foam over the front of the detector is connected to a circuit that allows protection from rotations of a blade that exceeds a radius that would strike the detector. There is a three inch blade envelope diameter. If a blade exceeds the three inches, it could strike the detector. The conductive foam covers the detector's front and when the blade strikes it, the motion of the part manipulator is stopped.

X-ray Power Off—Monitors a key switch on the front of the X-ray controller that allows the power to be turned on or off.

Focal Spot Selected—Senses whether large or small focal spot is selected. A switch on the X-ray controller has three positions: large spot, no spot, and small spot. A change of the switch cannot be made from large spot to small focal spot without going through the no spot position which cuts off the X-rays. The large focal spot is used for warming up, and the small focal spot is used for images.

X-ray Controller in Manual—Senses whether the X-ray controller is in program or manual operation. Program operation is when the X-ray controller is under automatic control, setting the kilovoltage, turning the X-rays on and disabling the servo drive. Switching to manual allows the operator to run the X-ray machine without any need of computer interaction. It must be in program before operating the X-ray image system.

Manual Clock Control is Off—Senses a condition in which a manual clock pulse is generated. Only used for testing the system.

Pallet Not in Position—Senses whether there is a pallet in the proper position. Functionally, it is a proximity switch which senses the bolt head of one of the idle wheels on the back of the pallet. The steel mass of the bolt head makes the proximity switch change states. It detects whether the pallet has moved during an index.

Part Height Sensor—Senses if a part is to high to fit inside the X-ray chamber. If a retroreflective sensor is switched the conveyor is stopped in mid travel, with power being disabled to the conveyor drive motor.

MO—Programmable controller wait state. Senses that the programmable controller has finished moving the blade and it is waiting for a command to continue.

Part at Inspection Site—An infrared retroreflective sensor over the inspection site to determine whether a part is at the station. Keeps the X-ray system from running an inspection on a nonexistent part.

Part at Unload Site—There are three unload stations on the output side of the conveyor. An infrared retroreflective sensor senses whether a part is in the last of the three stations. If a part is at the last unload station, indexing of the conveyor is inhibited.

Not Operator Index Command—Senses if the conveyor push buttons have been pushed. When the operator pushes the start buttons a flip flop is set. If the conveyor switch is in automatic, the computer senses the flip flop and a conveyor move is initiated.

Keyshake—Senses a hand shaking signal from the error function in the programmable controller. When asserted, this signal states that the programmable controller has disabled external command signals from the computer 28.

Encoder Clock—Senses whether the switch that controls the clock signal between the 60 HZ clock and encoder clock is switched to the encoder clock.

Large Spot—Senses if the X-ray tube is in a large spot configuration for warm-up.

Small Spot—Senses whether the X-ray tube is in a small spot configuration for imaging.

10. CONVEYOR

Referring briefly back to FIG. 3A–B, the conveyor 22 moves the blades through the X-ray machine. The conveyor includes chain 37, drive motors and logic hardware for indexing the blades in a manner known in the art. Operation of the conveyor in either manual or automatic mode is via key switch 45. During computer control the conveyor operates in automatic mode. Conveyor indexing is initiated by the operator pushing the start buttons 41 and 43. The start buttons 41 and .43 are sensed by the industrial controller system 21 by setting of a flip flop read by the sense module of the industrial controller 21. When the flip flop is set on, the controlling software of the computer 28 understands that the operator has pushed the buttons and wants the conveyor to index. The software, through the industrial controller 21, sends the signal to the output module for initiating conveyor advance. The conveyor moves one station. If the operator decides that he is at the end of processing a batch of blades, the operator wands in, with a bar code reader, the END command. The controlling software interprets the command such that there are no more blades to be loaded onto the conveyor. When the operator pushes the buttons for the last blade advance, the system automatically advances the conveyor until the first blade that was loaded is at the inspection station. After each inspection is complete, each blade continues on, incrementally to the first unload station. There are five lights at each unload station. The lights indicate the part disposition (made either by the operator or by the automatic flaw analysis software). The disposition is classified accept, provisional accept, and dispo.

The part dispositions that correspond to the lights are:

ACCEPT—Blade has met all the criteria of the quality control inspection procedure with respect to the drawings.

PY ACCEPT—Category of provisional acceptance. The drawing has not yet been changed to reflect a new inspection criteria. Therefore, the inspection procedure itself cannot be changed. In a provisional manner while the drawing change order is in progress, work can proceed under this provisional acceptance.

DISPO—This disposition is given if the operator does not feel satisfied with his judgment about the viability of some aspect of the inspection, and the operator would like someone else to look at this image. DISPO means that the senior people will review that image and make the final disposition.

11. GRIPPER

FIG. 9A–C show the gripper assembly of the present invention. FIG. 9A illustrates the front view of the gripper 38. The gripper 38 includes a gripper body 140 having a stationary jaw 142, a slidable jaw 144, a gripper base 146, a wear plate 96, an adjustment screw 148, a centering shaft 90 in the shape of a cone, an end plate 150 and a cam 152. In operation, pressing cam 152 inwards causes the slideable jaw 144 to move away from the stationary jaw 142. A blade is inserted between the jaws against the adjustment screw 148. Releasing the pressure upon cam 152 causes a spring 154 to force the slideable jaw 144 towards the stationary jaw 142 for holding the blade between the jaws. The jaws are to be made of a material whose X-ray attenuation properties are low compared to those of the part to be inspected. In doing so, the X-ray system is able to make digital fluoroscopy and computerized tomography images of the part material between the jaws, thereby allowing for whole part inspection capabilities. For a more detailed description of the gripper assembly and its its operation reference is made to U.S. Pat. No. 4,735,451, issued Apr. 5, 1988, titled Method and Device for Gripping Parts in an X-ray Inspection System, assigned to General Electric Company, the disclosure of which is hereby incorporated by reference.

FIG. 9B shows a side view of the gripper inserted onto the stalk 76 of the part manipulator 16. A pneumatic control, when activated, forces the ball plunger 86 into the cone shaped centering shaft 90. The force exerted by the ball plunger 86 on the cone surface 90 forces the gripper 38 to align on its center of rotation. The center of rotation of the gripper 38 coincides with the Z axis. The force on the cone surface 90 by the ball plunger 86 causes any motion in the part manipulator stalk 76 to transfer to the gripper 38 by frictional forces exerted between the gripper wear plate 96 and the part manipulator arms 94 and 92. A movement in the stalk 76 either in the vertical direction (Z axis) or any rotational movement about the vertical axis (theta) causes a corresponding movement in the gripper 38. Essentially, the ball plunger 86 locks the gripper 38 to the part manipulator stalk while centering the gripper about the axis of rotation. An alignment pin 156 positions the gripper 38 on the conveyor pallet.

FIG. 9C shows the gripper assembly 38 inserted into the pallet 40 at the loading station 47. The pallet 40 includes a cardholder 160, a pin 162, a notch 174. an access opening 166 and rollers 42. The pallet is attached to a conveyor chain 37. The chain 37 transport the pallet 40 through the X-ray machine 4. A movement in chain 37 causes a corresponding movement in pallet 40. The chain 37 is attached to a drive motor controlled by the computer 28. The gripper 38 fits loosely into the accessing opening 166. The alignment pin 156 fits into the notch 164 of the pallet 40 for preventing the gripper from rotating in the pallet 40.

To assist the operator in opening the jaws, a gripper tool 170 having an arm 172 facilitates pressing the cam 152. In operation, a gripper tool slot 174 fits over pin 162. The operator presses on a handle 176 towards the gripper 38. A pivotal action around pin 162 forces arm 172 against cam 152. The pivotal action forces cam 152 inward, forcing the jaws apart. A blade is then inserted into the jaws to the end plate 150. The operator releases pressure on the gripper tool arm 176 thus releasing cam 152. In response to releasing cam 152, the jaws are forced together by a spring 154, holding the blade securely in place. The gripper tool 170 is removed. The gripper 38 with a blade securely fastened moves through the X-ray machine on pallet 40. When the gripper 38 reaches the inspection station 44 the part manipulator 16 engages the gripper 38, centers the gripper 38, locks the gripper and lifts the gripper assembly into the X-ray beam. The part manipulator stalk 76 moves through the pallet access opening 166. The part manipulator stalk 76 freely moves the gripper 38 and blade in the vertical direction and rotationally about the vertical axis for DF and CT imaging.

12. COMPUTER SYSTEM HARDWARE

FIG. 10 shows a block diagram of the X-ray image system configuration. The computer 28 used by applicants in this invention is a VAX 11/780, manufactured by Digital Equipment Corporation. Accordingly, the hardware used in combination with the computer for the practice of this invention are in physical and electronic logic states suitable for that computer.

As is readily apparent to any person skilled in the art, other programmable general purpose computers of similar capability may be substituted for the VAX 11/780 and its peripheral equipment.

Computer 28 controls the operation of the system. The computer 28 has sufficient disc space for storing image data from the blades inspected. In the illustration the discs 200 and 202 take the form of 516 megabyte disc drives which may take the form of a model RP07 manufactured by the Digital Equipment Corporation. The computer 28 also contains a tape drive 206 for archiving image data from the discs. Also, the tape drive 206 is used for inputting system tapes and application programs in a manner well known in the art.

Computer 28 transfers image data over a first bus 208 to a high resolution graphics system 23 for displaying image data on the high resolution display 32. A hardcopy unit 212 copies the high resolution images. The computer 28 also transfers data over local area bus 208 to network 210 for other computer systems. A terminal interface 216 contains the necessary hardware and logic for communications between users terminal 218, 220 and the computer 28 in a manner well known in the art. The bus 208 also transfers data between the operator's console 219 and the computer 28.

A second bus 222 transfers data between the computer 28, the industrial controller 21 and the image generator 26. The industrial controller 21 sends commands to the programmable controller 20, controls the conveyor and part disposition lights, and senses various X-ray machine sensors, 224. Programs and data developed for the programmable controller 21 in the computer 28 are transferred to the programmable controller 21 through an RS232 serial input line 226 via one of the RS232 ports on the terminal interface 216. The industrial controller 21 also controls the clock switch 228. The clock switch 228 feeds either the encoder clock signal 72 or 60 HZ clock to the data acquisition system. The programmable controller controls information to the X-ray controller 52 and part manipulator 16. The X-ray controller 52 controls the voltage and current to the X-ray source 12 for radiating the blades in the X-ray machine. The part manipulator 16 manipulates the blades in the X-ray beam and generates encoder pulses fed to the programmable controller 20. The programmable controller 20 converts the encoder pulses to the encoder clock signal 72.

The data acquisition system collects data from the linear array detector 64 which is transferred to the image generator 26. In the particular configuration illustrated, the image processor 26 includes three array processors. The first array processor is a data acquisition processor 230. In the DF mode, the data acquisition processor 230 reads data from the data acquisition system and computes image data which is transferred to computer 28 via bus 222. In the CT mode, data is transferred from the data acquisition processor 230 using the direct memory access capabilities of computer 28 to a second array processor, a CT array processor 232. The CT array processor 232 controls data to and from the image reconstruction processor 234 and performs a convolution operation on the data. The image reconstruction processor 234 computes a back projection image from the CT scan and computes a CT image which is transferred back to the CT array processor 232. The CT array processor 232 transfers the data via bus 222 to the computer 28. The DF or CT image data is stored on discs 200 and 202 or archived on the tape 206.

Basically in a DF scanning mode, only the data acquisition processor 230 is used in computing a DF image. Since the CT mode requires more extensive mathematical manipulations and computations, the CT array processor 232 is used to trasfer data to the image reconstruction processor 234. For a better understanding of the configuration and functional cooperation of the components described briefly above, attention is directed to FIGS. 8 through 12 of the drawings wherein the respective components are illustrated in detail.

The high resolution graphics system 23 includes a graphics processor 204, a 640×512×12 pixel image display 32, a 640×512×4 overlay memory for graphics and text, and a trackball unit 236 with cursor control and programmable function keys. The graphics system 23 displays black and white images with 8 bits of gray scale resolution, or can display color images with 24 bits of color resolution. The graphics system includes a microcomputer, bus receivers, bus drivers, clocks, video circuits, and hardware logic for transmitting data between the computer 28, the high resolution display 32, and trackball unit 236 in a manner well known in the art.

The graphics system 23 performs various functions, such as, contrast manipulation, image measurement, and image zoom. It zooms instantly up to 16X, uses the cursor and function keys on the trackball to measure features on the screen, to add text annotation, to add graphical annotation, to draw lines, and to draw circles. If a flaw in a blade is detected, the flaw can be circled, measured and analyzed. A hard copy unit 212 saves image data from the high resolution display 32 for the operator in a more permanent form. The graphics display system as used by applicants is a model 3400 made by the Lexidata Corporation.

13. DATA ACQUISITION SYSTEM

FIG. 11A-D illustrate the detailed description of the data acquisition system. The data acquisition system includes charge to voltage units 251, a floating point amplifier unit 260, and an analog digital unit 255. FIG. 11A shows the sampling circuit for each individual data channel on the linear array detector. The current generated in response to X-rays impinging on the linear array detector charge-up one side of capacitor 250. A FET switch 252 is connected to a multiplexor 254, which is connected to operational amplifier 256 which has a feedback capacitor 258. Each detector channel will have a similar circuit as shown in FIG. 11A. In FIG. 11B there is illustrated charge to voltage units 251. Each charge to voltage unit converts 32 data channels. The 32 channels of the charge to voltage unit times 20 units equals 640 data channels. The twenty outputs of the charge to voltage units are fed to the floating point amplifier card unit 260. The floating amplifier unit 260 receives the inputs from the charge to voltage units.

The voltage on the input of the floating point amplifier is amplified through one of the amplifiers 264, 266 or 268. A comparing logic circuit 270 compares the level of the input voltage and determines whether to connect amplifier 264, 266, or amplifier 268 to the output. Basically, the floating point amplifier is an auto gain system in which the stages of the gain are 1, 8 or 64. Depending upon the range of the input signal the floating point amplifier will amplify this signal by a different gain. If the input voltage is within the minimum range, the floating point amplifier applies the highest gain to the signal. If it is in the medium range it applies the medium gain to the input signal and if the input is in the high range it applies the low gain to the input signal. The output from the floating amplifier card is fed to an A to D convertor, which converts the input analog voltage to a corresponding digital voltage. The timing and control signals come from the 60 HZ or encoder clock as previously mentioned before to convert the voltage from the floating point amplifier unit. The reason for the floating point amplifier is to increase the convesion speed of the analog to digital converter by converting only to a 14 bit digital signal. With the floating point amplifier, 16 bits of precision are not required and 14 bits of precision are sufficient to measure the signal from the linear array detector card.

14. COMPUTER SYSTEM SOFTWARE

The computer utilized by applicants in this invention is a VAX 11/780 manufactured by Digital Equipment Corporation. Accordingly, the programs written for the practice of this invention are in a language suitable for that computer. The array processors used by the applicants in this invention are two model AP-400 array processors and a model IP-300 modular image processor manufactured by the Analogic Corporation. Accordingly, the programs written for the practice of this invention using the Analogic array processors are in a language suitable for those array processors.

As is readily apparent to any person skilled in the art, other programmable general purpose computers and array processors of similar capability may be substituted for the VAX 11/780 and the Analogic array processors. Consequently, other programming languages may be used in such other machines.

A description of the program set forth, herein, were written in Fortran IV for the VAX 11/780 and basic assembler language for the Analogic array processors. Fortran IV is a higher level language extensively utilized in general purpose computers. The Analogic basic assembler language is utilized for their brand of array processors Various types of programs were supplied by the Digital Equipment Corporation with the purchase of the Digital Equipment hardware, and various types of programs were supplied by Analogic with the purchase of Analogic hardware. These programs are readily available and will not be described herein.

Various systems programs provide, as is well known, various routines for supervising the sequence of other programs by the computer. In addition, the system programs handle routine input and output tasks, assignments of priorities, and so forth. Diagnostics, as their name implies, are hardware test programs. Their function is to exercise the various hardware devices for test purposes. Such tests provide information useful in locating and correcting hardware malfunction. Utility programs used herein involve routines for such tasks as disc to disc copying and tape to disc copying, and so forth. As would be appreciated by any person skilled in the art of real-time programming, programs for the above tasks may be easily written in obvious terms. Accordingly, no further description of the above programs will be given.

The major software system remaining is the executive software for the X-ray inspection system, the data acquisition subprocess, the automatic image processing, automatic flaw detection, and automatic archiving. The object code for the X-ray executive software, the data acquisition subprocess, the automatic image subprocess/ the automatic flaw detection, and the automatic archiving are set forth in object code in the appendix. In order to use the object code, it is only necessary that the code be installed on an identical system and run.

A. General Description

The software for the X-ray image system includes programs for directing a real time executive system which provides an environment for image processing, flaw analysis, and inspection plan execution. The real-time system is controlled by an executive software which starts tasks, monitors tasks, checks error conditions, initializes the system, controls subsystems, and interfaces to the operator. Referring to FIG. 12, there are shown the four major processes which are spawned as independent processes under supervision of the executive system 280. These are data acquisition subprocess 282, automatic image processing 284, automatic flaw analysis 286 and automatic archiving 288. These subprocesses run in parallel to provide a real-time environment. While data are acquired for one image, data acquired previously for another blade are displayed to an operator for decision making purposes. At the same time, automatic image processing and flaw analyses are performed on the data acquired previously. Utilization of the overhead time in mechanically positioning the blade, or in operator decision making, or in flaw analysis allows the system to process blades in a real time environment.

The executive software performs blade flow/computer task coordination, operator validation and logging, X-ray warmup and logging, data acquisition and part manipulation, DF scan and CT scan inspection capability, quality control plan execution, part image archiving, part flow analysis and part report generation.

Under blade flow/computer task coordination, the executive software manipulates a model of the physical conveyor system. FIG. 13 is a diagram of the physical conveyor with the 25 stations. The load station 47 is a station where the turbine blades are loaded on the conveyor pallet 40. The wait state corresponds to slots on the conveyor 22 where the turbine blades are waiting for action. The inspection station 44 on the conveyor is where the turbine blade is manipulated. and placed in front of the X-ray beam for inspection. The analysis and report states on the conveyor is where data are analyzed for the turbine blade inspected. A blade report from the executive must be available for a turbine blade about to enter the unload station 46 because the disposition lights must be illuminated when the blade enters the first unload station 46. There are two overflow unload stations 48 and 50. The conveyor 22 does not move if a blade is in station 50 because the operator must interact with the conveyor to remove the blade.

Referring to FIG. 14, there is shown a computer model of the physical conveyor 36. The computer model begins with a load slot 47 on the conveyor. When the operator types in a part serial number, the computer model enters the serial number for the part number at the load station. The I.D. slots on the computer conveyor model are where the parts are waiting to be scanned. There are 16 slots corresponding to the wait states on the computer conveyor model. The inspection slot 44 on the computer conveyor model is where inspection and scanning of the turbine blade occurs. S1 through S4 correspond to the analysis an report states of the physical conveyor of FIG. 8. In these slots, the executive software is processing the data for flaws and determining the disposition for each turbine blade. When the turbine blade reaches S4, the executive must complete all the dispositions and reports for this particular turbine blade. If a turbine blade reaches this slot without a disposition or a flaw report being generated, the executive does not allow further entering of new turbine blades into the load station until the disposition of the blade is completed. U1 corresponds to the first unload station 46 in which the executive must illuminate the disposition lights for blade disposition. U2 corresponds to the first overflow position and U3 corresponds to the last overflow station 48. If a turbine blade reaches the U3 slot and the operator has not removed the turbine blade, the executive will not move the conveyor with a turbine blade in the slot.

B. Part Information Block

Each turbine blade is associated with a part information block in the executive. The part information block contains all information about a blade in the system. Information is added to the part information block as the part enters the system, and more information is added at each conveyor state until the part arrives at the unload station. Each part information block is associated with a slot on the conveyor. Thus, the executive system at all times knows where each turbine blade is located and the information for each blade. Appendix B illustrate the format for the part information block associated with each turbine blade in the computer model.

The part information block is a repository of information for images generated for the part. It is a buffer in memory that is accessible by all of the subprocesses. When a part is first loaded on the machine, the executive software accesses the part information block for entering all of the information from the operator and from the inspection plan. As the image is generated and analyzed, the part information block is updated with the various parameters generated from the flaw analysis reports. Before the part is indexed to the unload station, the part information block is accessed for the part disposition. The part information block includes two sections. The first section describes the part in general, and the second section describes each individual image that is generated for that part.

Referring to Appendix B, the following are explanations of the part information block parameters:

Part Serial Number—part serial number for the part entered in by the operator.

Part Date—date that the part is loaded onto the machine.

Operator Identification Code—operator ID that is entered when the operator logs onto the computer.

Manufacturing Operation Number—defined on the manufacturing operation sheet and is the manufacturing operation number to be performed on this part.

Archive Tape Label Number—defines the archive tape this image is placed in if the image is archived. It is the tape identification number.

Dispo Tape Label Number—identifier for a dispo tape in case the part is given a dispo disposition. It identifies the magnetic tape the image will later be archived on.

Backup Trigger Flag—identifies whether the image is archived or placed on a dispo tape.

Name of Reference Gauge—file identifier for the most current 2-2T image that has been run on the machine.

Quality Control Extension Plan I.D.—inspection plan identification number that is entered by the operator.

Inspection Plan Download Flag—tells the system whether or not to down load the manipulation command to the numeric controller each time a part is run or only on the first part in a batch.

Load Time for the Part—actual time the part is loaded onto the machine.

Time to Start Part Scan—time the part scan began.

Time to End Part Scan—time the part scan ended.

Time of Start Part Analysis—manual mode when the image is displayed or in automatic processing mode when the image is sent to the automatic flaw analysis software subprocess.

Time of End of Part Analysis—operator enters a disposition and the display process is finished for that part or the automatic processing is finished for that part. These two numbers show the length of time the computer takes to do a flaw analysis for the part.

Reinspect QC Plan I.D.—name or identifier for the reinspection plan. The option to do a reinspect is called the tomography option.

Part Disposition—part disposition after inspection.

Reinspect Flag—if part was reinspected.

Number of Images in the Main Plan—number of images requested to be generated by the inspection plan.

Number of Images in the Reinspect Plan—number of images that are requested by the reinspect plan identified within the original inspection plan.

Actual Number Images from Main—actual number of images generated by main inspection plan.

Actual Number of Reinspect Images—actual number of images generated by reinspection.

Automatic Flaw Report—report name generated by the automatic flaw subprocess.

Manual Flaw Report—flaw report that is generated from the information obtained from the operator reviewing the image as opposed to the automatic flaw analysis subprocess.

Spare Part Flaw—first four bits are used to flag whether the main inspection plan is an automatic or manual inspection plan. The next four bits, bits 5 through 8, define whether the reinspect plan is an automatic or manual inspection plan, and bits 9 through 12 are flags to tell whether the automatic flaw report has been generated since that is done asynchronously. The next two parameters are the memory size of the buffer.

The next parameters are generated for each image processed.

Image Name—file name for this image.

Plan Name—main inspection plan or the reinspection plan that generated this image.

Image Disposition—disposition determined for this image.

Image Archive Status—determines whether or not this image is selected to be archived.

Image Type File Extension—file extension that was selected by the type parameter in the inspection plan.

Time of Start Image Scan—time the scan for that image began.

Time of End Image Scan—manipulation scan for the image ended.

Start Auto Analysis—time automatic flaw analysis began.

END Auto Analysis—time automatic flaw analysis ended.

Start Manual Analysis—time manual analysis began.

End Manual Analysis—time manual analysis ended.

C. Inspection Plan

The needs of a factory automated system require a methodology for instructing the X-ray image system how to manipulate parts, acquire data, and compute the presence or absence of a flaw. This is accomplished with an inspection plan which is segmented for convenience into portions for controlling manipulation of the part, acquisition of the data, automatic image processing and decision making, display of images to an operator, acceptance of operators decisions about the image, and generation of reports. The inspection plan is parameterized so that changes in settings or parameter may be accomplished by changing a few numeric values in a standardized format or by using macro instructions, which call upon a large sequence of image processing operators. The inspection plan is readily altered by using a standard word processing editor, because of the provisions of higher language elements.

When the executive software is examining a part, an associated inspection plan is used. This plan is the heart of the system and defines parameters used in the turbine blade manipulation, data collection, display formatting and flaw analysis. The inspection plan includes a segment, parameter, group, output plan, and input plan. A segment is an inspection description for a single image of the blade. A parameter defines a value within a segment used when inspecting the blade. A group of parameters within a segment is related to a specific function. An output plan is a file where the newly defined inspection description for a part scan is saved during a plan generation. An input plan is a current plan whose inspection descriptions are being used as a template for the development of the output plan. The inspection plan is divided into self-contained divisions, each of which contains all the information required for generating and inspecting a single image of a blade. These sions are called segments; hence, each segment is a single image inspection plan.

In an inspection plan, groups define the beginning of related parameters within a segment. A group includes a common group, a manipulator group, a data collection group, and a display group. The common groups are parameters related to all segments of a plan. Manipulator groups are the parameters which control motion of a turbine blade during data collection while at the inspection slot. A data collection group includes related parameters required for data acquisition. The display group includes control format commands for the image data on the graphics display. An inspection plan consists of common manipulator, data collection and display groups of parameter specification lines. Each line of the inspection plan contains at most three fields. Field one is for the keyword which is the name of value which is used by the executive software to do something, field two is the value associated with the keyword, and field three is for comments to describe the pertinent facts involving the plan. Referring to Appendix C, there is illustrated an inspection plan for a F404 turbine blade.

Each inspection plan descriptor line of Appendix C is explained in detail.

SEGMENT X END PLAN: The SEGMENT and END_PLAN segment tokens segment information relevant to a specific set of images. END_PLAN signifies physical end of the inspection plan. There is not an END_PLAN at the end of each segment. Each image segment includes MANIPULATOR, DATA COLLECTION and DISPLAY sections.

COMMON: The COMMON; section token locates the common section of the inspection plan. This section includes items that are common to all segments of the inspection plan for a blade. Hence, this section will occur only once in an inspection plan, regardless of the number of segments.

2-2T—The 2-2T parameter is the name of the inspection plan used when inspecting the 2-2T gauge.

DRAWING—The DRAWING parameter is the drawing number of the blade being inspected.

REV—The REV parameter is the revision number of the drawing for the blade being inspected.

OPERATION—The OPERATION parameter is the manufacturing operation number for the blade being inspected.

DOWNLOAD—The DOWNLOAD parameter determines whether the inspection plan MANIPULATOR parameters are downloaded to the programmable controller each time a blade is inspected or only for the first blade inspected.

REINSPECT—The REINSPECT parameter is the name of the inspection plan used for the tomography option. This plan is usually separate and different than the inspection plan for the blade being inspected.

MANIPULATOR: The MANIPULATOR section token is used to locate the manipulator section of the inspection plan file. This section contains information about the physical manipulation of the blade.

MODE—The MODE token informs the system whether the following image is in a digital fluoroscopy (DF) or a computed tomography (CT) mode. In Appendix C, MODE specifies a CT image.

Z_START—The Z_START parameter specifies the initial starting height of part manipulator stalk for making the image. The value corresponds to the number of counts on the 1000 line Z axis encoder it takes to reach the desired height for the scan. One count is two microns in length. The upper limit is 405000 counts, the lower limit is 30000 counts. The Z_START places the blade below the X-ray beam. In the above example, Z_START specifies that the scan should commence at 220000 counts from the pallet Z axis home position.

D_START—The D_START parameter specifies the initial starting rotation of the manipulator for making the image. The value corresponds to the number of counts on the 1000 line theta encoder it takes to reach the desired rotation for the scan. There are 21600 steps to 360 degrees rotation. Rotation may be positive (counter-clockwise) or negative (clockwise). As an example, for D_START to commence a scan at 90 degrees clockwise, D_START equals −54000 counts.

CT_HEIGHT—The CT_HEIGHT parameter specifies the height at which the CT slice is taken. Typically, the value is determined by using the locate function from the display. The upper limit is 405000 counts, the lower limit is 30000 counts.

CT height is the number of vertical axis counts, one micron per count, to which the CT slice image is made. The Z height in the CT scan is that point at which the blade can be moved without getting it in the way of the beam while air reference data is being taken. There are two heights for CT and only one for DF.

CT_WIDTH—The CT_WIDTH is the number of pixels that are obtained in every projection (view) for reconstructing an image. In the image reconstuction processor, a reconstruction is based on 512 individual data points; if there are 512 detectors elements, there is a one to one mapping of data points in detectors. If there are 600 detectors, the detectors are interpolated down to 512. If there were 320 detectors, they would be interpolated up to 512.

TRAVEL—The TRAVEL parameter specifies the number of steps of vertical motion for DF scans or rotational motion for CT scans. For the DF mode, travel is calculated:

TRAVEL—((VIEWS/IMAGE) * INCREMENT * 2)+240

For the CT mode travel is defined as:

TRAVEL+216000 (360 degrees)

An example for a DF scan with (VIEWS/IMAGE)=512 and INCREMENT=60 results in a TRAVEL of 61680.

INCREMENT—The INCREMENT parameter specifies the number of steps to traverse in 1/60 of a second. In DF mode this is 60 counts. In CT mode this is 144 counts for 1500 views and 72 counts for 750 views.

CULLS—The CULLS parameter specifies the number of detector readings to throw away due to the time necessary for the part manipulator stalk to accelerate to a constant velocity. Appendix C specifies that thirty (30) detector reading are ignored before saving the image data.

KV—The KV parameter specifies kilovoltage setting of the X-rays, a two digit value from 1 to 16 with 1 being equivalent to 220 KV and 16 being equivalent to 420 KV.

MA—The MA paramter determines whether the milliampere (MA) potentiometer on the KV controller is manually set (1) or automatically set to the maximum (0). Normally this setting is at maximum (0).

INTEGRATIONS—The INTEGRATIONS parameter specifies the number of detector readings that are being averaged together for producing one raster line of image data. Allowable integrations are 1,2,4,5,10 for DF's and 4,8,10 for CT's.

DATA COLLECTION: The DATA COLLECTION section token locates the data collection section of the inspection plan file. This section contains information about data acquisition parameters.

MODE—The MODE token informs the system whether the following image is in a digital fluoroscopy (DF) or computed tomography (CT) mode. In Appendix C, MODE specifies a CT image.

VIEWS_PER_IMAGE—The VIEWS_PER_IMAGE parameter specifies the number of detector readings requested to produce an image. Approximately 212 views are required to scan one inch in DF mode. In CT mode the number of views must be a whole divisor of 216000 in order to insure 360 degrees of rotation exactly.

DESCRIPTION—The DESCRIPTION value records some of the pertinent descriptive information about a scan. In Appendix C, DESCRIPTION gives the information about the scan.

INTEGRATIONS—The INTEGRATIONS parameter specifies the number of detector readings that are averaged together to make one raster line of image data. Allowable integrations are 1,2,4,5,10 for DF's and 4,8,10 for CT's.

CHANNELS—The CHANNELS parameter specifies the number of detector channels to sample from each detector reading (view). Of the 640 channels in the detector, 600 are data image channels. In CT mode, channels are a power of 2 such as 320 or 512. NOTE: Channels+FIRST should not exceed 601 or it records beyond the image data channels of the detector. In Appendix C, CHANNELS specifies that 512 channels are recorded for each view of data.

FIRST—The FIRST parameter specifies the detector channel from which to begin recording image data. The first image data detector is number 1. In CT mode, the first parameter is critical in determining the center of rotation of the data. The first parameter must be measured in such a way as to insure that the image data rotates on the center detector channel. NOTE: CHANNELS+FIRST should not exceed 601 or it will record beyond the image data channels of the detector. Appendix C, FIRST specifies that data are recorded beginning with detector data channel #47.

CLOCK—The CLOCK parameter specifies whether the signals from the encoder pulses, or the 60 Hz oscillator, are used to trigger the data acquisition system. The encoder pulses are derived from the 1000 line encoder and are representative of the axis motion through the INCREMENT specified above. Normal procedure is to use the encoder clock for the clock signal. In Appendix C, CLOCK specifies that the data acquisition system is triggered by signals from the encoder in the part manipulator.

CULLS—The CULLS parameter specifies the number of detector readings to throw away due to the time necessary for the part manipulator stalk to accelerate to and decelerate from a constant velocity.

CT WIDTH—The CT WIDTH parameter is the number of pixels obtained in every projection for reconstructing an image.

CT SCALE—The CT SCALE parameter is a scale factor only specified for CT operation.

TYPE The TYPE parameter specifies the extension of the image file generated by the X-ray computer system. The name of the file is the part identification code. In the above example, TYPE specifies that the image file is saved with the extension .CT1.

ARCHIVE—The ARCHIVE parameter specifies whether the image is saved in the ARCHIVE directory. If ARCHIVE is set to "NO", the image is normally not archived. However, it may be placed in the DISPO directory if the flaw analysis determines a DISPO disposition. If the parameter is set to "YES", the image is placed in the ARCHIVE directory. However,it may be placed in the DISPO directory if the analysis determines a DISPO disposition. The X-ray computer system allows the operator to override the ARCHIVE specification only if ARCHIVE is specified as "NO". In this case, the operator may direct the system to archive the image if desired.

DISPLAY: The DISPLAY section token is used to locate the DISPLAY section of the inspection plan file. This section contains information concerning the set-up of the displayed image on the high resolution display unit.

CLEAR—The CLEAR parameter determines whether the display is cleared before displaying the image.

FIRST VIEW—The FIRST VIEW parameter specifies the top of the image data window from which to display. In Appendix C, FIRST VIEW specifies the top of the image data window to be at view 1.

LAST VIEW—The LAST VIEW parameter specifies the bottom of the image data window from which to display. In Appendix C, LAST VIEW specifies the bottom of the image data window is view 512.

FIRST CHANNEL—The FIRST CHANNEL parameter specifies the left of the image data window from which to display. In Appendix C, FIRST CHANNEL specifies the left of the image data window to be at channel 1.

LAST CHANNEL—The LAST CHANNEL parameter specifies the right of the image data window from which to display. In Appenxid C, LAST CHANNEL specifies the right of the image data window to be at channel 576.

The next four parameters define the size of the display window and are never larger than the first view, last view, first channel, and last channel, but may be smaller.

FIRST ROW—The FIRST ROW parameter specifies the top of the display window in which to put the imgae. Appendix C, FIRST ROW specifies the top of the display window to be at pixel row 0.

LAST ROW—The LAST ROW parameter specifies the bottom of the display window in which to put the image. In Appenxid C, LAST ROW specifies the bottom of the display window is at pixel row 511.

FIRST COLUMN—The FIRST COLUMN parameter specifies the left of the display window in which to put which the image. In Appendix C, FIRST COLUMN specifies the left of the display window at pixel column 0.

LAST COLUMN—The LAST COLUMN parameter specifies the right of the display window in which to put the image. In Appendix C, LAST COLUMN specifies the right of the display window is at pixel column 575.

V1 to V2 defines the range of gray levels to be displayed on the high resolution graphics monitor. Z1 and Z2 defines the size of the graphic system's lookup table. R1 to R2 defines the range of the image data to be displayed.

V1—The V1 parameter specifies the intensity of the lookup table at the beginning of the ramp. In Appendix C, V1 specifies a beginnin ramp intensity of 0, the minimum.

V2—The V2 parameter specifies the intensity of the lookup table at the end of the ramp. In Appendix C, V2 specifies an ending ramp intensity of 255, the maximum.

R1—The R1 parameter specifies the offset to the start of the ramp. This number determines the initial starting position of the gray scale as shown by the bar on the right of the display screen. In Appendix C, R1 specifies the ramp to begin at an offset of 300.

R2—The R2 parameter specifies the offset to the end of the ramp. This number determines the initial end position of the gray scale as shown by the bar on the right of the display screen. In Appendix C, R2 specifies the ramp to end at an offset of 450.

Z1—The Z1 parameter specifies the offset to the start of the look up table. In Appendox C, Z1 specifies the look up table ramp to begin at an offset of 0.

Z2—The Z2 parameter specifies the offset to the end of the look up table. In Appendix C, Z2 specifies the look up table to end at an offset of 4095.

These parameters are used by the executive software to process the blade through the X-ray machine.

D. Executive Software

FIG. 17 illustrates a basic flow diagram of the executive software. In block 300, the executive software spawns the various processes used in data acquisition, display, flaw analysis and archiving purposes. The term spawn actually means that the executive system sets up the various processes, and when an appropriate condition is met for the process to become active, the process is initiated and proceeds in parallel with other processes in the computer system. After the data acquisition, display, flaw analysis and archive subprocesses are spawned, the executive software prompts the operator for a valid I.D., block 302. The routine validates the operator I.D. against a valid operator list and proceeds to log in the operator, block 304, if the operator's I.D. is on the valid operators list. If not, the operator is not allowed to log in.

After logging-in, the executive software initializes all the various queues and hardware in the system, block 306. The executive software initializes the programmable controller. The part manipulator is commanded to home the Z and theta axes. This homing allows a conveyor belt pallet with a gripper to be positioned in the inspection station. If the part manipulator is not home, there may be a chance of a collision if the manipulator is in path of the pallet and the gripper. In block 308, the executive software allocates the devices and the software needed to run the system.

The computer model of the conveyor belt is then initialized for being able to take 25 blades into the conveyor, block 310. The executive software then clears out the image files, disc files, and queue files used by the system for blade imaging and flaw analysis, block 312.

The next block is the X-ray initialization routine, block 314. This routine turns the X-rays on and performs an X-ray warmup depending upon how long the X-rays have been off. The warmup time for the X-rays are determined by a table lookup in the computer system. The initialized X-rays, block 314, records the date and time of turning on the X-rays for computing a time difference which can be used for determining the actual warmup time necessary for the X-ray system.

After initialization, the executive software receives commands from the operator, block 316. The executive system executes the command from the operator and returns to get another command. If an exit command is received in block 318, the executive software executes a shutdown procedure which closes all the files, clears appropriate buffers, shuts down the X-rays, homes the part manipulator axes, and processes the remaining blade images in the system, block 320.

The execute command executes various commands in the executive software, block 322. These commands include the initialize command, the command to initialize the system. An archive command which allows the system to flush out the archive system so that any files waiting to be archived are archived; a calibrate command that manually offset calibration data and stores the results into a special calibrate file; a help command which gives the operator a list of all commands that are available; an exit command turns the X-rays off and logs off the system; a new command that allows a new operator to log on the system; a label command which allows the operator to print a label on one of the gum labels on the printer in order to adjust the printer; a inspect command which allows the blades loaded into the X-ray machine to be inspected; and a plan command which allows the operator to change to a new inspection plan for all subsequently loaded parts.

A detailed flow diagram of the inspect command is shown in FIG. 18. The inspect command is the main command of the executive software. It allows access to DF and CT scanning. First, the operator inputs the inspection plan I.D., block 340. The inspection plan contains all the parameters for manipulating the blade, the setting of the X-ray power supplies, the commands for the display, and the data collection commands, block 341. The executive software then requests the operator to input the serial number of the part, block 342. When this is accomplished the executive software retrieves and updates the part information block with the parameters needed for processing the blade in the X-ray machine, block 343. The operator may also enter a command PLAN which is a system command at the part serial number level. By entering PLAN the operator is able to mix part types on the conveyor. When the PLAN command is entered, the operator is prompted to "enter part serial number". The the computer 28 interprets this action to mean that the operator wishes to use the new inspection plan for all subsequently loaded parts. The operator may perform this action at any time in the loading sequence before the END command is invoked. By using PLAN, therefore, the operator can place multiple part types on the conveyor at the same time and still have the correct inspection plan associated with each part.

The executive software then sets the power setting on the X-ray power supplies to the desired kilovoltage level and disables the power to the servomotor that control the variable power supply of the X-ray system, block 344. This insures a constant input power to the X-ray system during inspection of the blade. The executive software then determines whether a flaw report analysis is due on the blade that will be moved to the first unload station when the conveyor is commanded to move one station, block 346. If a flaw analysis report is required, the executive software begins generating this report, block 348. In automatic mode, a flaw report is printed at this point; however, in manual mode, the flaw report is printed immediately after inspecting the blade block 349 The executive software then determines whether a blade that will be moved to the first unload position requires a disposition, block 350. If a blade disposition is required, the appropriate disposition lights are illuminated at the unload station, block 352. The executive software then retrieves the 2-2T test data stored previously, block 354. The 2-2T test data represents calibration data taken on a test piece with known flaws. The 2-2T test piece consists of a known block of material with predetermined holes of particular dimensions drilled in a particular configuration. By storing a reference to the 2-2T calibration data with each blade image, the imaging capability with respect to sensitivity and resolution of the system can be documented. In essence, the 2-2T calibration data is reference data that is stored along with blade data for archiving purposes. For a better understanding of the 2-2T calibration method, attention is directed to FIG. 31 of the drawings wherein the 2-2T test piece is disclosed in greater detail.

The executive software then moves the conveyor one position to the next station, block 356. The part information block for the blade in the inspection station is retrieved, block 358. The parameters that describe the manipulation of the part manipulator are retrieved from the part inspection plan, block 360. The manipulator is then moved according to the commands in the part inspection plan and the blade is moved to a position between the X-ray source and the X-ray detector, block 362. The executive software reads the data collection parameters from the inspection plan, block 364. The executive software then starts the data collection in response to the data collection parameters, block 366. A DF scan or CT scan is made depending upon the inspection plan. The executive software starts the data acquisition at this point. Data acquisition is a parallel subprocess which allows the executive software to continue processing flaw reports from the last image or displaying the last image to the operator or archiving images. For the same blade, while one image is being generated, the previous image may be displayed and/or automatically processed. For multiple blades, while the image is being generated on a new blade, the automatic flaw processing can process the previous blade image. This does not, however, occur in manual processing mode. In this manner, blades can be inspected in real-time. The data acquisition system under control of the 60HZ clock or the encoder clock controls the sampling of the detector and the manipulator moves the blade through the appropriate axis. If a DF scan is requested by the inspection plan, the blade is moved in the Z direction. If a CT scan is requested by the inspection plan, the blade is rotated about the Z axis, 360 degrees. The sampling of the detector and subsequent processing of the scan is controlled by the image generator. It processes this scan and forms a digital image for storing on the computer system. After the image is completed, the computer is notified and begins the display portion of the inspection plan, block 370.

The executive software retrieves the display commands from the inspection plan and displays the image according to those commands, block 372. The executive software, however, begins a new blade inspection when the last blade image is completed. Note that more than one image may be required for a blade. The executive software continues processing the blade until all images are completed. After displaying the image, the executive software performs automatic flaw analysis if required, blocks 374 and 376. The executive software begins again at block 340 with the input of a serial number for a new blade to be inspected.

E. Flaw Analysis Subprocess

The Flaw Analysis Subprocess is a subprocess which provides flaw analysis for various aircraft engine parts for the X-ray image system. The flaw analysis system provides access to a large set of image processing operators and flaw analysis techniques. The flaw analysis subprocess provides the flexibility to take a quick look at the data or detailed flaw analysis techniques. For example, a user may be only interested in determining which sequence of commands are necessary to reduce the data to the point of being able to make a decision as to whether a blade meets the tolerance specifications. The flaw analysis subprocess runs on the computer system. The flaw analysis is invoked by the executive subprocess through the part inspection plan which contains commands for running the flaw analysis system.

FIG. 19 shows a block diagram of automatic flaw analysis subprocess. In block 400, the image data collected by the computer system is registered to a reference position which includes an area of interest but excludes as much of any extraneous image data as possible. All subsequent processing takes place with reference to this position. The data are then normalized to a dynamic range which varies with each flaw to be detected. It sometimes may appear that the background data is quite uniform or a trend is apparent in the data. In these circumstances, the trend is removed from the original data. Normalizing the data is to remove as much of the undesirable background as possible by filtering and subtraction techniques.

The image is then segmented according to the inspection plan for detection of flaws within the particular area of interest, block 404. In block 406, the feature of interest is extracted from image. This can be accomplished by a number of known techniques well known to those of ordinary skill in the art. Some of these techniques are thresholding to delineate structures, filtering of the data using various known image filtering techniques, and subtracting out structures for eliminating structures not required for flaw analysis. After the feature of interest is extracted from the data, the feature is compared to a standard for classification, block 408. The object of the classification is to determine whether the feature meets quality control standards for that the particular part. In block 410, it is determined whether the feature meets these standards within error limits determined by previous experience. If the features meets the standards within the error limits, the feature is accepted, block 412. If the feature does not meet these standards, the feature is rejected, block 414. The procedure then continues to block 416 for determining whether a new feature in the region of interest in the data should be analyzed. If a new feature is to be analyzed, the process begins again at block 406, extracting a feature in the region of interest. If no new feature in the region of interest is to be analyzed, a flaw report is generated by the flaw analysis subprocess that is printed out on the printer and attached to the part when it is unloaded from the X-ray machine.

In order to perform the flaw analysis techniques, a number of routines are used for manipulating image buffers and data structures associated with the image. The following is a listing of the routines available in the flaw analysis subprocess for flaw detection.

ABS—Calculates the absolute value of a buffer or a scalar.

ADD—Performs buffer to buffer, scalar to buffer, or scalar to scalar addition.

ARCCOS—Calculates the inverse trigonometric cosine of a buffer or a scalar for angles in radian measure.

ARCCOSD—Calculates the inverse trigonometric cosine of a buffer or a scalar for angles in degrees.

ARCSIN—Calculates the inverse trigonometric sine of a buffer or a scalar for angles in radian measure.

ARCSIND—Calculates the inverse trigonometric sine of a buffer or a scalar for angles in degrees.

ARCTAN—Calculates the inverse trigonometric tangent of a buffer or a scalar for angles in radian measure.

ARCTAND—Calculates the inverse trigonometric tangent of a buffer or a scalar for angles in degrees.

BOOL.FILTER—Creates a new list from an existing list using one to ten logical comparisons.

BSCAN—Extracts a bscan from a data set.

BUF.TO.FIELD—Writes the contents of a data buffer to the specified field of the specified list.

CARTPOL—Performs a cartesian to polar conversion.

CLEAR—Clears the contents of flaw analysis subprocss data structures.

COLADD—Provides the user with the ability to collapse one or more dimensions of an input buffer to 1 by adding all the elements across the dimension(s) of interest and placing the result in the first element of that dimension.

COLAND—Provides the user with the ability to collapse one or more dimensions of an input buffer to 1 dimension, by bit-wise ANDing all the elements across the dimension(s) of interest and placing the result in the first element of that dimension.

COLMAX'Provides the user with the ability to collapse one or more dimensions of an input buffer to 1 dimension by computing the maximum value of all the elements across the dimension(s) of interest and placing the result in the first element of that dimension.

COLMIN—Provides the user with the ability to collapse one or more dimensions of an input buffer to 1 dimension by computing the minimum value of the elements across the dimension(s) of interest and placing the result in the first element of that dimension.

COLMULTIPLY—Provides the user with the ability to collapse one or more dimensions of an input buffer to 1 dimension by multiplying all the elements across the dimension(s) of interest and placing the result in the first element of that dimension.

COLOR—Provides the user with the ability to collapse one or more dimensions of an input buffer to 1 dimension by bit-wise ORing all the elements across the dimension(s) of interest and placing the result in the first element of that dimension.

COMPLEX—Creates an output buffer to type COMPLEX*8 from two REAL*4 buffers.

COMPRESS—Performs garbage collection on the section by moving all free blocks in the section to one contiguous area at the end of the section file.

CONJ—Computes the complex conjugate of a data set.

CONTINUE—This command reverses the effect of the SUSPEND command, and allows the execution of a stopped script file to continue.

CONVERT—Converts the contents of the input buffer to the specified data type and places the results in the output buffer.

CONVOLVE—Convolves the input data buffer with a kernel data buffer and places the results in the specified output data buffer.

COPY—Copies all or a portion of the contents of a data buffer or list to a new data buffer or list.

COS—Calculates the trigonometric cosine of a buffer or a scalar for anglss in radian measure.

COSD—Calculates the trigonometric cosine of a buffer or a scalar for angles in degrees.

CREATE.FIELD—Creates a new field in an existing list.

CSCAN—Extracts a cscan from a data set.

DEBUG25.n—DEBUG25.n is used to invoke models named DEBUG25.1 thru DEBUG25.25. These modules serve as temporary interface routines to application software.

DEFINE—Defines a flaw analysis data structure.

DELETE—Deletes a flaw analysis data structures.

DISPLAY—Displays a data buffer in a display window on the graphics device.

DIVIDE—Performs buffer to buffer, scalar to buffer, or scalar to scalar division.

DOWHILE—The DOWHILE ENDDO structure allows the conditional repeated execution of a block of flaw analysis commands.

DUMP—Displays a formatted dump of the requested data structure.

FFT—Performs a two-dimensional FFT on the input data

FFTS—Performs a sophisticated two-dimensional FFT on the input data.

FIELD.TO.BUFFER—Extracts the contents of the specified field from each record in the specified list (in order) and places it into a data buffer.

GET.BUFFER.DIM—Gets the dimensions of a data buffer and assigns them to symbols.

GET.BUFFER.OFFSET—Gets the offsets associated with each of the dimensions of a data buffer and assigns them to symbols.

GET.BUFFER.SCALE—Gets the scale associated with each of the dimensions of a data buffer and assigns them to symbols.

GET.LIST.ID—Creates a symbol with the specified name and assigns to it the internal list identifier of the specified list.

GET.MEDIAN—Calculates the median value in a data buffer.

GROW.REGION—Identifies the regions in a two-dimensional binary.

HELP—Provides the user with the ability to obtain information on any command.

HIST—Calculates the histogram of a buffer.

HISTEQ—Generates a histogram equalized result from an input data buffer.

IF—The IF THEN ENDIF structure allows the conditional execution of a block of commands. This command is only meaningful in script files.

IFFT—Performs an inverse two-dimensional FFT on the input data.

IFFTS—Performs an inverse two-dimensional FFT on the input data.

IMAG—Creates an output buffer to type REAL*4 from the imaginary component of a COMPLEX*8 buffer.

INIT—Initializes a graphics device for use.

INIT.PER.STAT Initializes statistics used for performance monitoring. Available statistics include: elapsed time, CPU time buffered I/0, direct I/0, and page faults.

INSERT—Inserts the contents of one data buffer into another.

INTEGRATE—Integrates a data buffer over a specified dimension and places the result in an output buffer.

JUGGLE—Juggles or transposes one or more dimensions during a copy of one data buffer to another.

LN—Calculates the natural logarithm of a buffer or a scalar.

LOG—Calculates the common logarithm of a buffer or aa scalar.

MEDIAN.FILTER—Median filters an input data buffer and places the result in an output data buffer.

MINMAX—Calculates the minimum and maximum values in a data buffer.

MULTIPLY—Performs buffer to buffer, scalar to buffer, or scalar to scalar multiplication.

NL.FILTER—Provides the user with the ability to apply one of several non-linear filters to a data buffer. These filters select as the output value either the minimum, maximum, mean (average), or median value of the values in the filter window.

NORMALIZE—Normalizes the dimensions of a data buffer by shifting the non-zero (1) dimensions of a buffer to the left.

OPTIMIZE—Changes the data structure into a more efficient configuration.

OPT.THRESH—Computes the optimum threshold of a histogram.

PAD—Increases the size of a data buffer by adding a border of a specified size around the outside of the buffer. The data values in the edge of the original buffer are extended outward to fill the border.

PEEK—Peeks at a specifie location in a data buffer and displays the value at that location on the user's terminal.

POKE—Pokes the specified value into a data buffer at the specified location.

POLCART—Performs a polar to cartesian conversion.

QUIT—Exit without saving any user defined data structures or symbols.

RAMP—Provides the user with the ability to alter the color look up tables by entering a command, as opposed to using the alternate input device.

READ—Reads the specified file into the destination buffer.

Rotate—Rotates a two-dimensional data set by a specified angle.

SCALE—Scales an input data buffer to a specified range and stores the result in an output buffer.

SET—Sets certain system wide parameters.

SET.BUFFER.OFFSET—Provides the user with the ability to change the current offset values associated with each dimension of a specified data buffer.

SET.BUFFER.SCALE—Provides the user with the ability to change the current scale values associated with each dimension of a specified data buffer.

SHOW—Displays status on various system data structures.

SHOW.PER.STAT—Displays statistics used for performance monitoring. Available statistics include: elapsed time, CPU time buffered I/0, direct I/0, and page faults.

SIN—Calculates the trigonometric sine of a buffer or a scalar for angles in radian measure.

SIND—Calculates the trigonometric sine of a buffer or a scalar for angles in degrees.

SORT—Sorts a data structure.

SQRT—Calculates the square root of a buffer or a scalar.

STATS—Calculates the minimum value, maximum value, mean, and standard deviation of a data buffer.

SUBTRACT—Performs buffer to buffer, scalar to buffer, or scalar to scalar subtraction.

SUSPEND—This command causes the processing of a script file to be suspended and control to be returned to the user's terminal.

SWADD—Provides the user with the ability to add two buffers that are not necessarily the same size.

SWAND—Provides the user with the ability to bitwise AND two buffers that are not necessarily the same size.

SWDIVIDE—Provides the user with the ability to divide two buffers that are not necessarily the same size.

SWMULTIPLY—Provides the user with the ability to multiply two buffers that are not necessarily the same size.

SWOR—Provides the user with the ability to OR two buffers that are not necessarily the same size.

SWSUBTRACT—Provides the user with the ability to subtract two buffers that are not necessarily the same size.

SWXOR—Provides the user with the ability to exclusive OR two buffers that are not necessarily the same size.

TAN—Calculates the trigonometric tangent of a buffer or a scalar for angles in radian measure.

TAND—Calculates the trigonometric tangent of a buffer or a scalar for angles in degrees.

THINNER—Successively (for up to max.iter iterations) removes the boundary and corner points from a binary image until only a skeleton remains.

THRESHOLD—Thresholds a data buffer.

VMS—This command can be used to submit DCL command lines to the VAX software VMS for processing via the creation of a subprocess.

WRITE—Writes the specified buffer to a file.

XMIRROR—Mirrors a two-dimensional data set about the X axis.

YMIRROR—Mirrors a two-dimensional data set about the Y axis.

F. Image Archive Subprocess

The image archive subprocess is responsible for saving the images generated by the executive software. The image archive subprocess is invoked by the executive subprocess. The executive subprocess generates two types of images for archiving. These images are classified as either archive images or dispo images. Archive images are images that are designated either by the operator or an inspection plan to be permanently saved on tape. Archive tapes contain image data and data on blades. The tapes are permanently saved for future reference. Dispo images are all images from a blade which are given dispo disposition. If an image for a blade is designated as archive in the inspection plan, and the blade receives a dispo disposition from the operator during inspection, all images for the blade are saved under the dispo category and none are saved under the archive category. The computer operator interacts with the image archive system by loading the requested tapes on the computer and replying to the messages generated by the image archive subprocess on the console. When the executive subprocess is running and a number of images are designated to be archived, or dispo reaches a predetermined limit, the image archive system automatically saves these on tapes mounted on the computer system.

Referring to FIG. 20, the generated images are either archive or dispo images generated by the executive, block 452. The data images are stored in a first in first out directory, block 454. If the image is classified as a dispo image, the image is placed in a dispo directory, block 458. If the image is classified as an archive image, the executive software places the image in an archive directory, block 456. When either the dispo or archive directory is full, the executive software requests a tape to be loaded on the computer system tape drive, blocks 462 and 460. These tapes are stored permanently in the case of archive tapes for future references. In the case of dispo tapes, the tapes are saved until a determination of the disposition of the blade.

15. OPERATION AND METHOD OF DF SCANNING

The manner of making a DF scan image in the present invention is shown in FIG. 21. In DF imaging, the turbine blade 8 moves linearly past the linear array detector 64 and data are collected one line at a time to form an image. The part manipulator 16 moves the turbine blade 8 through the X-ray fan beam 13 generated from the X-ray tube 12. A timing pulse is generated by the programmable controller 20 as a function of the position of the part manipulator 16. Encoder pulses fed to the programmable controller 20 produce an encoder clock signal. The encoder clock signals the data acquisition system 24 to send data to the image generating system 26. The encoder clock signal is generated by a hardware logic unit in the programmable controller which has two dividers that are loaded with the number of encoder pulses to count before generating a timing pulse. It also contains a register to select the axis from which to monitor the encoder pulses. As a result, the hardware logic unit outputs a timing pulse based on the precise number of increments that a particular axis moves. This incremental movement is in the Z direction for a DF scan and theta direction for a CT scan.

Maximum data acquisition rate for DF inspection is 60 views per second. A view is a single X-ray detector reading, consisting of up to 600 data points spaced uniformly along a 3 inch line. Subsequent views are taken by moving the part approximately 5 mils between views in a direction perpendicular to the array. At the maximum data acquisition rate of 60 views per second, this gives a scan time of approximately 3.3 seconds per inch. If more exposure time is needed to improve the signal to noise ratio of the images, the data acquisition rate is reduced accordingly. For example, the data collection rate for a part of minimum size such as a F404 stage one turbine blade could be 20 views per second. The view is taken approximately every 5 mils along the dovetail axis of the blade. It takes 17.5 seconds to acquire data for an image of the 1.75 inch airfoil.

The hardware used for the DF scanning is the part manipulator 16, the linear array detector 64, the data acquisition system (DAS) and the image generating system 26. The image generating system includes a first array processor (APA), a second array processor (APB), and an image reconstruction processor. FIG. 22 shows a timing diagram for collecting the data, transferring it from the DAS to APA, APA processing, then APA to computer transfer of data. The data collection is controlled by one major loop in the first array processor. Referring to FIG. 22, this loop requests by interrupt the next view of data from the data acquisition system, this is shown on line APA/DAS in FIG. 22. On the next clock pulse, the DAS collects one view of data. This is shown in FIG. 22 as image #2, DAS. The DAS contains an A/D converter which is multiplexed sequentially to the 640 DAS inputs. Each DAS iinput corresponds to a detector array element. As each conversion is made, the data is sent to a first in first out buffer (FIFO) in the DAS-to-APA interface board. Data is collected in the FIFO until a counter in the interface indicates the buffer is full. The interface sends an interrupt to the APA and the APA reads the data into its input buffer. This data transfer requires approximately 0.5 milliseconds to complete. Upon completion of the data transfer, the APA requests another view from the DAS (in synchronization with the clock).

When the data transfer of a view is completed, APA begins performing the preprocessing calculations on that view. The preprocessing calculations consist of subtracting electronic offset values for each channel (obtained from averaging 1,024 views with no X-rays on). The data is then adjusted by using data from the reference detectors. The detector has two banks of 18 reference channels positioned away from the data channels. When imaging a proper sized turbine blade, the reference channels see only air attenuation and thereby measure X-ray tube flux level. Referring to FIG. 23, there is shown a top view of the X-ray source 12 and detector array 64. The area outlined generally by 470 is the area occupied by a turbine blade. A first bank of reference detectors 472 samples the X-ray level on a first side of the part envelope 470 for determining a first reference level. Another bank of reference detectors 474 are positioned on the opposite side of the part envelope for measuring the flux level of the X-ray source. A number of predefined reference channels are averaged, and the results are divided into the current data channel values. An entry in the configuration file determines which reference detectors are included for averaging. This selection is necessary to avoid choosing any bad reference channels or channels partially screened by the detector collimator.

The data, after being adjusted for reference data, is normalized with respect to "air" data. The "air" data is obtained prior to making each image by averaging 1024 views with the X-ray source on and no blade in place (air attenuation only). The air data is divided into the actual data on a channel by channel basis. This compensates for individual detector gain differences.

To convert the X-ray transmission data into path length data, logarithms of the data are taken. This log data is not directly proportional to the material path lengths mainly due to beam hardening effects. The X-ray tube is polychromatic, i.e. its spectrum contains many low energy photons as well as photons with energy near its maximum value. In general, materials tend to absorb the low energy (or "soft" photons) more efficiently than high energy photons. Accordingly, a small amount of material will attenuate proportionally (with respect to thickness) more of the spectrum. This nonlinearity affects the system directly in the CT reconstruction since the algorithm adds data from paths of various lengths. Additionally, for quantitative image processing, the data should be proportional to path lengths.

A table to correct for the beamhardening artifacts of homogeneous parts is downloaded to APA for each image. A different table has to be used for each material and each X-ray controller kilovoltage setting. These tables are stored in a database and the executive software system chooses the appropriate one based upon information in the inspection plan. This table is generated automatically by taking data on a special wedge shaped test piece 476, FIG. 24.

By using a wedge, such as a sensitometer, a function whose argument is thickness of the piece and whose output is the log of the transmission data is estimated. This function has the following properties:

1. $F(O) = O$
2. $F(T)$ is monotonically increasing
3. $dF(T)/dT$ is monotonically decreasing Currently a function of the form $C1(T-T\ ) + C2*(1-EXP(-B2*(T-T\ ))/B2$ is used to model F(T). C1, C2, and B2 must be positive to satisfy properties 1-3. From average thicknesses T sampled along the wedge or the test piece, estimates of F(T) and its error are made. The parameters C1, C2, B2, and T are determined as follows. For a given B2 and T, the C's are determined by solving the normal equations in a manner well known in the art. Then, T is similarly minimized. The latter parameter is included to properly register the position on the wedge since it tapers to zero. F(T) is now used to generate the table. Since absorption as a function of the log of the data is desired, a lookup table for the inverse of F(T) is generated using Newton's method. The table values are chosen so as to minimize interpolation errors in a Chebyshev sense. Thus, beam hardening is compensated by software in APA using a table lookup method.

When APA finishes processing a view, it stores the processed data. APA then transfers the view to the computer sytem. The computer system stores the view on the disc. The process continues until the blade is scanned completely in the Z direction. The resulting pixel image data on disc represents a DF image of the blade.

16. OPERATION AND METHOD OF CT SCANNING

The maximum data acquisition rate for CT inspection is 60 views per second. A view is a single X-ray detector array reading consisting up to 600 data points spaced uniformly along a 3 inch line. If more exposure time is needed to improve the signal to noise ratio on thicker parts, the overall data acquisition time is increased. As an example, the CT data collection rate for a part such as a F404 turbine blade airfoil could be 20 views per second. Since 1,500 views are required for a good CT image of this part, the total data acquisition time is 75 seconds.

In CT imaging, the blade is held at a given height along the Z axis and rotated about the Z axis in the X-ray beam. Referring to FIG. 25, there is shown a turbine blade 8 positioned in the X-ray fan beam 13 rotated about the Z axis at an angle theta past the linear array detector 64. Lines of data are recorded for a large number of angular positions, hundreds to thousands, and a CT image is computed from the data. The CT image lies in the plane ofthe X-ray beam rather than perpendicular to the plane as in the case of DF imaging. The time to collect CT data for an image can then range from tens of seconds to a few minutes.

A CT image can be obtained in a reasonable time for a single slice through a blade. For high volume parts and defects that require CT analysis, this poses a difficulty. The solution is to screen the parts for a defect presence in the DF mode and then to use a CT scan at that location to determine the presence or absence of flaw.

In the CT scanning mode, the data flow is the same as the DF scanning mode up to the point where the computer system receives the data from APA. Instead of the computer system storing the data to a disc, it is transferred for further processing to a second array processor (APB) which controls a special image reconstruction processor.

Because of this fact, two array processors and a special image reconstruction processor with bulk memory are required for DF scanning and CT scanning. It should be understood that the function of the DF scanning and CT scanning mode could be accomplished in a single array processor given enough parallel processing units, memory, and I/O capabilities. Thus, the description which follows may be varied from the specific form described hereinafter, while still obtaining the desired results of DF scanning and CT scanning.

In the CT mode, instead of the computer system being interrupted to write the process data from APA to the disc, a control word in front of the APA data buffer is updated. The second array processor (APB) polls the control word, and, if the control word has been updated, the APB reads the data buffer from the computer memory and stores it in APB's memory. Essentially, the data from the APA is double buffered in the computer memory. APA and APB take advantage of the direct memory access hardware of the computer system, thus requiring no interaction by the computer's arithmetic logic units. The transfer of data between APA and APB is invisible to the computer system. The data in APB is sent to the image reconstruction processor for computing the CT view.

In the image reconstruction processor, a filtered back projection CT reconstruction method is used. The data are convolved with a Schepp-Logan kernel (or other appropriate kernels). Each pixel in image space is mapped into the appropriate convolved data using linear interpolation and then added into a bulk memory point associated with that pixel in the image reconstruction processor. This step is called back projection. After the back projection for the last view is made, the reconstructed image is read from the image reconstruction processor via APB to the computer system for storage.

The data used in the reconstruction can be from either a one to one mapping of the detector data or from an average mapping. The one to one mapping makes an image with greater resolution but more noise and artifacts than the average mapping. The mapping function between detectors and pixels is done through the use of predetermined locator tables. For each view, the image reconstruction processor cycles through the pixel space associating each pixel with an X, Y coordinate. The coordinates are determined by an X, Y sequencer unit for using profile constants sent to the image reconstruction processor. These constants determine a scale and rotation coordinate system which changes with each view. The center of this coordinate system corresponds to the physical center of rotation. This X, Y information is then passed on to a weighting factor unit and a locator unit in the image reconstruction processor. The locator unit computes the detector number, a real number between 0 and 511, associated with each pixel. The detector number equals the magnification times $X/(R-Y)$+center detector; where R is the distance from the anode focal spot to the rotation center, and the coordinate system X, Y has the origin at the rotation cennter and is fixed with respect to the detector. A reciprocal table computes the inverse of the pixel from the focal spot ($1/(R-Y)$). The product of X times the reciprocal is computed and then used as a pointer to an arctangent table. The value in the arctangent table is added to the center detector number to compute the location The location number is used to access the data and difference data buffers. In a parallel process, the $1/(R-Y)**2$ waiting factor is calculated. The image reconstruction processor then multiplies the two results together and adds it to the appropriate bulk memory location. This location corresponds to a image pixel value. All these activities are pipelined for speed. For example, one pixel value is being multiplied by its weighing factor while the next pixel is being located and the pixel after that is being X, Y sequenced.

When the image reconstruction processor finishes a total CT back projection, it signals APB. APB reads the bulk memory of the image reconstruction processor view-by-view and stores it into a buffer of the computer memory. After eight views are read by the APB, the APB signals the computer system and the computer writes the buffer to disc storage. This process continues until the disc is filled with a complete CT image. While the APB sends the data to the computer system, it checks for any pixel outside the range of reconstruction. If an out of range pixel is found, it is zeroed.

The reconstruction process depends on a number of physical parameters which are system dependent. The three quantities which must be measured are the center detector number, the magnification, and the focal spot distance. The geometry for CT scanning is depicted in FIG. 26. In FIG. 26, F is the location of the X-ray tube focal spot, O is the center of rotation, R is the distance from the focal spot to center of rotation, X and Y are coordinates with origin at 0 fixed to the detector, X' and Y' are coordinates with origin at 0 fixed in the object, D and D' are the end points of the linear array detector 64 containing N elements, C is the location of the center detector (the points at which a projection of a line from F through 0 intersect at DD') and L is the distance from focal spot to center detector. The detector density, S, is the distance per detector, DD'/N. It is desirable to measure the physical parameters directly in the X-ray inspection system machine because they are related to the physical position of the X-ray tube anode.

The most crucial parameter in determining image quality is the center detector number. The center detector number is a real number that represents which detector element is intersected by a line from the X-ray focal spot through the center of rotation. The center of rotation and the center of the turbine blade need not be colinear. The fractional part of the real center detector number represents the weight used in linearly interpolating the data on each side of the center point.

An acceptable way to check the center detector position and to measure system physical parameters such as the magnification and focal spot position is to make a sinogram measurement of a simple pin gauge. Referring to FIG. 27A-D, a sinogram is made by taking data as the part is rotated through 360 degrees (i.e. acquiring the data in DF manner and manipulating the part in CT manner). The pin gauge consists of two pins, (478 and 480) small diameter, highly absorbing, spaced a known distance. The gauge is gripped so that the midpoint of the line between the pins is approximately on the ray between the focal spot and the system center of rotation. At gauge set-up, the midpoint is offset radially along FC from the center of rotation by some distance. As the part is rotated, each pin's position along the detector can be determined to within a tenth of a detector by parabolically fitting the data.

The center detector number is simply the average detector position of the pins as they are rotated over 360 degrees. The system magnification and the distance from the focal spot are determined as follows. Let DEL be the distance between pin positions from when they are closest together on one side of the detector to when they are closest together on the other side. Let S1 be the distance between pins when they are furtherest apart and closest to the X-ray source. Let S2 be the distance between the pins when they are furthest apart and closest to the detector. Because of the fan beam nature of the X-ray system, S2 is less than S1. These measurements determine the parameters in question. (Note that all the above distances are projected distances along the detector DD').

Let W be the physical distance between pins. Y is a measure of the midpoint offset distance from the center of rotation. MAG is the system magnification and R is the distance between the X-ray focal spot and the center of rotation. We have:

$$Y = DEL/\left(2*MAG*1 + \left(\frac{DEL}{2MAG*R}\right)^2\right)$$

$$R = Y*(S1 + S2)/(S1 - S2)$$

$$MAG = (S1 + S2)(1 - Y2/R2)/2W$$

These equations are easily solved iteratively. All these parameters are used by the CT algorithm to map pixels to detector values and to compute weighting factors.

17. Operation

The X-ray inspection system has two modes of operation. The first is a manual mode which allows an operator to manually scan a part to produce a DF or CT image, and the second is the automatic mode of operation. In automatic mode, the computer system provides automatic flaw detection. After scanning a blade, the resultant image is archived, a flaw analysis is performed and a part report is automatically generated.

FIG. 14A-B illustrates a flow diagram for operating the X-ray inspection system. In operating the X-ray inspection system, an operator sits at the computer console and logs in on the system, using an appropriate user name and password for protecting system integrity, block 500. The system is then initialized, block 501. The operator then enters his operator I.D. by entering it into the keyboard or, if appropriate, wanding the bar code from an operator's I.D. number usually placed on an operators badge, block 502. The system responds with operator I.D. logged in at date and time. The system performs an initialization procedure as described in the executive software. This involves resetting the system, putting the part manipulator at the home position and performing an X-ray tube warmup procedure for the amount of time required. The X-ray tube warmup time is dependent upon the length of time which the tube has been off, block 504.

The tube warmup procedure is done with the tube on a large focal spot. If the tube is not on a large focal spot, the systm informs the operator by a message on the operator's screen to turn the X-ray tube control to the large focal spot. The focal spot size is selected by a switch on the X-ray control unit. Once this is done, a warmup procedure for the X-ray tube begins.

When the warmup procedure is complete, the system informs the operator to return the X-ray tube to the small focal spot. All inspections are done with the tube on the small focal spot, and the system does not proceed until the X-ray tube is at the small focal spot.

Following the X-ray tube warmup, the system prompts the operator to enter a command. The operator may enter any of the following 8 commands:

CT Center—Run appropriate inspection plan, generate appropriate parameter and update configuration file.

Inspect—run a series of inspections on a batch of blades.
Help—list available commands.
Label—print a label for alignment of the part disposition label printer.
Archive—archive the data stored in the analysis and graphics computer to an archive data base.
Initialize—initialize the XIM system.
Calibrate—generate calibration data by acquiring offset (non X-ray signal) data.
New—allow new operator to sign on.
Beam—run inspection plan to acquire beam hardening
Beam a—run first part of beam hardening inspection plan.
Beam b—run second part of beam hardening inspection plan.
Exit—exit the system.

Assuming normal operations, the operator enters the inspect command, block 506. This command informs the system that the operator is ready to start inspecting blades. The system responds with, "enter the inspection plan I.D.," block 508. The inspection plan I.D. references a file containing the parameters for inspecting a part on the X-ray inspection system. For a better understanding of the inspection plan attention is directed to FIG. 16 of the drawings wherein the inspection plan is illustrated in detail. The inspection plan I.D. can be printed before hand for theoperator and placed in a binder indexed by part type and inspection operation. After entering the inspection plan I.D., the system sets a counter to zero, block 509. The system then responds with "part serial number," block 510. The operator wands in the number which contains the blade serial number from a bar code on the paperwork accompanying the blade.

At this time, it may be necessary to do a 2-2T image quality calibration. The frequency and type of parameters are usually determined ahead of time by a quality engineer and specified in the operation sheets. If a 2-2T calibration is required, the operations continue as further described in the 2-2T image quality check.

The system responds with "load part/push buttons," block 512. This commands the operator to load the blade in the gripper at the load station and push the start buttons, block 514. The counter is then incremented, signifying a part has been loaded, block 516. FIG. 29 shows the method of loading the gripper on the pallet. A gripper is placed into the load station pallet. A roll pin mounted to the gripper must be inserted into a slot on the pallet. The pin prevents the gripper from being misloaded onto the pallet, but allows the gripper to be easily lifted from the pallet. A gripper tool is used by the operator for loading the blade into the gripper. To load a blade, a pivot pin on the conveyor pallet is inserted into a hole of the gripper tool. The gripper tool is then pivoted toward the gripper. This activates the opening of the gripper jaws when an edge of the gripper tool is placed against a cam on the gripper. By applying pressure to the gripper tool and forcing the cam inward, the jaws on the gripper are forced open and the part is slid into the gripper. The pressure on the gripper is then relaxed, releasing the jaws and securing the part to the gripper. The gripper holds the blade firmly and prevents any movement during inspection. After loading the blade, the operator pushes the start buttons and the conveyor indexes.

Referring back to FIG. 28, once the operator enters the part serial number, block 510, and loads the turbine blade into the load station gripper, block 512, the two start buttons are pushed causing the conveyor to index one position, block 514. The start buttons are placed far enough apart to prevent an operator from pressing the buttons with only one hand. Since it requires two hands to push the buttons, the system can safely index the conveyor without concern that the operator's hands are in contact with the conveyor.

During the typical run of a batch of turbine blades, the pattern of entering the part serial number, loading the turbine blade into the gripper, and pushing the start button is interrupted under only two conditions. In this particular implementation, there are 18 conveyor pallets from the load station to the inspection station, inclusive. If less than 18 turbine blades are to be inspected, then the loading process must be terminated by the "END" command, block 509. The "END" command simply tells the system that no more turbine blades will be loaded onto the conveyor, block 518. The operator will no longer be prompted for a serial number, and the conveyor will index the first available part into the inspection station pallet position and begin processing a part, FIG. 30A-B. If the counter is zero, the system flushes the conveyor and generates a batch report, blocks 520, 522, and 524. Once all turbine blades currently loaded on the conveyor have been inspected, the operator will be prompted to enter the new inspect command, block 506. The second interruption of the loading sequence occurs when a turbine blade reaches the inspection station. In this case, after the seventeenth blade has been loaded and the start buttons have been pushed, the first part that was loaded (now sitting 17 pallets ahead of the load pallet) is indexed into the inspection station. At this point, the X-ray inspection of the turbine blade in the inspection station will be completed before the operator is prompted to enter the serial number for turbine blade number 18.

The disposition for the blade entering the first unload station must be available before the blade enters the unload station, block 540. If th system is in automatic mode, a part report is printed, block 541. In block 542, the disposition lights for the unload are then illuminated telling the operator the disposition of the blade. If a part is not at the inspection station, block 544, the system returns to enter more part serial numbers, block 510.

FIGS. 30A-B show a detail diagram of processing a part at the inspection station. Once a turbine blade enters the inspection station, it is X-ray imaged and processed according to the inspection plan, block 546, which was earlier identified by the operator. The turbine blade is immediately scanned, block 508, to generate an X-ray image as specified in the inspection plan. The first image to be generated will typically be a DF image, but is not limited to a DF image. If any suspect areas are identified in the DF image, the operator can then decide to do a CT scan before making final disposition. In some cases, a CT image may be desired immediately with no intermediate DF scan.

In any case, once the scanning for the first image is complete, block 550, the resultant image will be handled in one of two modes, block 552, production mode or non-production mode.

In production mode, the image is immediately displayed on the high resolution display for the operator to view, block 554. The inspection plan is then interrogated to determine if manual or automatic image processing is desired, block 556. Manual processing means that the operator will interpret the X-ray image being displayed, the scan sequence for the next image to be generated will be initiated, block 560, if another image has been specified in the inspection plan, block 558. After the operator enters a disposition for the image being displayed, block 562, he is then asked if the image should be archived, block 564. If archiving is requested, a flag is set, block 565. Archiving means that the image data will ultimately be stored on the same long term storage medium such as magnetic tape or optical disk. The archiving of images can also be specified directly in the inspection plan. If the inspection plan specifies an image for archive, the operator's response to the archive question is ignored.

Automatic image processing means that automatic flaw analysis will be performed on the image, block 570, and a flaw report data file will be generated, block 572. In non-production mode, the image is immediately made available to the flaw analysis system, block 570, for automatic flaw analysis. The system does not wait for the flaw report, block 572, to be generated but immediately initiates the scan sequence to generate the next image, block 574, if one has been specified, block 576, in the inspection plan. The important difference of this mode from production mode is that the image is not necessarily displayed for the operator to view. Display commands available in the executive software allow the image or portions of the image to be displayed at incremental steps through the image processing cycle; however, if so desired, no image at all may be displayed. This mode is used for debug and demonstration purposes, hence, the name non-production.

As previously discussed, in the manual production mode, the operator has several image manipulation commands at his disposal to aid in determining the disposition of each image. These commands can be entered either at the keyboard or the bar code wand and are listed as follows:

Contrast, text, line, circle, erase text, erase graph, measure, zoom, locate, scroll up and scroll down.

A. Contrast

The contrast mode changes the contrast and/or brightness of the image on the high resolution display. A series of switches on the trackball unit increase the contrast and/or brightness. A first switch is used to select brightness or contrast. A second switch is used to control the amount of light and dark displayed on the image when in the brightness mode. When in the contrast mode, the second switch is used to control the number of grey levels displayed on the high resolution display. The rate of change for either contrast or brightness is produced by pushing a rate button on the trackball unit. When the rate button is pushed in one direction, the rate of change increases. When the rate button is pushed in the other direction the rate of change decreases. While in the contrast mode, a negative button on the trackball unit is used for producing a negative image of the present high resolution display.

There are two ways to exit from the contrast mode. The first is to draw the bar code reader wand over the contrast or any other bar code. The second is to push an exit switch on the trackball unit. The high resolution display is now ready for another mode of operation.

B. Text

This mode writes text on the image. In implementing this mode, a message appears on the operator console. The message commands the operator to mark the position on the image where the operator wants the text to appear. The method of positioning the text is to use the trackball unit which controls the position of an arrow on the high resolution display. The point of the arrow is where the text begins. The text is typed on the operator keyboard and appears on a operator screen as it is being typed. When the desired text is entered, pressing the return key causes the text to appear on the high resolution display screen at the desired spot. A graphics display printer such as one made by the Tektronics Corporation, can be used for copying the high resolution display. The text on the high resolution display appears on this print. However, the annotation is not included in the archived image data.

C. Line

The line mode draws a line on the image. When implementing this mode, a message appears on the operator console commanding the operator to mark the start of the line. This is done by using the trackball unit and placing the arrow on the screen at the desired starting point of the line. When the arrow is pointing to the desired location of the line, the first button on the trackball unit is pressed. When the ball on the trackball unit is now moved, a line appears from the starting point to the point of the arrow. The line is adjusted to a desired position and pressing the first button again causes a permanent line to be drawn from the starting point to the ending point. If another line is desired, the operator repeats the above steps.

D. Circle

The circle mode draws a circle on the image. When the circle mode is enabled, a message appears on the operator's screen requesting the operator to place an arrow on the high resolution display at the center of the circle. The arrow is located where the center of the circle is desired by moving the ball in the trackball unit. The first button on the trackball unit is pressed. When the ball is moved, the circle expands from the located center. When the desired size of the circle is acquired, the first button is pressed again and the circle remains on the screen.

E. Erase Text

The erase text command erases all text on the high resolution display.

F. Erase Graph

The erase graph command erases all graphic images (lines and circles).

G. Manual Measure

The measure code measures a distance on a turbine blade. When the command is invoked, a message appears on the operator's screen. The message instructs the operator to mark the first spot of the distance on the blade to be measured. This is done by moving the arrow on the high resolution display with the ball and trackball unit. When the arrow is placed at the desired spot on the image, the first button on the trackball unit is pressed. A message appears on the operator screen asking for the second point. When the arrow is again moved by the track ball unit to a second desired point and the first button is again pressed, the measured distance between the two points is displayed on the operator console in inches or decimal parts of an inch. This is perhaps the most important command of the display commands. It is used for measuring numerous blade characteristics for flaw analysis on the turbine blades.

H. Auto Measure

The operator places the arrow on one side of a feature to be measured and presses blue button. The operator then places the arrow on a point on the other side of the feature (a graphical line is simultaneously drawn) and presses the blue button. Software determines the size of the feature.

I. Zoom

The zoom command enlarges a section of the image on the high resolution display. When the command is invoked, a message appears on the operator's screen instructing the operator to mark the center point of the area to be magnified. The arrow is moved on a high resolution screen using the ball and trackball unit and the first button is pressed. A 2× image is displayed on a large screen with a point marked on the original image being in the center of the screen. If an additional 2× magnification is desired, the above procedure is repeated. This produces a 4× image on the screen. The procedure can be repeated a total of 4 time for a maximum magnification of 1×.

J. Locate

The locate mode determines the position of a point on the turbine blade. When the command is invoked, a message appears on the operator's screen instructing the operator to mark the point to be located. This is done by moving the arrow on the high resolution display with the ball in the trackball unit. When the tip of the arrow is at a point of interest, pressing the first button on the trackball unit displays the coordinates of the point on the operator console. These coordinates are the row position, the pixel number, and the Z height in Z axis encoder counts. If the point marked is one for which a CT slice is desired, the Z height count number is recorded for later input into the CT scan plan.

K. Scroll Up and Scroll Down

The scroll commands either scroll the image up or down depending upon which command is invoked. The scroll is used when the picture is too large in the vertical direction to fit on the high resolution display. When this occurs, only part of the image is displayed at one time. When the scroll up command is invoked, the image is shifted up by ¼th the previous screen. When the scroll down command is invoked, the image displayed on the high resolution display is shifted down ¼th of the previous image.

As previously discussed, in the automatic image processing mode of operation, block 242, each image is processed without help or intervention from the operator. As a representative example of an automatic flaw detection procedure, the automatic inspection of the meniscus geometry for a T34 blade is described. The TF34 blade inspected is a small 2 inch by 1 inch thin stage 1 high pressure turbine blade. A prominent feature of the T34 blade is a cavity about 60 mils in diameter along the length of the blade. The cavity is cast into the blade and is open to the outside. A plug is brazed into the top of the cavity to close the opening. The blade is inspected after the brazing operation to insure that the braze completely fills the gap between the plug and the cavity. Surface tension forces the braze through to the bottom of the plug and a meniscus forms if the braze flow is adequate.

The inspection task is one of examining the geometry of the cavity top. The T34 blade is imaged in the DF mode at the angle where the X-ray beam is as perpendicular as possible to the broad side of the blade. This angle allows the cavity to stand out as much as possible in the image. The flaw analysis system extracts the outline of the cavity so that the distances across the cavity from the top and downwards for about 75 mils is accurately measured. The distance measured is used to classify the meniscus braze as successful or not.

Before the flaw analysis system is run on the data, a process window is selected during previous interactive sessions with typical blade images. The process window is selected to include the area of interest but to exclude as much of any interfering structure as possible. All subsequent processing by the flaw analysis system takes place within this window. A border is established around the window and is filled with neutral data before processing to make sure that illegal data does not propagate into the window region.

The window for the TF34 meniscus encloses image data with a uniform background. However, the data does exhibit a trend in the horizontal direction and processing is done to normalize the background. A reasonable approximation that the trend function is linear and monotonically increasing or decreasing is made. If it becomes necessary, linear approximation can be substituted by a low-order polynomial approximation. The cast cavity can be described as a cylinder with a diameter of 57 to 65 mils. If the background data is normalized to appear flat, the cavity is extracted by thresholding. The cavity appears dark against a light background, so a decline in values occurs as one progresses from outside the cavity into the cavity. The edge of the cavity is located at the position of maximum intensity value associated with the cavity. The threshold value required to extract a cavity is this maximum intensity value. The assumption is made that the highest intensity value belonging to the cavity is found at the top of the cavity where the meniscus is formed. An acceptable threshold value could also be selected elsewhere such as the side entrance to the cavity.

Even though the background appears quite uniform, the blade becomes thinner toward the trailing edge and there is a definite non-uniform trend in the data in the horizontal direction. If this trend is not removed, the cavity can not be extracted accurately by thresholding. A slight trend in the vertical direction is also removed. The trend removal is done by estimating the trend and subtracting the trend from the original data. The trend in the horizontal direction is estimated from the total amount of difference across the horizontal data. It is a linear correction based on the intensity at the edges of the window. Window placement is important so that interior structure does not fall at the window edge. This is accomplished by using the computer to register blade images consistently and by offline interactive sessions to locate proper window position.

If A is the original array of data, I is the column index and J is the row index, the expression for the trend is equal to $A(I,J) - A(N,J)$. The trend is computed and removed for each separate row of data or an average trend can be computed and removed for all the rows. The trend is found for each row of data to force identical dynamic range for all rows. Using the linearity assumption, a column by column incremental range can be simply estimated as a fraction of the total trend. The trend is then subtracted from each row of data, thereby normalizing the data in the horizontal direction. A similar procedure is followed to remove the vertical trend. However, the vertical trend is removed by simply adjusting the row values so that the first column value for each row is the same. This procedure works because the dynamic range of the data for each row is forced to become constant and the data is relatively free of noise.

The main objective of the flaw analysis system for the T34 blade is to outline the cavity for the T34 meniscus. The first step of the procedure is to test for the presence of the plug. A row of data is sampled from the top of the process window and the dynamic range of the data on the row is computed. Another row of data is sampled near the bottom of the process window and the dynamic range of that row is also computed. If the plug is missing, the ratio between the dynamic ranges of the two rows is approximately 1, because the cavity extends through the cylinder all the way to the top. If the plug is present, the data at the top will have a very small dynamic range because it will come from solid metal, so that ratio is significantly different from 1. To determine the existence of the plug, the ratio is compared to a predetermined tolerance value. The plug detection formula is $$TOP = MAX(A(I,J)) - MIN(A(I,J)), \text{ For } J = TOP + 5$$

$$BOT = MAX(A(I,J)) - MIN(A(I,J)), \text{ For } j = BOT$$

$$Ratio = \frac{BOT}{TOP}$$

If the ratio value is less than the predetermined tolerance value, then the plug does not exist and the procedure ends.

If the plug is present, the next step of the procedure is to locate the top of the cavity by detecting the greatest transition in a vertical direction of the data. The cavity data is of lower intensity than the background data, so the maximum transition is negative when the data on a selected row is subtracted from the data on the row below. The position where the cavity just begins is extracted. This is insured by associating the transition value with the selected row point. When proceeding from the uniform background into the cavity, this procedure locates the cavity edge. Because the cavity is surrounded by a nearly uniform region and because the top of the cavity is spherical, the position with the greatest negative value transition occurs is guaranteed to be the top of the cavity. Since it is desirable to work with a large data difference rather than small data difference for a robustness, the data difference is averaged or extended over several pixels rather than a single pixel. Integrating the first difference over several pixels is equivalent to using the difference in data at the end points. Several transition values are, therefore, integrated, and the first position where the maximum negative transition begins is selected as the cavity top. The integration of transition values is equal to CAV TOP=MIN(A(I,J))−A(I,J−N)), over all rows.

N defines the integration factor, or the nth difference. One value for N is 3 which means that the major transition from background in the interior cavity region extends over 3 pixels or about 15 mils.

Once the appropriate transition value is found, the row containing the top of the cavity is found. The same row of data with a normalized background is then scanned for the minimum value which corresponds to the maximum intensity value belonging to the cavity. This value is later used to extract the cavity boundaries. The medium value from a selected number of adjacent points determines the threshold. The selected number of points usually determines the width of the top row of the cavity. Only one point is used for the threshold selection for the final implementation.

To outline the cavity boundaries, the normalized data is scanned over the whole area of interest. Any pixels with intensity values equal to or below the selective threshold value are marked by the column position of where they occur. The final output consists of an output of an array of numbers where each row corresponds to a row in the windowed region. The boundary of the cavities is defined row by row, by the column position of the entries to and exit from the cavity. This array of column boundaries is used for a classification of the results.

The width of the meniscus at the top of the cavity determines whether the blade is acceptable or not after the plug brazing operation. If the width is greater than 25, mils the blade is rejected. If the width is less than or equal to 25 mils, the blade is accepted.

Appendix A contains the source routine for performing the above flaw analysis on the T34 meniscus inspection. The source program is part of the flaw analysis system which is used for automatic flaw detection. In a similar manner, flaws for other blades are found and a disposition of the blade is determined.

Once an image has been processed, either manually or automatically, it must be determined if another image is to be generated, block 580. If so, the imaging on the next image is progressing while the image processing was being performed on the current image. Hence, the software must now wait for the generation of the next image to complete, block 550, and repeat the previously described cycle until all images have been generated and processed. The parallel nature of the image generation and image processing greatly increases the speed and throughput of the X-ray inspection system.

After the turbine blade has been completely inspected according to the inspection plan, the operator is given the options, "Continue," "Again," and "Tomography." The "Continue" option results in a normal completion of the inspection for the turbine blade currently being addressed. All images flagged to be archived are copied into a separate disc directory and entered into the archive data base, block 586. If a part report is currently available for the turbine blade just inspected, as in the case of manual mode, block 592, it is printed at the operator's console on gummed labels, block 594. This report is made up of data submitted by the operator (manual mode) or derived from the automatic flaw processing report file (automatic mode). The automatic mode report will not be printed until the part indexes into the first unload station, block 540. This delay allows time for automated processing to continue even after the part has left the inspection station. The part counter is then decremented for each turbine blade that has been inspected, block 596. The "Run Again" option allows the operator to repeat the inspection using the inspection plan originally identified when the turbine blade was loaded onto the conveyor, block 582. If for some reason, one of the images previously generated was not imaged properly due to some anomaly, the operator may decide to run the inspection again. The imaging will then proceed in a manner to that previously described. The "Tomography" option, block 584, 232, allows the part to be inspected according to an inspection plan, block 590, previously defined within the original inspection plan. In practice, the original inspection plan identified by the operator before loading blades onto the conveyor will usually specify the generation of DF images. Once areas of interest have been identified within particular DF images for a particular turbine blade, the operator may desire a computed tomography (CT) image through the area of interest. By specifying a CT inspection plan within the original DF inspection, the operator then has the option to reinspect a turbine blade with the CT inspection plan. The reinspection option is very important in analyzing random anomalies that may be found in turbine blades. Note that even through the option is called "Tomography," the reinspection plan is not required to generate CT images only, but can specify any combination of DF and CT images desired.

Once the operator has selected the "Again" or "Tomography" option as many times as desired, and in whatever order is desired, the "Continued" option must be selected to terminate the inspection and allow the turbine blade to leave the inspection station. The executive software then determines whether this is the last part. If not, the system indexes and parts arrive at the unload area. The operator now has to unload the part from the unload station. The unload area consists of three stations. The blades are unloaded at any one of these stations. If a blade has not been removed by the time it reaches the third unload station, the conveyor will not index until the blade has been removed.

The plan may also call for multiple images. The executive software requests data for the imaging parameters for all images in the reinspect plan entered. The blade is then imaged for the inspection plan and displayed on the screen. Following evaluation and disposition of the images, the system again asks whether to continue, run, or tomography. The executive software then determines whether this is the last part. If not, the system indexes the conveyor belt to inspect the next part. If so, the turbine blade reaches the unload area. The operator now has to unload the part from the unload station. The unload area consists of three stations. The blades are unloaded at any one of these stations. If a blade has not been removed by the time it reaches the third unload station, the conveyor belt is not index until the blade has been removed.

When the blade enters the unload area, the executive software illuminates a display on the unload station for the blade indicating the disposition given to that blade. For example, if the blade is accepted the green light is illuminated. At the printer, a label is printed when the blade leaves the inspection station. The label indicates the disposition of the blade and the type and location of any flaws found.

The blade is unloaded and removed from the gripper using the gripper tool. The blade is taken and put into a envelope with the manufacturing routine card. A gummed label is printed with an inspection summary, peeled off from the backing, and affixed to the manufacturing routing card.

Following the above procedure, a batch of turbine blades can be entered into the machine for flaw analysis. The blades may be analyzed with an automatic flaw analysis system or by manual flaw analysis by the operator. The X-ray inspection system takes advantage of the parallel processing of the image processing system and the computer system by generating images during the interaction of the operator and during automatic flaw analysis. This results in a real time X-ray inspection system.

The tomography option also speeds up the X-ray inspection of aircraft turbine blades. The system can be run primarily in the DF image mode under manual intervention. The operator, by examining the DF image, determines whether a reinspection is necessary using a CT image. In this manner, the blades can be quickly inspected for flaws and, if an area of interest is detected, the blade may be reinspected in the CT mode for further analysis.

18. 2-2T IMAGE QUALITY CHECK

Referring to FIG. 31, there is shown a 2-2T test object consisting of a sandwich of metal layers 100 and 102 which conform to the resolution limits of ASTM Standard E142-17. The 2-2T test piece contains three holes, 104, 106 and 108, aligned in a vertical direction. The hole 104 has a nominal diameter of 40 mils. The hole 105 has a nominal diameter of 11 mils and the hole 108 has a nominal diameter of 20 mils. The 2-2T test gauge is placed in the system and a DF image is taken of the 2-2T test gauge. The DF image from the test gauge is archived with images from every blade. In this manner, the image from the gauge can be compared to calibrate the images of the blade. The 2-2T test data is stored on the archive files for later reference.

19. BAR CODE READER

Referring to FIG. 32, all of the commands and operations described previously are entered on the operator keyboard or by a bar code wand 34. The operator console 19 includes a bar code reader 34 for reading bar codes which describe the operations, commands, or information about the blades to be processed, the keyboard 601, operator display 18, the track ball unit 236, and the high resolution display 32. When the operator desires to enter a command, instead of using the keyboard, the operator wands the bar code reader over the appropriate command from a bar code list 602, and the command is entered into the computer. This saves time for the operator by having predetermined commands for wanding into the X-ray image system.

FIG. 33 shows a bar code sheet that accompanies a TF34 turbine blade. The bar code sheet includes bar coded flaws that can be detected by the operator. For example, if the operator detects an overdrill situation, the operator will wand in the overdrill flaw. As is shown in FIG. 33, the bar code sheet is used for entering commands to the computer system and for describing flaws on a part at the inspection site. The bar code saves time for the operator and allows faster processing of the blades through the system.

20. CONCLUSION

An X-ray production system has been shown for measuring and testing aircraft engine parts in an X-ray inspection machine. The system detects flaws by digital fluoroscopy images. FIG. 15 shows a digital fluoroscopy image of a F404 turbine blade. If an area of further inspection is noted on the digital fluoroscopy image, a computed tomography image is produced. The computed tomography image of the part is generated in the plane of the X-ray beam image. FIG. 16 shows a computed tomography image of an F404 integral tip cap. The computed tomography image clearly shows a scarfing condition caused by an over drilling operation on the blade.

In manual mode, a trained operator interprets the images and makes quality decisions. In the automatic mode, an automatic flaw analysis software detects flaws and notifies the operator of the disposition of the blade.

Image processing of the blade encompasses the location of the region of an image where a specific flaw may reside, the automatic extraction of parameters from that region of interest and the use of those parameters to decide automatically the presence or absence of a flaw. Processing is performed on the region of interest rather than on the entire image to reduce computation time.

The X-ray inspection system of this invention provides new capability for making, digital fluoroscopy and computed tomography at a rate consistant with the inspection of parts produced in volume. Automatic image processing and flaw identification have been demonstrated. The system provides an environment for an operator to interface with an x-ray inspection system to process parts in a factory environment.

We claim:

1. A computer based system for nondestructive measuring and testing of a manufactured part by X-ray analysis comprising:
   means for transporting a part from a load station to an inspection station;
   an X-ray source positioned for generating a high intensity X-ray radiation beam through a predetermined area within said inspection station;
   an X-ray detector for converting received X-ray radiation into electrical signals representative thereof;
   means for directing the X-ray radiation beam toward said detector;
   means in said inspection station for positioning the part in the X-ray radiation path between the X-ray source and X-ray detector;
   means for moving the part linearly in a plane substantially normal to an axis of said X-ray beam so that a predetermined area of the part is scanned by the X-ray radiation beam for generating electrical signals representative of a first planar image of the part;
   means for analyzing said first planar image for identifying specific areas of the part having probable flaws;
   means for positioning the part within the X-ray beam such that each of said specific areas is sequentially exposed to the beam;
   means for rotating the part within the X-ray beam about an axis normal to the beam at each of said specific areas for generating images of the part along a plane coincidental with each of said specific areas and normal to said axis of rotation for generating electrical signals representative of a second planar image perpendicular to said first planar iamge;
   means for converting said electrical signals to digital data representative thereof;
   means for converting said digital data to pixel image data;
   means for generating said first and said second planar images of the part from the pixel image data, and
   means for analyzing said first and second planar images for identifying flaws in the part.

2. The system of claim 1 wherein said transport means comprises means for sequentially transporting each of a plurality of parts from the load station to the inspection station and from the inspectiopn station to the load staion, the system further including computer means responsive to each part arriving at the load station from the inspection station for indicating a disposition of the part selected from the categories of passed, failed and re-inspect, said computer means inhibiting operation of said transport means until passed and failed parts have been removed therefrom, said computer means being operative to return the part designated for re-inspect to the inspection station.

3. The system of claim 2 wherein the computer means includes means for automatically identifying a first inspection of a part and for causing the inspection station to generate the first planar image of the part, the computer means automatically identifying a second inspection of a part for causing the inspection station to generate the second planar image of the part.

4. The system of claim 3 wherein said positioning means includes gripper means for holding the part, said gripper means having an extension flange oriented parallel to said axis about which the part is rotated, the system further including:
   means for rotating said gripper means such that said flange is alternately positioned adjacent opposite edges of said detector; and
   means for determining the position of said flange with respect to adjacent ones of said detection elements and for shifting the position of said detector such that said adjacent ones of said detection elements are equally spaced from a center of said detector whereby said axis about which the part is rotated is centered with respect to said detector.

5. A method for computerized measuring and testing of a part, comprising the steps of:
   providing a directed beam of X-ray radiation;
   positioning a part in the X-ray radiation beam;
   moving the part in a plane perpendicular to said X-ray beam such that a predetermined area of the part is exposed to the X-ray beam radiation;
   measuring the radiation passing through the predetermined area of the part;
   converting the measured radiation to digital data;
   transmitting said digital data to a computer processing unit;
   converting in the computer processing unit the digital data to pixel iamge data;
   generating a first planar image of the part from the pixel image data, said first image representing an image of the part perpendicular to the X-ray radiation beam;
   analyzing the first image for identifying probable flaws in the part;
   positioning the part in the X-ray beam such that each of the probable flaws is aligned with the beam;
   rotating the part about an axis normal to the X-ray beam for generating a tomographic image of the part in a plane of the beam for each of the probable flaws; and
   analyzing the tomographic image for identifying flaws in the part.

6. The method of claim 5, wherein the step of analyzing the first image further comprises the steps of:
   storing in memory data defining desired dimensional characteristics of a part;
   determining actual dimensional characteristics of the part from the first image; and
   correlating data representative of actual dimensional characteristics of the part with the stored data;
   comparing the actual dimensional data to the desired dimensional data for determining acceptability of the part.

7. A method of computerized measuring and testing of a part, comprising the steps of:
   providing a source of a directed beam of X-ray radiation;
   providing a linear array detector having a plurality of radiation detecting elements for receiving X-ray radiation;
   positioning a part in the x-ray radiation beam between the source and the detector such that some of the radiation received by predetermined elements of the detector is not intercepted by the part; and
   normalizing data generated by the detector in response to radiation passing through the part by adjusting the data as a function of intensity of the X-ray radiation beam as determined by radiation received by the predetermined elements of the detector.

8. The method of claim 7 further including the steps of:
   positioning a sensitometric device having a predetermined graduated density of X-ray attenuation characteristics between the source and the detector;
   collecting data from the detector representative of the radiation intensity received by the detector from each of a plurality of positions on said sensitometric device for establishing at table of data representative of X-ray beam hardness;
   storing said beam hardness data in a computer memory; and
   adjusting the data from X-ray radiation passing through the part in accordance with the stored beam hardness data.

9. A computer based system for non-destructive measuring and testing of a manufactured part by X-ray analysis comprising:
   a loading station for loading a part into a part holding mechanism, said mechanism being adapted to hold the part in a predetermined orientation;
   conveyor means for transporting the part from the loading station to an inspection station;
   an X-ray source for generating a high intensity X-ray radiation beam;
   a linear array X-ray detector for converting received X-ray radiation into electrical signals representative thereof;
   means in said inspection station for grasping said part holding mechanism and for positioning the part in an X-ray radiation path between the X-ray source and the X-ray detector;
   means coupled to said grasping means for effecting relative motion between the part and said X-ray radiation beam; and
   means for converting said electrical signals to data suitable for two dimensional representation such that the part can be measured and defects recognized from the representation.

10. The system of claim 9 wherein said X-ray source includes means for collimating said radiation beam into a fan shape in a horizontal plane, the beam being wider than the part, and wherein said motion effecting means comprises means for moving the part vertically through said beam for obtaining data for contructing a first planar image of the part.

11. The system of claim 10 and further including:
    video means for displaying said first planar image;
    means for identifying locations in said first image corresponding to selected areas of potential failure of the part;
    means for comparing characteristics of the part at said identified locations to previously obtained desired characteristics;
    means for identifying characteristics having values outside a predetermined range of values of said desired characteristics; and
    means for automatically directing tomographic X-ray examination of said identified characteristics.

12. The system of claim 11 and further including means for analyzing tomographic images of the part, said analyzing means comparing said tomographic images to stored data representative of desired characteristics of the part.

13. The system of claim 10 wherein said linear X-ray detector comprises a plurality of closely spaced detection elements arranged in a linear array, said detector having a width such that at least some detection elements receive radiation which has not passed through the part, said converting means including means for measuring the X-ray radiation levels received by the at least some detection elements and for normalizing the data obtained from others of the detection elements in accordance with the measured radiation levels.

14. The system of claim 13 and further including means for energizing the X-ray source without a part in the inspection station and for obtaining data from said detector during such energizing, and wherein said converting means comprises means for averaging the data obtained from all the detection elements to generate an average compensation value and dividing the average value into the data obtained from each detecting element for compensating for detection element gain differences, 15. In a computer based system for non-destructive measuring and testing of manufactured parts, having an X-ray source for providing a directed beam of X-ray radiation, a linear array X-ray detector for converting received X-ray radiation into electrical signals thereof, the method comprising the steps of:
    a. loading a part in a gripper such that only a base poriton of said part is held by opposing jaws of the gripper;
    b. transporting the gripper with the part on a transporter into a part receiving station;
    c. acquiring the gripper with a manipulator, the manipulator automatically centering and aligning the gripper along a projected central axis of the manipulator; and
    d. operating the manipulator for positioning the part in a predetermined orientation in a path of X-ray radiation from the X-ray source.

16. In a computer based system for nondestructive measuring and testing of manufactured parts, an X-ray source for providing a directed beam of X-ray radiation, a linear array X-ray detector for converting received X-ray radiation into electrical signals representative thereof, the method comprising the steps of:
- providing control signals for positioning a part in each of a plurality of predetermined positions adjacent an X-ray source;
- energizing the X-ray source for generating radiation in coordination with said positioning means for effecting exposure of said part to X-ray radiation at each of said predetermined positions;
- generating signals responsive to each of said plurality of predetermined positions for effecting sampling of said X-ray radiation beam detected by the detector; and
- changing a sequence of inspection operations in response to data from a computer wherein the sequence of operations includes at least one of the steps of:
  (1) moving the part in a linear pattern through the X-ray beam; and
  (2) rotating the part in the X-ray beam while maintaining the part at a selected linear position.

17. The method of claim 16 wherein the step of providing control signals further comprises the substeps of:
- providing control signals for effecting operation of a part manipulator to move the part into position for exposure to the X-ray beam; and
- receiving data indicating positioning of a part in the predetermined positions.

18. A method for computerized measuring and testing of a manufactured part, comprising the steps of:
- providing a beam of X-ray radiation;
- positioning a part in the X-ray radiation beam;
- moving the part linearly within said X-ray beam so that a predetermined area of the part is exposed to the X-ray beam radiation;
- measuring the intensity of radiation passing through the part;
- converting the measured intensity to an image of the part;
- identifying areas deserving of detailed analysis from the image of the part;
- positioning the part such that an area deserving of detailed analysis is located in the X-ray radiation beam;
- rotating the part about an axis normal to the plane of the X-ray beam so as to form an image of the part along a plane passing through each area deserving of detailed analysis;
- measuring the radiation passing through the area;
- converting the measured radiation to visual data;
- transmitting said digital data to a computer processing unit;
- converting in the computer processing unit the digital data to pixel image data; and
- generating a planar image of the area deserving analysis from the pixel image data.

* * * * *